United States Patent
He et al.

(10) Patent No.: US 10,984,213 B2
(45) Date of Patent: Apr. 20, 2021

(54) 3-DIMENSIONAL OPTICAL TOPOGRAPHICAL SENSING OF FINGERPRINTS USING UNDER-SCREEN OPTICAL SENSOR MODULE

(71) Applicant: Shenzhen Goodix Technology Co., Ltd., Shenzhen (CN)

(72) Inventors: Yi He, San Diego, CA (US); Bo Pi, San Diego, CA (US)

(73) Assignee: SHENZHEN GOODIX TECHNOLOGY CO., LTD., Shenzhen (CN)

(*) Notice: Subject to any disclaimer, the term of this patent is extended or adjusted under 35 U.S.C. 154(b) by 0 days.

(21) Appl. No.: 16/147,855

(22) Filed: Sep. 30, 2018

(65) Prior Publication Data

US 2019/0303639 A1    Oct. 3, 2019

Related U.S. Application Data

(60) Provisional application No. 62/648,898, filed on Mar. 27, 2018.

(51) Int. Cl.
*A61B 5/117* (2016.01)
*G06K 9/00* (2006.01)
(Continued)

(52) U.S. Cl.
CPC ......... *G06K 9/0004* (2013.01); *A61B 5/0073* (2013.01); *A61B 5/1172* (2013.01);
(Continued)

(58) Field of Classification Search
CPC ...... G06F 3/042; G06F 1/1626; G06F 3/0414; G06K 9/00013; G06K 9/0012; G06K 9/0002; G06T 1/00
See application file for complete search history.

(56) References Cited

U.S. PATENT DOCUMENTS 6,292,576 B1 * 9/2001 Brownlee .......... G06K 9/00006
340/5.83
7,751,595 B2   7/2010 Russo
(Continued)

FOREIGN PATENT DOCUMENTS

| CN | 107004126 A | 8/2017 |
| CN | 107004130 A | 8/2017 |

(Continued)

OTHER PUBLICATIONS

Holder, et al. "The Fingerprint Sourcebook", Chapter 2, U.S. Department of Justice, Office of Justice Programs, National Institute of Justice, Washington, DC 2011.
(Continued)

*Primary Examiner* — Lin Li
(74) *Attorney, Agent, or Firm* — Perkins Coie LLP

(57) ABSTRACT

Devices and optical sensor modules are provided for provide on-screen optical sensing of fingerprints by using an under-screen optical sensor module that captures and detects optical transmissive patterns in probe light that transmits through the internal finger tissues associated with the external fingerprint pattern formed on the outer finger skin to provide 3-dimensional topographical information for improved optical fingerprint sensing.

28 Claims, 60 Drawing Sheets

60a- Finger
431- Cover glass
450- Small holes in OLED TFT layers
600a- Fingerprint sensor core
600b- Fingerprint sensor package
937, 937b, 937c- Background light
939- Transmitted background light
941- Background light through TFT
971, 971a- Extra light sources
972- Coupling material
973- Probe light from extra light sources
975- Probe light through TFT
976- Probe light from extra light sources
977- Scattered light towards sensor
977a- Scattered light not towards sensor
979- Probe light coupled into finger tissues
981- Signal light from finger to sensor
983- Signal light through TFT

(51) Int. Cl.
*G06F 3/041* (2006.01)
*G06K 9/52* (2006.01)
*A61B 5/00* (2006.01)
*G06K 9/20* (2006.01)
*G09G 3/3208* (2016.01)
*A61B 5/1455* (2006.01)
*A61B 5/1172* (2016.01)
*A61B 5/145* (2006.01)
*G06F 3/042* (2006.01)

(52) U.S. Cl.
CPC ........ *A61B 5/1455* (2013.01); *A61B 5/14532* (2013.01); *G06K 9/0012* (2013.01); *G06K 9/2027* (2013.01); *G09G 3/3208* (2013.01); *G06F 3/0421* (2013.01); *G06K 9/0002* (2013.01); *G06K 2009/0006* (2013.01)

(56) References Cited

U.S. PATENT DOCUMENTS

| | | | |
|---|---|---|---|
| 9,946,914 B1* | 4/2018 | Kitchens, II | G06K 9/00114 |
| 10,024,655 B2* | 7/2018 | Raguin | A61B 5/117 |
| 2006/0062438 A1* | 3/2006 | Rowe | G06K 9/00046 |
| | | | 382/124 |
| 2006/0077385 A1* | 4/2006 | Wang | G01J 3/02 |
| | | | 356/328 |
| 2008/0298649 A1* | 12/2008 | Ennis | G06K 9/0012 |
| | | | 382/125 |
| 2012/0025951 A1* | 2/2012 | Rowe | G06K 9/2018 |
| | | | 340/5.83 |
| 2013/0279769 A1* | 10/2013 | Benkley, III | G06K 9/52 |
| | | | 382/124 |
| 2015/0195007 A1* | 7/2015 | He | G06F 3/0416 |
| | | | 455/41.1 |
| 2015/0242673 A1 | 8/2015 | Singhal | |
| 2015/0331508 A1 | 11/2015 | Nho et al. | |
| 2016/0012271 A1* | 1/2016 | Hansen | G06K 9/0002 |
| | | | 382/124 |
| 2016/0163278 A1* | 6/2016 | Pappas | G09G 5/00 |
| | | | 345/212 |
| 2016/0224816 A1 | 8/2016 | Smith et al. | |
| 2016/0314334 A1* | 10/2016 | He | G06K 9/0012 |
| 2017/0090024 A1* | 3/2017 | Kitchens, II | G06K 9/2009 |
| 2017/0255338 A1* | 9/2017 | Medina | G06F 3/0414 |
| 2017/0337413 A1* | 11/2017 | Bhat | G06K 9/0002 |
| 2018/0005005 A1 | 1/2018 | He et al. | |
| 2018/0014004 A1* | 1/2018 | Chen | G06K 9/00046 |
| 2019/0003977 A1* | 1/2019 | Costello | A61B 5/6898 |

FOREIGN PATENT DOCUMENTS

| | | |
|---|---|---|
| CN | 107169400 A | 9/2017 |
| CN | 107223232 A | 9/2017 |
| CN | 107251046 A | 10/2017 |
| CN | 107832752 A | 3/2018 |
| WO | 2017076292 A1 | 11/2015 |
| WO | 2016205832 A1 | 12/2016 |

OTHER PUBLICATIONS

International Search Report and Written Opinion dated Jan. 30, 2019, for International Application No. PCT/CN2018/113172, filed on Oct. 31, 2018.

Chinese Application No. 201880025132.6 Office Action dated Jun. 29, 2020 (pp. 1-26).

* cited by examiner

423- Display assembly
431- Enhanced cover glass
433- OLED display module
445, 447- Touching finger
613- Viewing zone
615- Effective Fingerprint sensing zone 524- Bottom layers
431- Cover glass
433- Display module
60- Finger tissues
61- Finger skin ridge
63- Finger skin valley
73- Display OLED
181- Cover glass reflected light
82, 201, 202, 211, 212- Light beams from an OLEDs group
185, 205, 206- Cover glass reflected light
187- Finger skin reflected light
189, 203, 204- Light coupled into finger tissues
191- Light scattered into the bottom layers
213, 214- Cover glass total reflected light 423- Display assembly
431- Enhanced cover glass
433- OLED display module
445, 447- Touching finger
613- Viewing zone
615- Effective sensing zone
617- Spacer
619- Color coating
621- Micro lens
623- Photodiode array 431- Enhanced cover glass
433- OLED display module
435- Circuits
613- Viewing zone
615- Effective sensing zone
618- Spacer with low RI
619- Color coating
621- Micro lens
623- Photodiode array
625- Detection axis 431- Enhanced cover glass
433- OLED display module
433b- OLED display module bottom
435- Circuits
613- Viewing zone
615- Effective sensing zone
618, 618b- Spacer with low RI
618c- Filling material
619, 619b- Color coating
621- Micro lens
623- Photodiode array
625- Detection axis 431 - Enhanced cover glass
433 - OLED display module
433b - OLED display module bottom
435 - Circuits
613 - Viewing zone
614 - Extra light sources
615 - Effective sensing zone
618, 618b - Spacer with low RI
618c - Filling material
619, 619b - Color coating
621 - Micro lens
623 - Photodiode array
625 - Detection axis

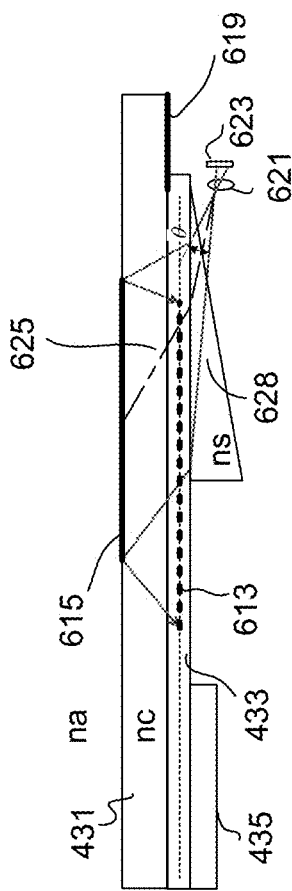
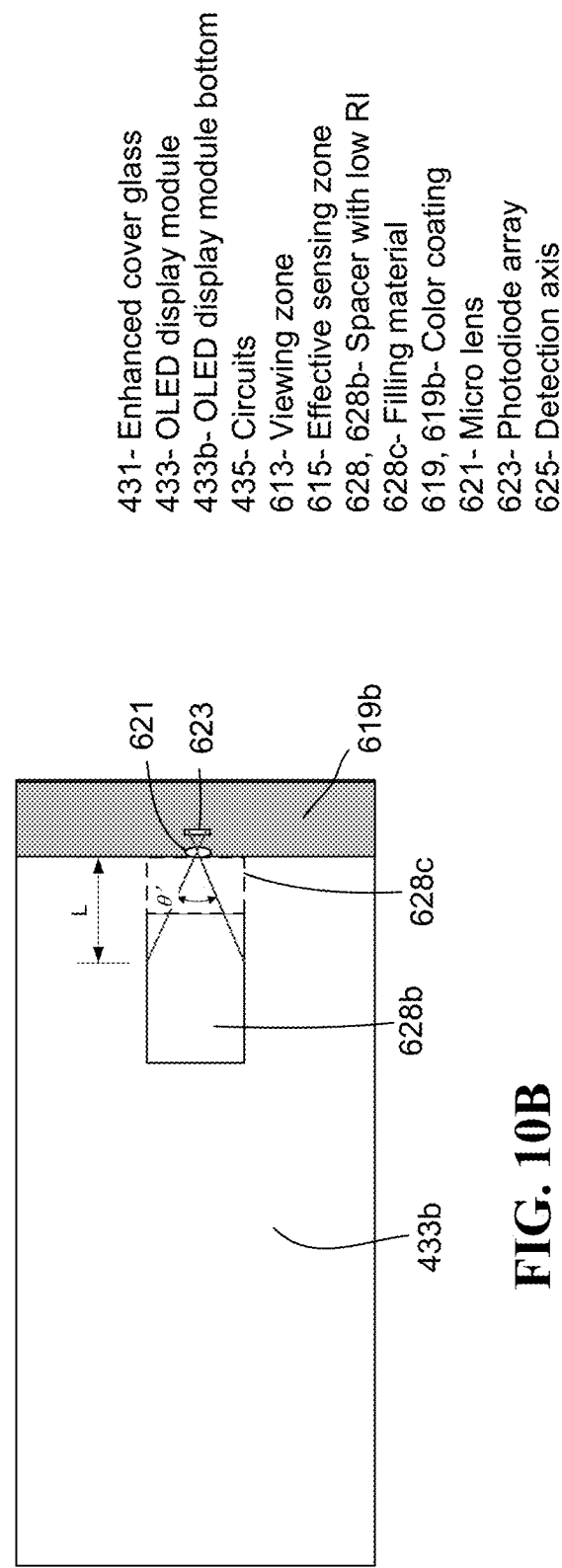
FIG. 10A
FIG. 10B
431- Enhanced cover glass
433- OLED display module
433b- OLED display module bottom
435- Circuits
613- Viewing zone
615- Effective sensing zone
628, 628b- Spacer with low RI
628c- Filling material
619, 619b- Color coating
621- Micro lens
623- Photodiode array
625- Detection axis

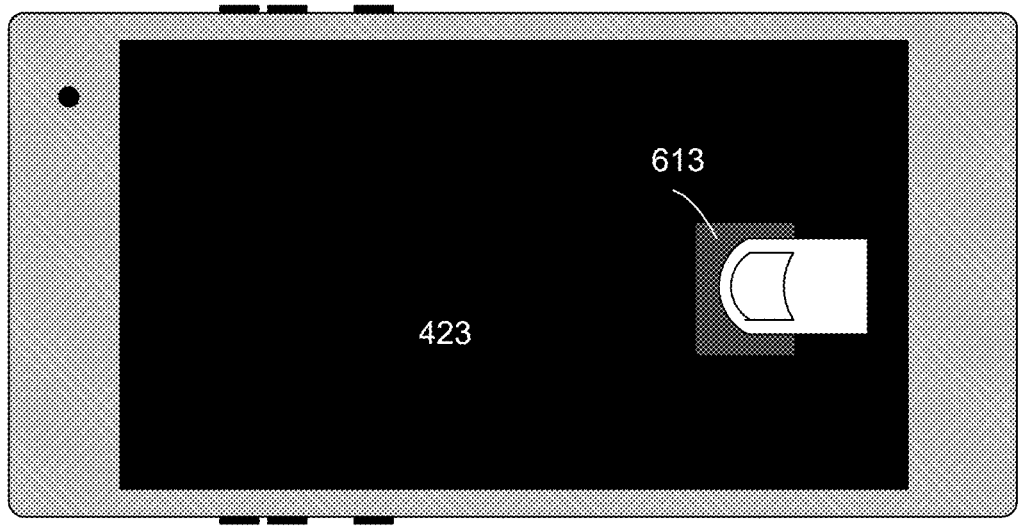

FIG. 21A

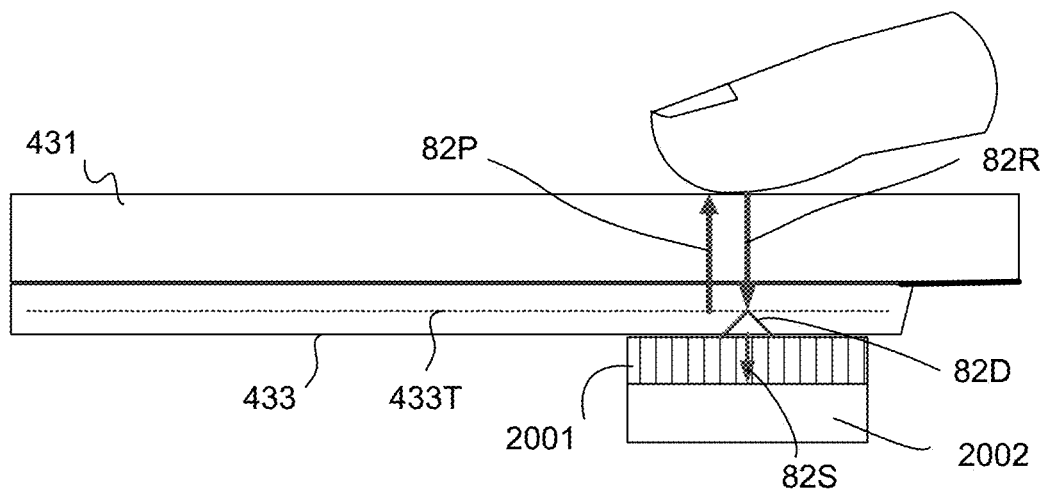

FIG. 21B

423- Display screen area
431- Cover glass
433- OLED display module
433T- TFT layer of the OLED display module
445, 447- Finger
613- Fingerprint sensing window within the display screen area
2001- Optical Collimators
2002- Photo detector array
82P- Light incident to the fingerprint sensing surface
82R- Light reflected from the fingerprint sensing surface
82D- Small hole arrays on TFT substrate
82S- Light that goes through the optical collimator array

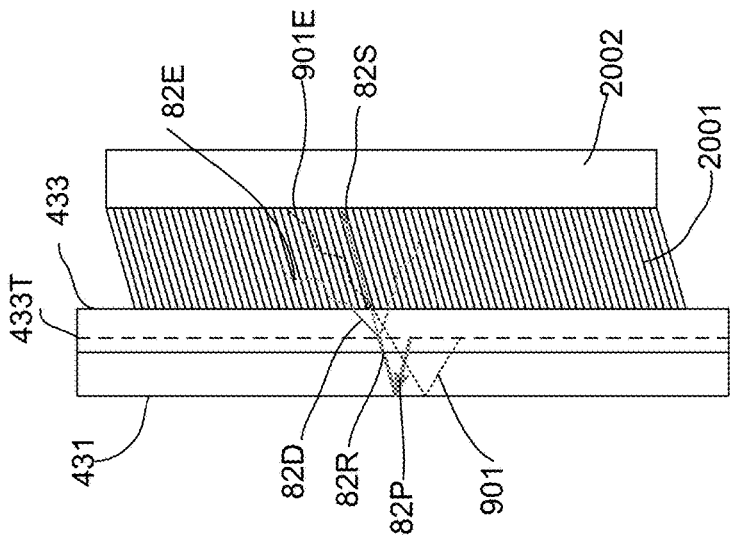

FIG. 22B

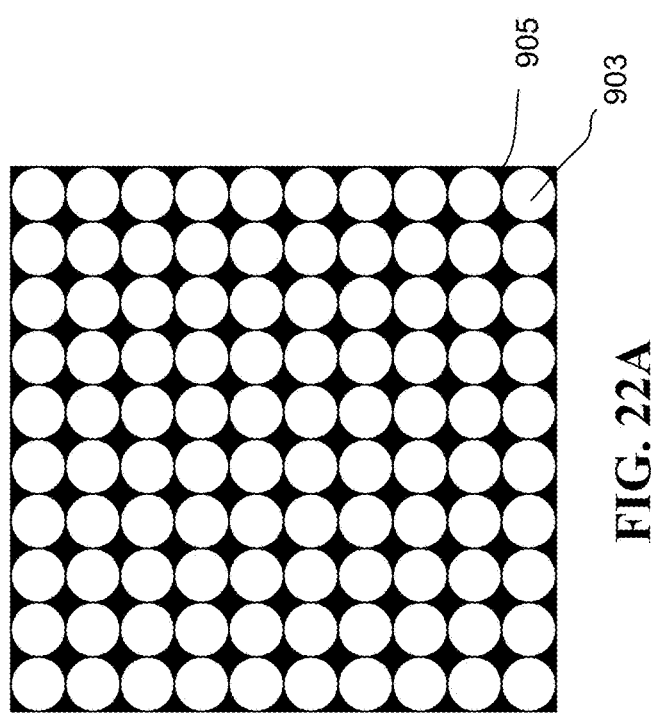

FIG. 22A

431- Cover glass
433- OLED display module
433T- TFT layer of OLED display module
2001- Optical Collimators
2002- Photo detector array
82P- Light incident to the fingerprint sensing surface
82R- Light reflected from the fingerprint sensing surface
82D- Light diffracted from TFT small holes of the OLED display module
82S- Light that goes through the optical collimator array
82E- Light absorbed by the optical collimator array
901- Other lights
901E- Light absorbed by the optical collimator array
903- Optical collimator array
905- Absorption materials

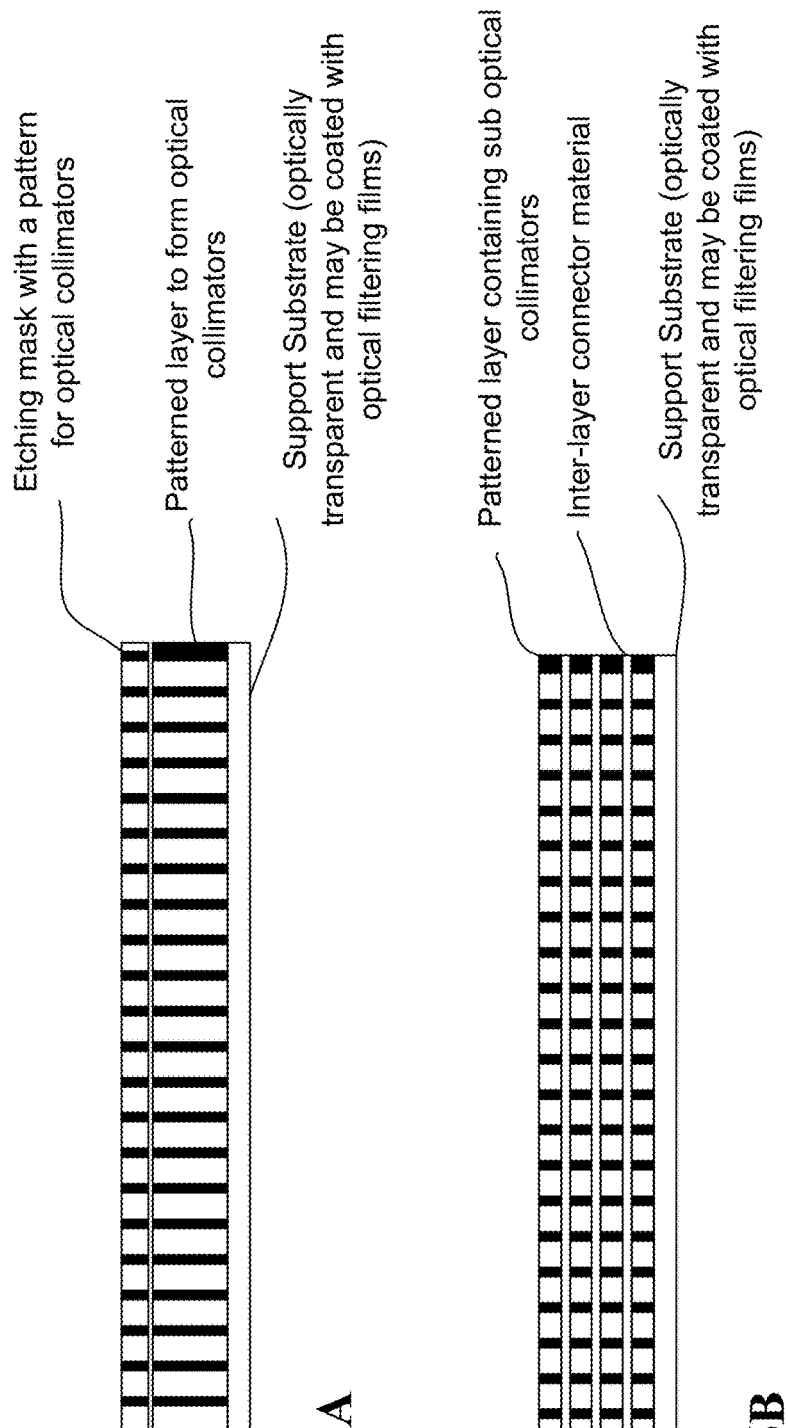
FIG. 26A
FIG. 26B
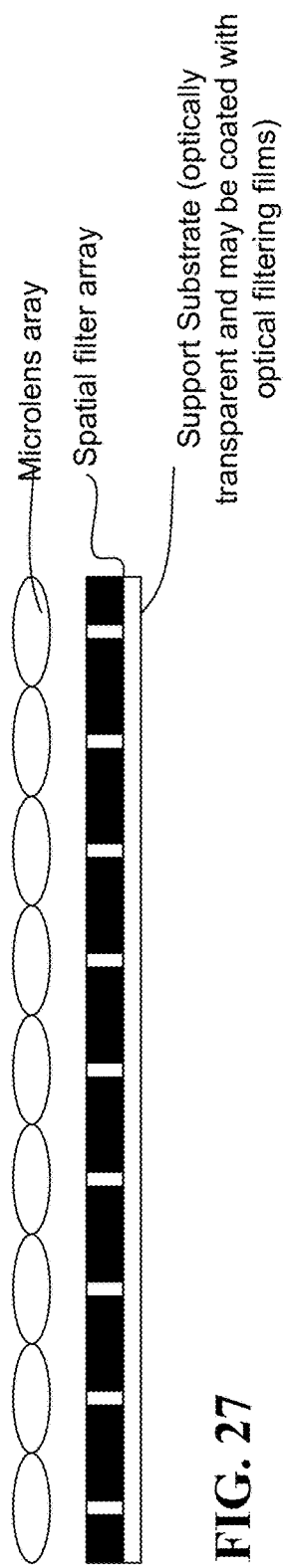
FIG. 27

431- Cover glass
433T- TFT layer of display module
618- One collimator Unit
681a- Filter films for the collimator unit
618b- FOV of a collimator unit
621- Photo detector array
621a- Pinhole image by a collimator unit 423- Display system
425- other sensor
427, 429- Side buttons
431- Cover glass
433- OLED display module
435- Electronics module
439- OLED pixel
617- Collimator
619- Color layer under cover glass
621- Photo detector array
623- Circuit board
450- small light transmitting holes in OLED display substrate
917- Spacer
919- Protection material

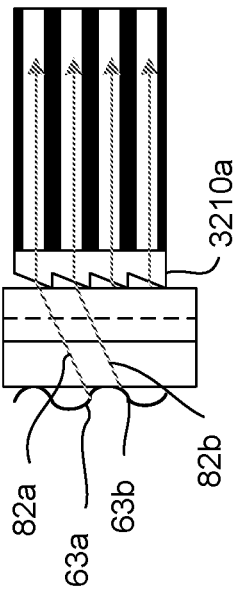
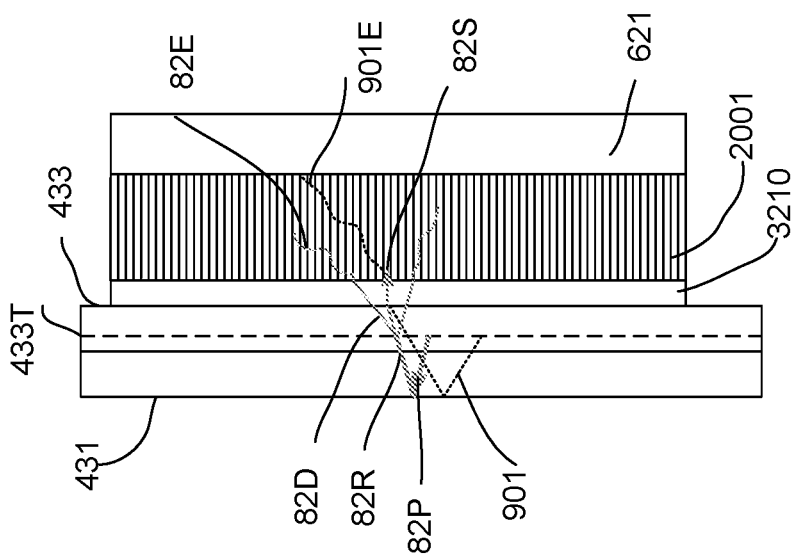
FIG. 32B
FIG. 32A

3301- Lightly pressed fingerprint
3303- Heavily pressed fingerprint
3305- Integration zone 60a- Finger
431- Cover glass
450- Small holes in OLED TFT layers
600a- Fingerprint sensor core
600b- Fingerprint sensor package
937, 937a- Background light
939, 939a- Transmitted background light
941, 941a- Filtered background light Pinhole camera type imaging optics Collimator type imaging optics

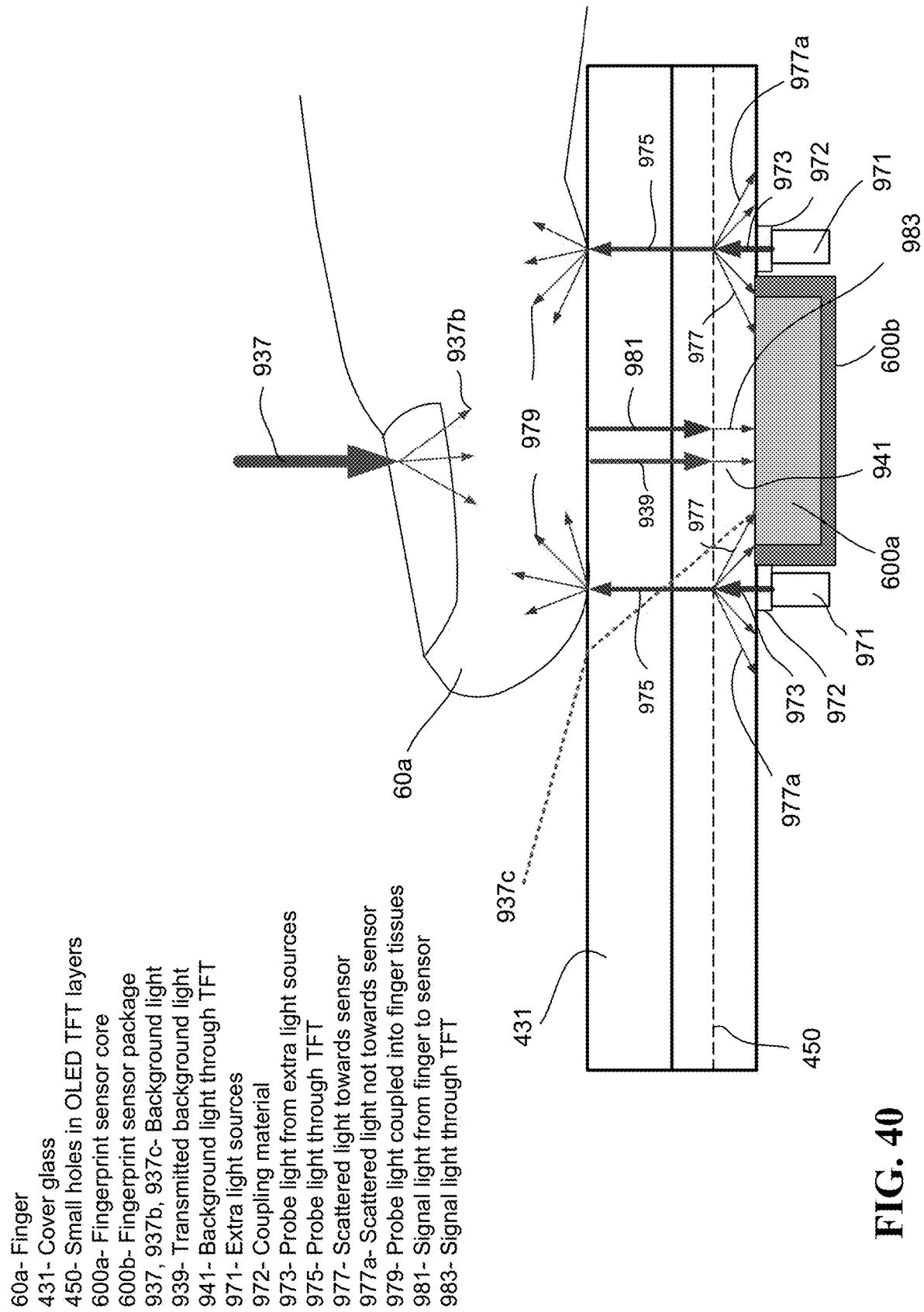

- 60a - Finger
- 431 - Cover glass
- 450 - Small holes in OLED TFT layers
- 600a - Fingerprint sensor core
- 600b - Fingerprint sensor package
- 937, 937b, 937c - Background light
- 939 - Transmitted background light
- 941 - Background light through TFT
- 971 - Extra light sources
- 972 - Coupling material
- 973 - Probe light from extra light sources
- 975 - Probe light through TFT
- 977 - Scattered light towards sensor
- 977a - Scattered light not towards sensor
- 979 - Probe light coupled into finger tissues
- 981 - Signal light from finger to sensor
- 983 - Signal light through TFT

FIG. 40

Control the extra illumination light sources outside the optical sensor module to sequentially produce different illumination probe light beams to illuminate a finger, one extra illumination light source at a time, from different directions, respectively, so that the probe light in each illumination probe light beam enters the finger and is scattered by internal tissues of the finger to cause a transmission of a portion of the scattered probe light inside the finger to through internal tissues of ridges and valleys of the finger to carry both (1) a first 2-dimensional transmissive pattern representing a fingerprint pattern formed by bridges and valleys of the finger, and (2) a first fingerprint tomographic pattern that is associated with the illumination of internal tissues of ridges and valleys of the finger in the first illumination direction and is embedded within the first 2-dimensional transmissive pattern

Operate the optical sensor module to capture fingerprint images carried by scattered probe light from scattering of the different illumination probe light beams inside the finger, respectively

Process the captured fingerprint images caused by the different illumination probe light beams, respectively, to extract spatial shifts in the captured fingerprint images associated with the different directions of the different illumination probe light beams and a 3-D tomographic profile of the fingerprint pattern that is superimposed on the scattered probe light from inside the finger

Process the extracted spatial shifts in the captured fingerprint images associated with the different directions of the different illumination probe light beams in determining whether the captured fingerprint images are from a person's finger

FIG. 42B

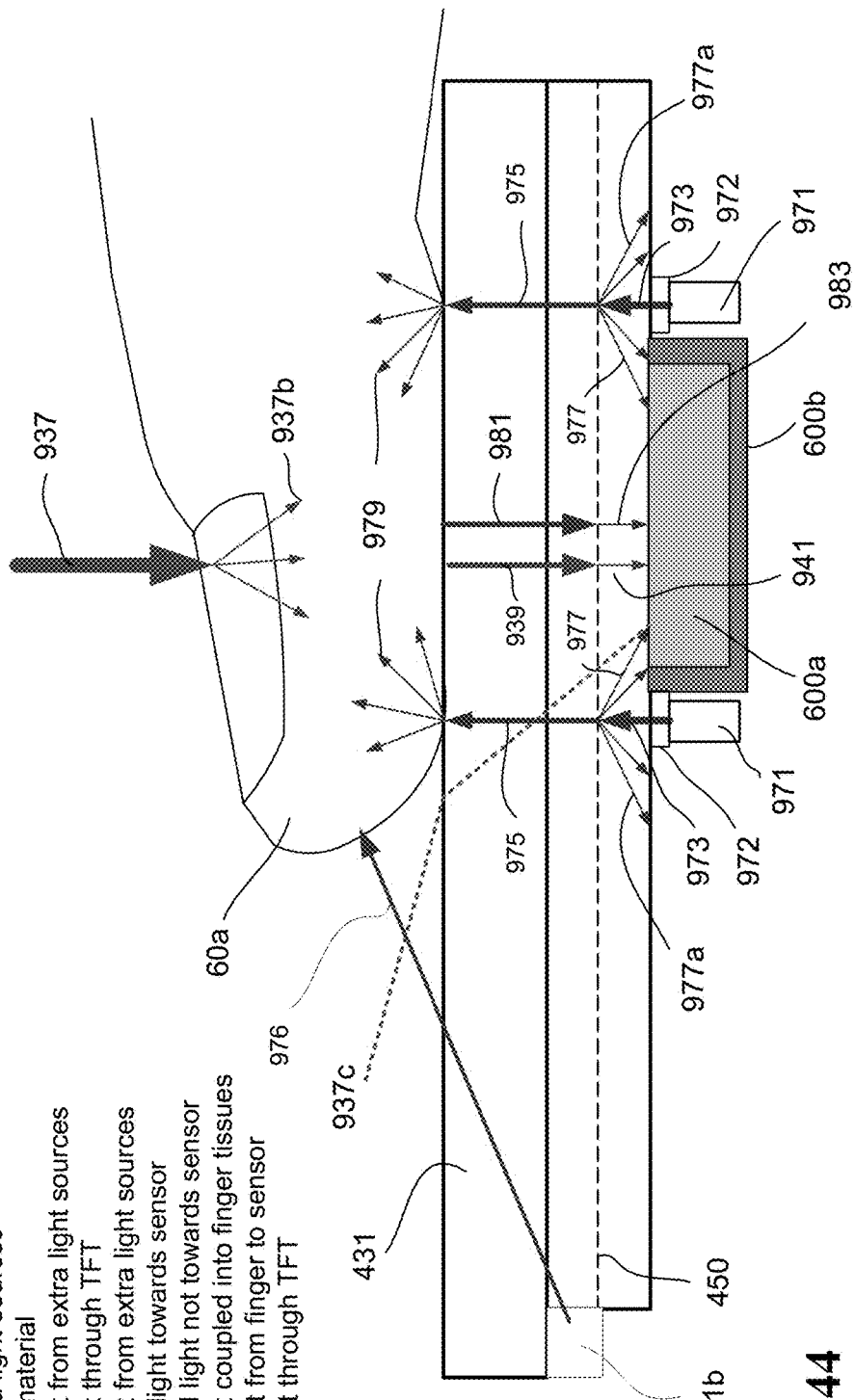

60a- Finger
431- Cover glass
450- Small holes in OLED TFT layers
600a- Fingerprint sensor core
600b- Fingerprint sensor package
937, 937b, 937c- Background light
939- Transmitted background light
941- Background light through TFT
971, 971b- Extra light sources
972- Coupling material
973- Probe light from extra light sources
975- Probe light through TFT
976- Probe light from extra light sources
977- Scattered light towards sensor
977a- Scattered light not towards sensor
979- Probe light coupled into finger tissues
981- Signal light from finger to sensor
983- Signal light through TFT

FIG. 44

431- Enhanced cover glass
433- OLED display module
435- Circuits
615- Effective sensing zone
615a- Viewing zone edge
618e- Spacer with low refractive index
621e- Micro lens
621f- Pinhole substrate
621g- Pinhole structure with an opening 643
621h- Spacer
623e- Photodiode array
623f- FPC etc.
623g- Protection material
620- Sensor module 447- Touching finger
633, 635, 637, 639, 641- Optical material layers above pinhole
643- Pinhole
645, 647, 649- Optical material layers below pinhole
623e- Photodiode array
651- Object
653- Image with barrel distortion
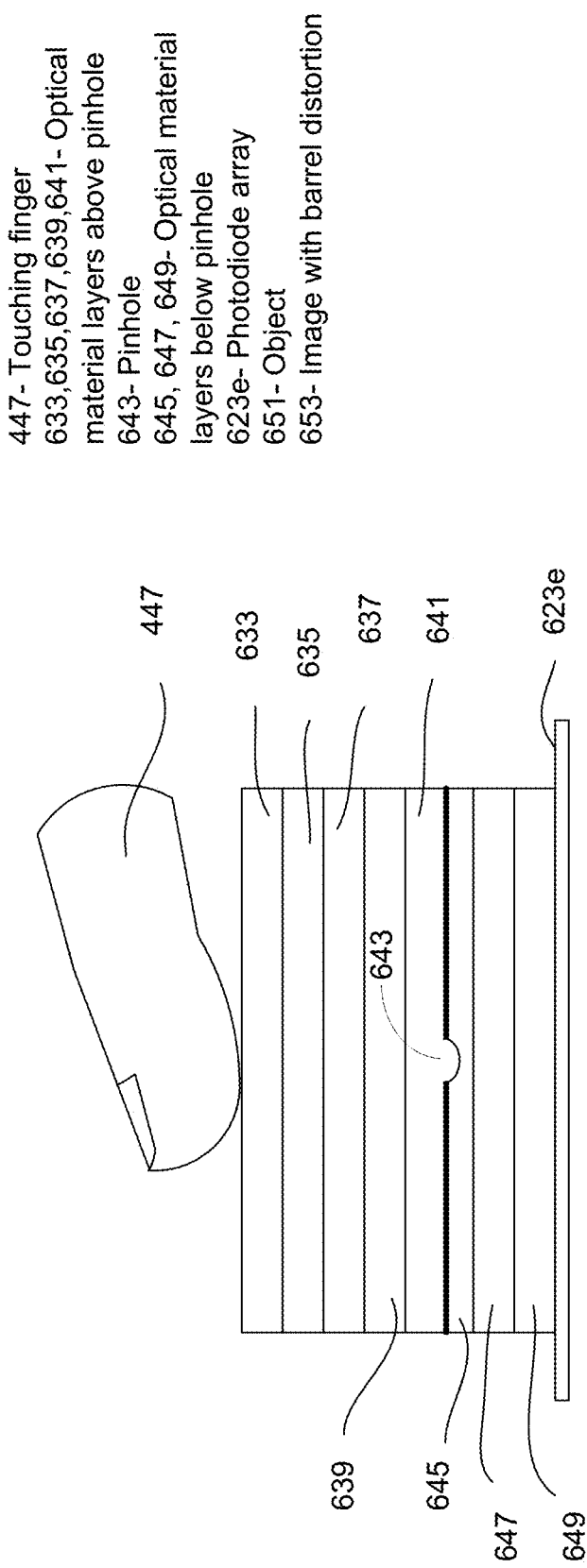
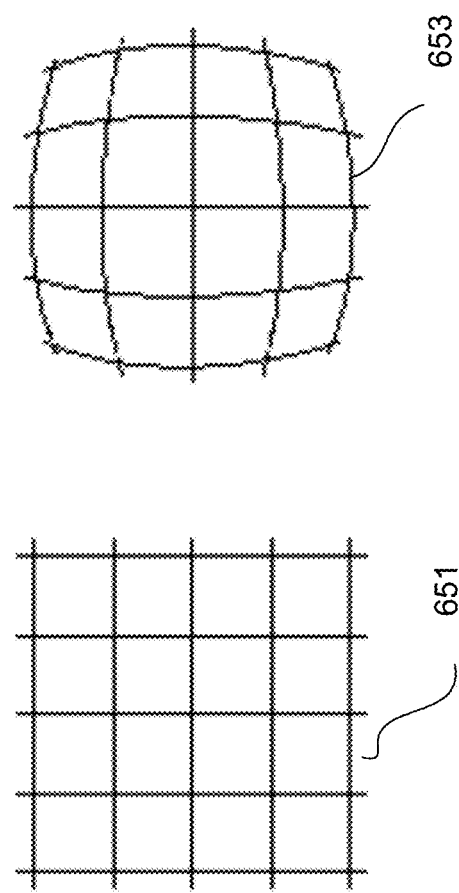
FIG. 47

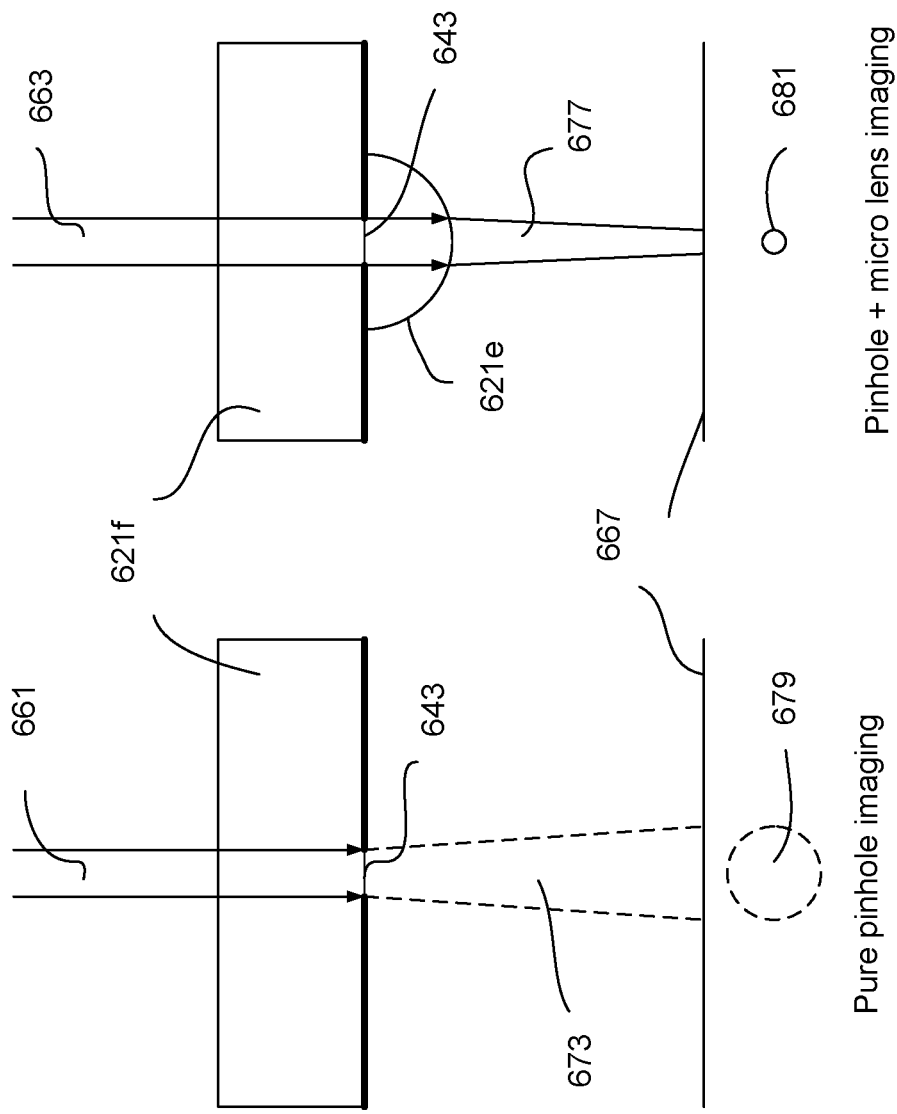
FIG. 48A Pure pinhole imaging
FIG. 48B Pinhole + micro lens imaging

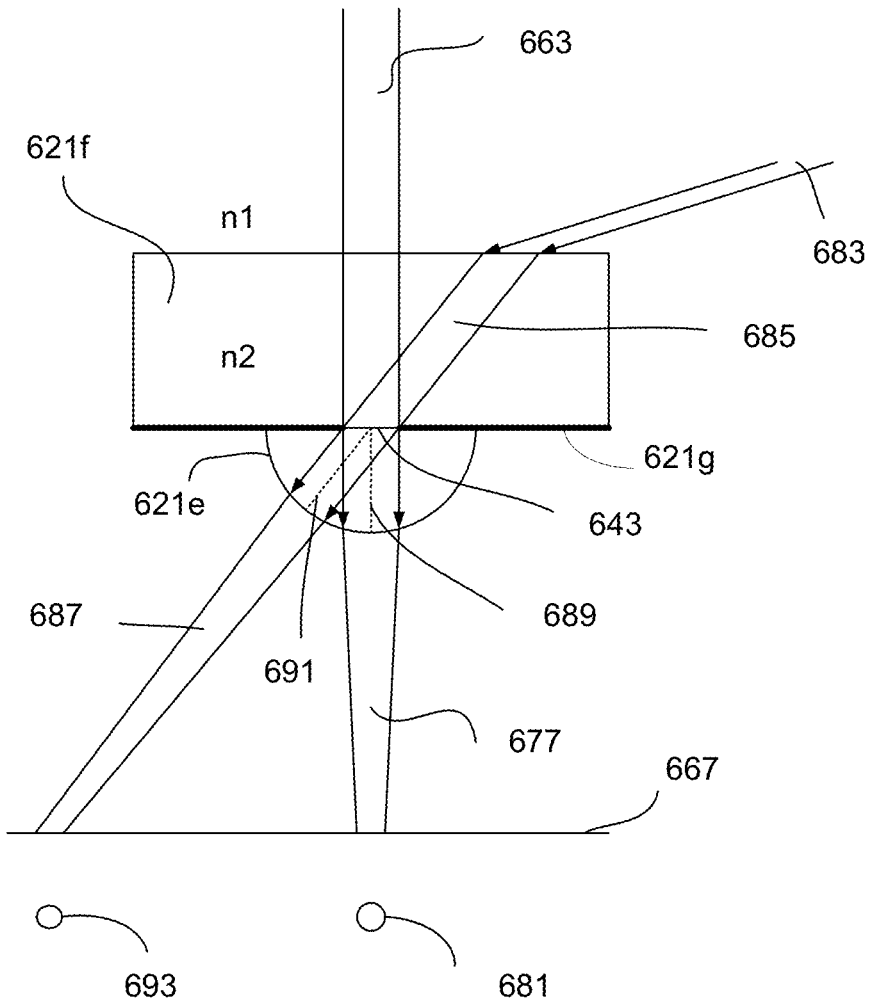

663- Light beam from an object
665- Substrate of the pinhole
667- Image plane
671- Pinhole
675- Micro lens
677- Converging light beam
681- Image spot of a pinhole + micro lens
683- Light beam with large incident angle
685- Refracted light beam of a beam with large incident angle
687- Converging light beam of a beam with large incident angle
689, 691- Axis of the micro lens
693- Light spot of a light beam with large incident angle
n1- Refractive index of the media above the pinhole substrate
n2- Refractive index of the pinhole substrate

FIG. 49

Transmission modification filter

431- Cover glass
433- OLED display module
433a- Protection layer of the OLED module
435- Electronics module
613a- Sensing zone
620- Sensor module
620a- Package of the sensor module
621- Photo detector array
623- Circuit board
631- Spacer materials

3-DIMENSIONAL OPTICAL TOPOGRAPHICAL SENSING OF FINGERPRINTS USING UNDER-SCREEN OPTICAL SENSOR MODULE

CROSS REFERENCE TO RELATED APPLICATIONS

This patent document claims the priority and benefits of prior U.S. Provisional Patent Application No. 62/648,898 entitled "3-DIMENSIONAL OPTICAL TOPOGRAPHICAL SENSING OF FINGERPRINTS USING UNDER-SCREEN OPTICAL SENSOR MODULE" and filed Mar. 27, 2018 by Applicant Shenzhen Goodix Technology Co., Ltd.

TECHNICAL FIELD

This patent document relates to sensing of fingerprints and performing one or more sensing operations of other parameter measurements of in electronic devices or systems, including portable devices such as a mobile device or a wearable device and larger systems.

BACKGROUND

Various sensors can be implemented in electronic devices or systems to provide certain desired functions. There is an increasing need for securing access to computers and computer-controlled devices or systems where only authorized users be identified and be distinguished from non-authorized users.

For example, mobile phones, digital cameras, tablet PCs, notebook computers and other portable electronic devices have become more and more popular in personal, commercial and governmental uses. Portable electronic devices for personal use may be equipped with one or more security mechanisms to protect the user's privacy.

For another example, a computer or a computer-controlled device or system for an organization or enterprise may be secured to allow only authorized personnel to access to protect the information or the use of the device or system for the organization or enterprise.

The information stored in portable devices and computer-controlled databases, devices or systems, may be of certain characteristics that should be secured. For example, the stored information may be personal in nature, such as personal contacts or phonebook, personal photos, personal health information or other personal information, or confidential information for proprietary use by an organization or enterprise, such as business financial information, employee data, trade secrets and other proprietary information. If the security of the access to the electronic device or system is compromised, the data may be accessed by others that are not authorized to gain the access, causing loss of privacy of individuals or loss of valuable confidential information. Beyond security of information, securing access to computers and computer-controlled devices or systems also allow safeguard of the use of devices or systems that are controlled by computers or computer processors such as computer-controlled automobiles and other systems such as ATMs.

Secured access to a device such as a mobile device or a system such as an electronic database and a computer-controlled system can be achieved in different ways including using user passwords. A password, however, may be easily to be spread or obtained and this nature of passwords can reduce the level of the security in using passwords alone. Moreover, a user needs to remember a password to use password-protected electronic devices or systems, and, if the user forgets the password, the user needs to undertake certain password recovery procedures to get authenticated or otherwise regain the access to the device. Unfortunately, in various circumstances, such password recovery processes may be burdensome to users and have various practical limitations and inconveniences.

The personal fingerprint identification can be utilized to achieve the user authentication for enhancing the data security while mitigating certain undesired effects associated with passwords.

Electronic devices or systems, including portable or mobile computing devices, may employ user authentication mechanisms to protect personal or other confidential data and prevent unauthorized access. User authentication on an electronic device or system may be carried out through one or multiple forms of biometric identifiers, which can be used alone or in addition to conventional password authentication methods. One form of biometric identifiers is a person's fingerprint pattern. A fingerprint sensor can be built into an electronic device or system to read a user's fingerprint pattern as part of the authentication process so that the device or system can only be unlocked by an authorized user through authentication of the authorized user's fingerprint pattern.

SUMMARY

The sensor technology and examples of implementations of the sensor technology described in this patent document provide an optical sensor module under a display panel for optical sensing of fingerprints and additional optical sensing functions. Implementations of the disclosed optical sensing can be used to obtain optical transmissive patterns in probe light that transmits through the internal finger tissues associated with the external fingerprint pattern formed on the outer finger skin to provide 3-dimensional topographical information for improved optical fingerprint sensing.

In one aspect, the disclosed technology can be implemented to provide an electronic device capable of detecting a fingerprint by optical sensing. This device includes a display panel that displays images; a top transparent layer formed over the display panel as an interface for user touch operations and for transmitting the light from the display panel to display images, the top transparent layer including a designated fingerprint sensing area for a user to place a finger for fingerprint sensing; and an optical sensor module located below the display panel and underneath the designated fingerprint sensing area on the top transparent layer to receive light from the top transparent layer to detect a fingerprint, wherein the optical sensor module includes an optical sensor array of optical detectors to convert the received light that carries a fingerprint pattern of the user into detector signals representing the fingerprint pattern.

This device further includes extra illumination light sources located outside the optical sensor module at different locations to produce different illumination probe beams to illuminate the designated fingerprint sensing area on the top transparent layer in different illumination directions, each extra illumination light source structured to produce probe light in an optical spectral range with respect to which tissues of a human finger exhibit optical transmission to allow probe light in each illumination probe beam to enter a user finger over the designated fingerprint sensing area on the top transparent layer to produce scattered probe light by scattering of tissues inside the finger that propagates towards and passes the top transparent layer to carry both (1) fingerprint pattern information and (2) different fingerprint topographical information associated with the different illumination directions, respectively, caused by transmission through internal tissues of ridges and valleys of the finger; and a probe illumination control circuit coupled to control the extra illumination light sources to sequentially turn on and off in generating the different illumination probe beams at different times, one beam at a time, so that the optical sensor module located below the display panel is operable to sequentially detect the scattered probe light from the different illumination probe beams to capture both (1) the fingerprint pattern information and (2) the different fingerprint topographical information associated with the different illumination directions, respectively.

In another aspect, the disclosed technology can be implemented to provide a method for operating an electronic device to detect a fingerprint by optical sensing, wherein the electronic device includes a display panel that displays images, a top transparent layer formed over the display panel as an interface for user touch operations and for transmitting the light from the display panel to display images, and an optical sensor array of optical detectors located under the display panel. This the method includes directing a first illumination probe beam to illuminate a designated fingerprint sensing area over the top transparent layer in a first illumination direction and to enter a user finger over the designated fingerprint sensing area to produce first scattered probe light by scattering of tissues inside the finger that propagates towards and passes the top transparent layer by transmission through internal tissues of ridges and valleys of the finger to carry both (1) a first 2-dimensional transmissive pattern representing a fingerprint pattern formed by bridges and valleys of the finger, and (2) a first fingerprint topographical pattern that is associated with the illumination of internal tissues of ridges and valleys of the finger in the first illumination direction and is embedded within the first 2-dimensional transmissive pattern. This further also includes operating the optical sensor array to detect transmitted part of the first scattered probe light that passes through the top transparent layer and the display panel to reach the optical sensor array so as to capture both (1) the first 2-dimensional transmissive pattern, and (2) the first fingerprint topographical pattern.

In addition, this method includes directing a second illumination probe beam, while turning off the first illumination light source, to illuminate the designated fingerprint sensing area over the top transparent layer in a second, different illumination direction and to enter the user finger to produce second scattered probe light by scattering of tissues inside the finger that propagates towards and passes the top transparent layer by transmission through internal tissues of ridges and valleys of the finger to carry both (1) a second 2-dimensional transmissive pattern representing the fingerprint pattern, and (2) a second fingerprint topographical pattern that is associated with the illumination of the internal tissues of ridges and valleys of the finger in the second illumination direction and that is embedded within the second 2-dimensional transmissive pattern, wherein the second topographical pattern is different from the first topographical pattern due to different beam directions of the first and second illumination probe beams. The optical sensor array is operated to detect transmitted part of the second scattered probe light that passes through the top transparent layer and the display panel to reach the optical sensor array so as to capture both (1) the second 2-dimensional transmissive pattern, and (2) the second fingerprint topographical pattern. Next, a detected fingerprint pattern is constructed from the first and second transmissive patterns and the first and second fingerprint topographical patterns are processed to determine whether the detected fingerprint pattern is from a natural finger.

Those and other aspects and their implementations are described in greater detail in the drawings, the description and the claims.

BRIEF DESCRIPTION OF THE DRAWINGS

FIGS. 10A-10B show examples of a under-screen optical sensor module that uses an optical coupler shaped as a thin wedge to improve the optical detection at the optical sensor array.

FIGS. 21A-21B show the operation of the optical sensor module in FIG. 20.

FIGS. 22A-22B show an exemplary implementation of the design in FIG. 20 and FIGS. 21A-21B.

FIGS. 26A and 26B show examples of fabricating collimators by etching.

FIG. 27 shows an array of optical spatial filters coupled with micro lens array where each microlens is located with respect to a corresponding through hole of an optical spatial filter so that each unit collimator includes a micro lens and a micro spatial filter, such as a micro hole.

FIGS. 32A and 32B show examples of an optical fingerprint sensor under an OLED display panel having an optical deflection or diffraction device or layer. The numerals in FIGS. 32A and 32B are used to represent the following:

431—Cover glass;
433—OLED display module;
433T—TFT layer of OLED display module;
3210—Viewing angle adaptor optical layer;
3210a—Detail of the viewing angle adaptor layer;
2001—Light Collimator;
621—Photo detector array;
63a, 63b—Different positions in fingerprint valley;
82a, 82b—Light from different fingerprint valley positions;
82P—Light shine to finger;
82R—Light reflected from finger surface;
82D—Light diffracted from TFT small holes;
82S—Light goes through collimator;
82E—Light absorbed by collimator;
901—Other lights; and
901E—Light absorbed by collimator.

Figure 33:
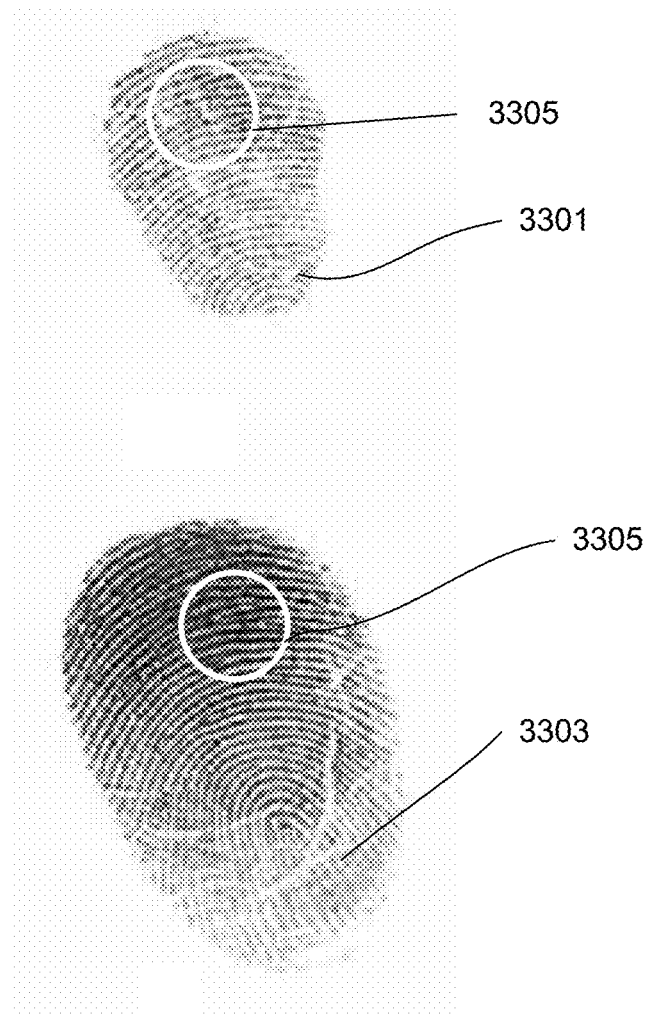

FIG. 33 shows two different fingerprint patterns of the same finger under different press forces: the lightly pressed fingerprint 2301 and the heavily pressed fingerprint 3303.

Figure 34:
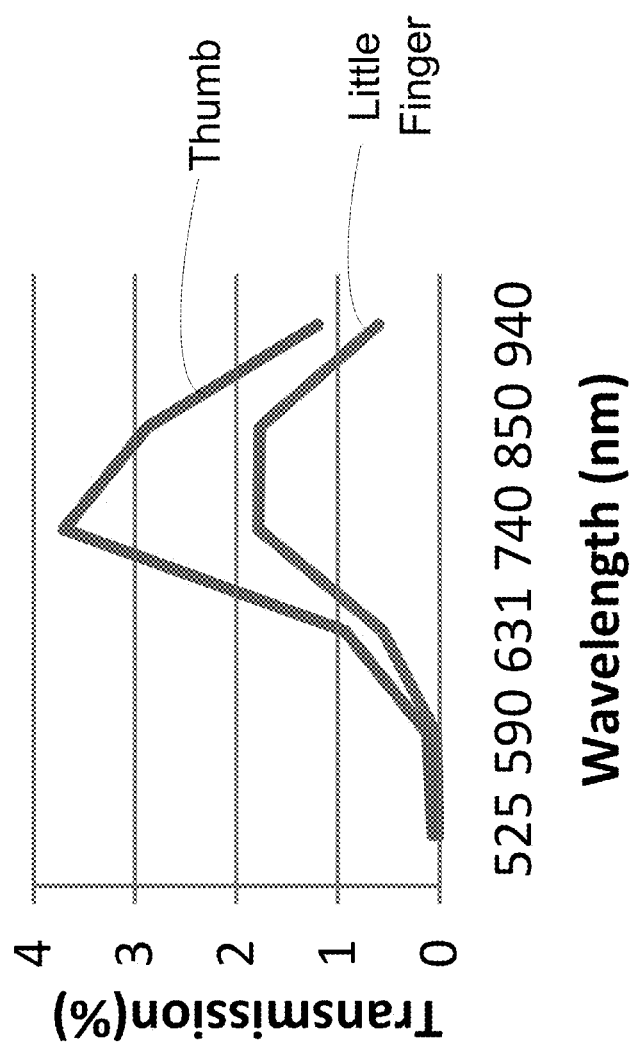

FIG. 34 shows an example of the optical transmission spectral profiles of a typical human thumb and litter finger at several different optical wavelengths from around 525 nm to around 940 nm.

Figure 35:
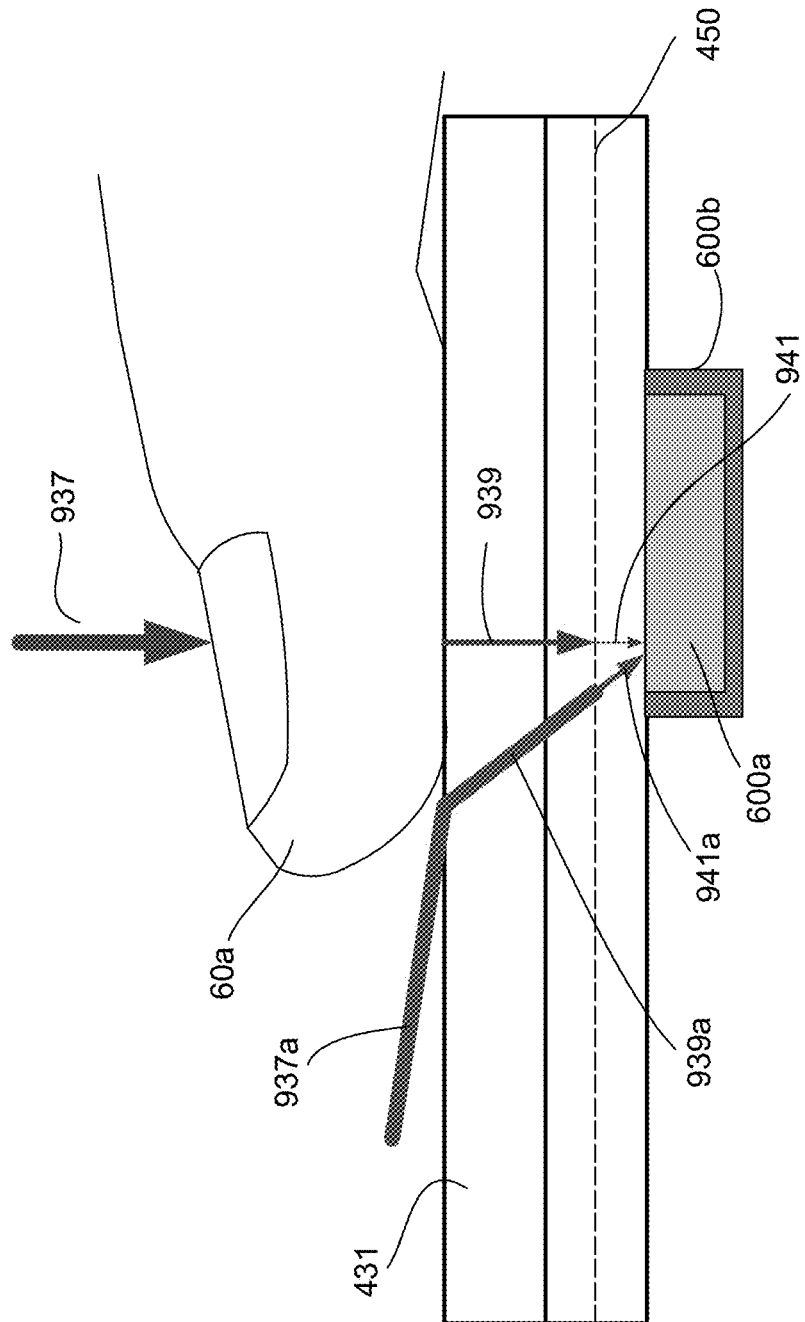

FIG. 35 illustrates influences of the background light in an example of a under-screen optical sensor module.

Figure 36:
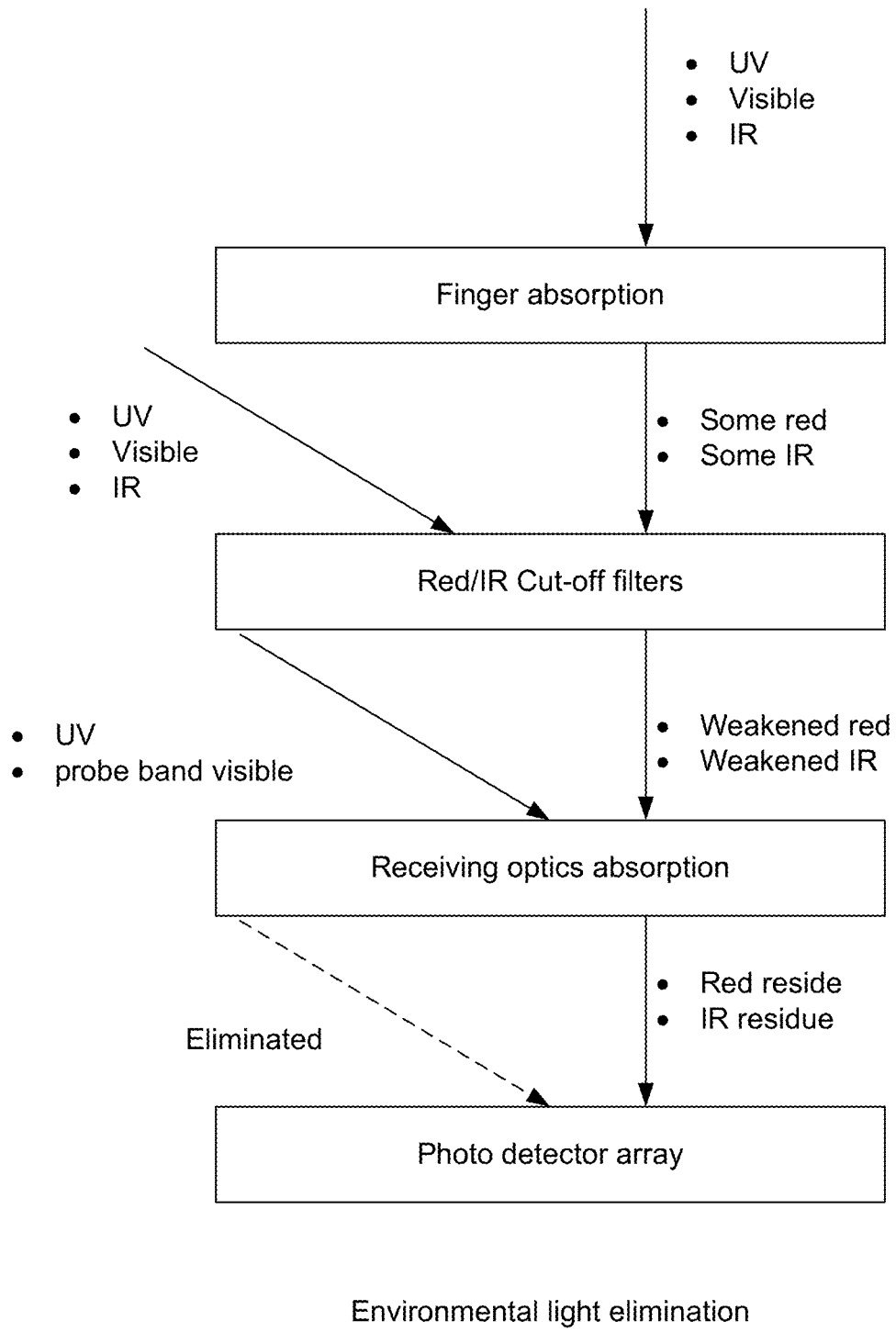

FIG. 36 shows an example of a design algorithm for designing the optical filtering in a under-screen optical sensor module for reducing background light.

Figures 37A, 37B:
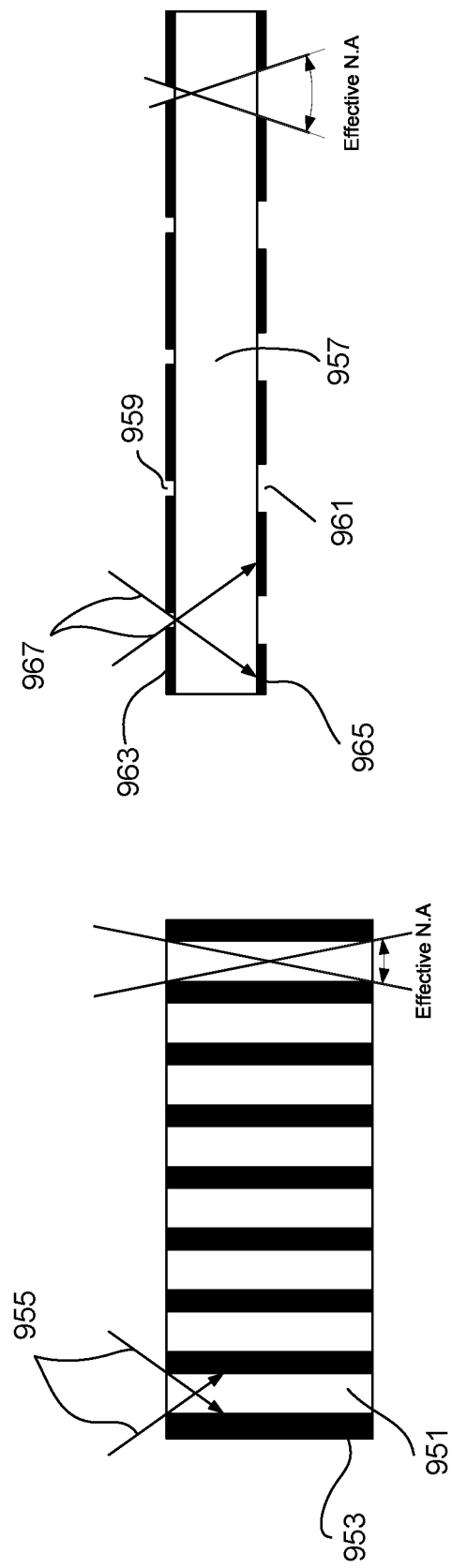

FIGS. 37A and 37B show two examples for an under-screen optical sensor module having an optical collimator array or an optical pinhole array before the optical detector array as part of the receiving optics with a small optical numerical aperture to reduce the background light that enters the optical detector array. The numerals in FIGS. 37A and 37B are used to represent the following:

951—Collimator pinhole;
953—Collimator wall material;
955, 967—Environmental light with large incident angles;
957—Substrate;
959—Imaging camera pinhole;
961—Aperture restriction hole; and
963, 965—Pinhole material.

Figure 38:
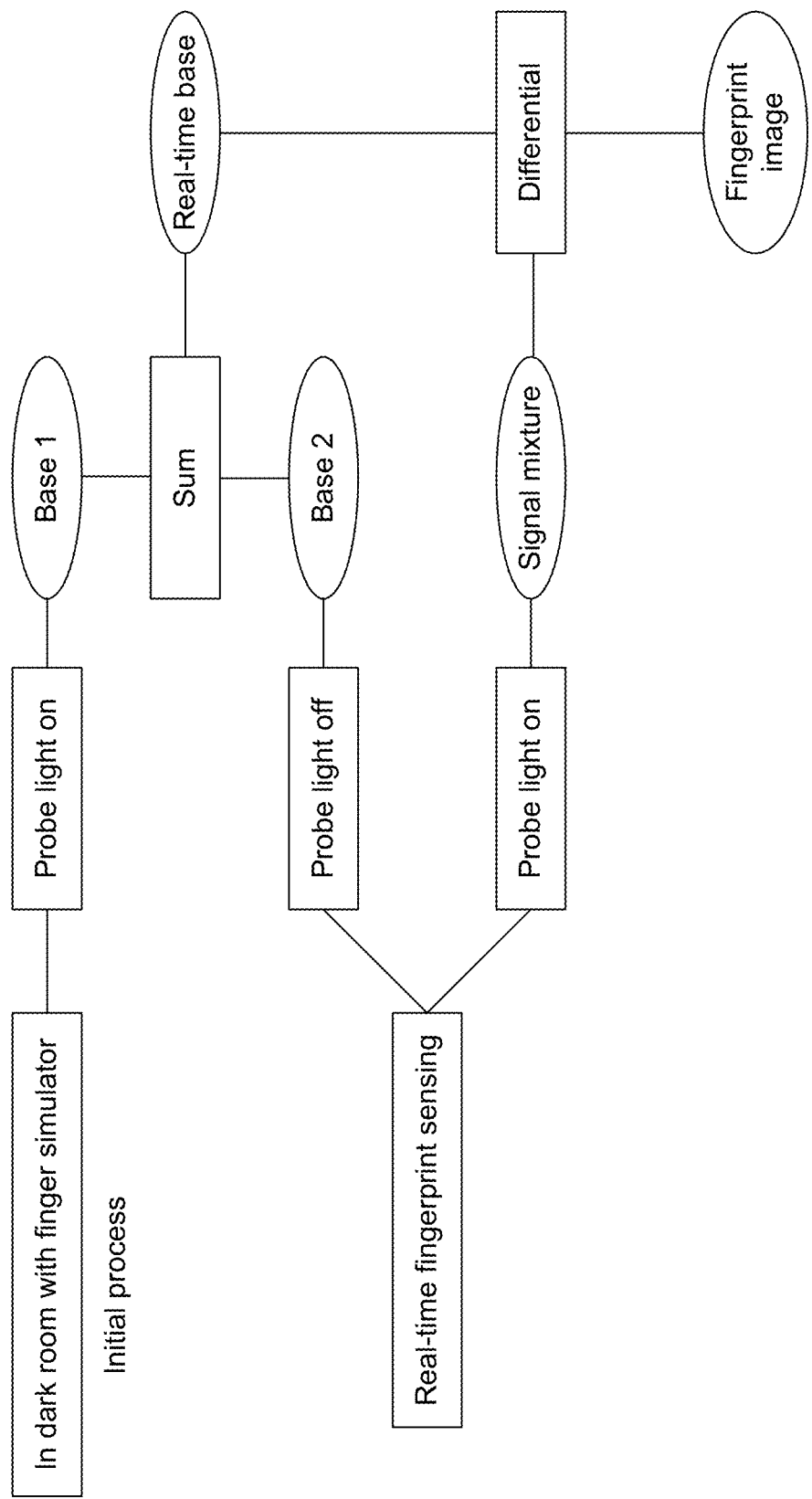

FIG. 38 illustrates an example of a sensor initialization process that measures a baseline background level at the optical sensor array each time a fingerprint is obtained.

Figure 39:
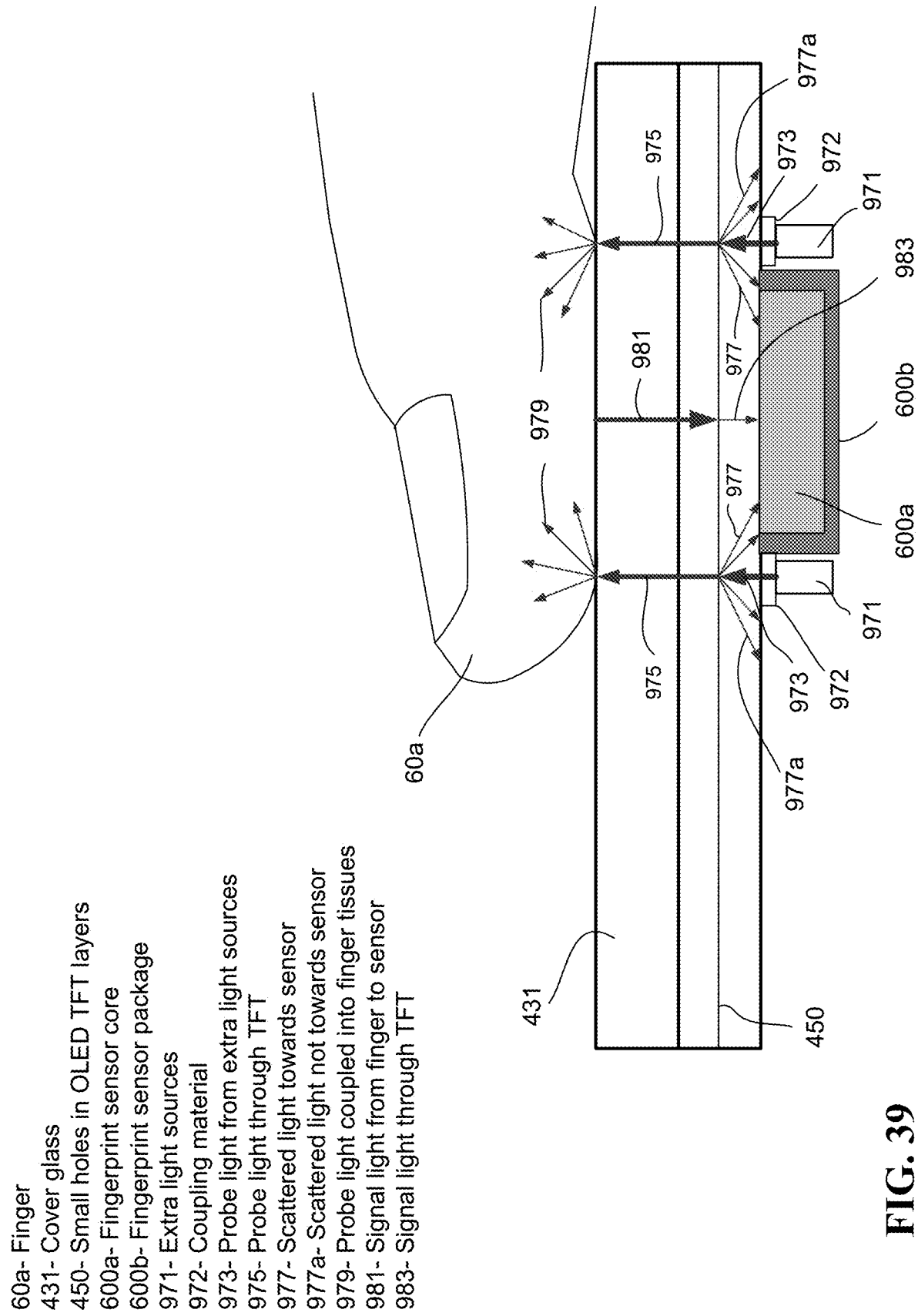

FIGS. 39 and 40 show behaviors different optical signals in an example of a under-screen optical sensor module having extra illumination light sources to supplement the fingerprint sensing illumination by the OLED display light.

Figure 41:
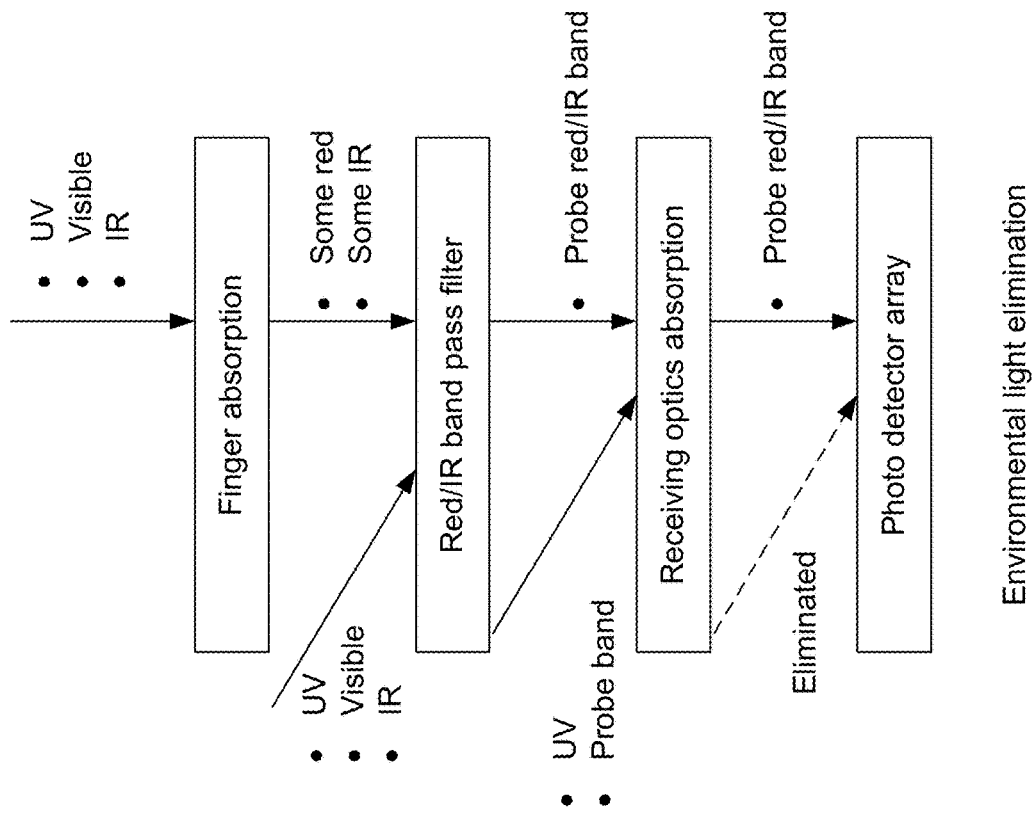

FIG. 41 shows an example of a design algorithm for designing the optical filtering in a under-screen optical sensor module for reducing background light in the presence of extra light sources for optical sensing.

Figure 5A:
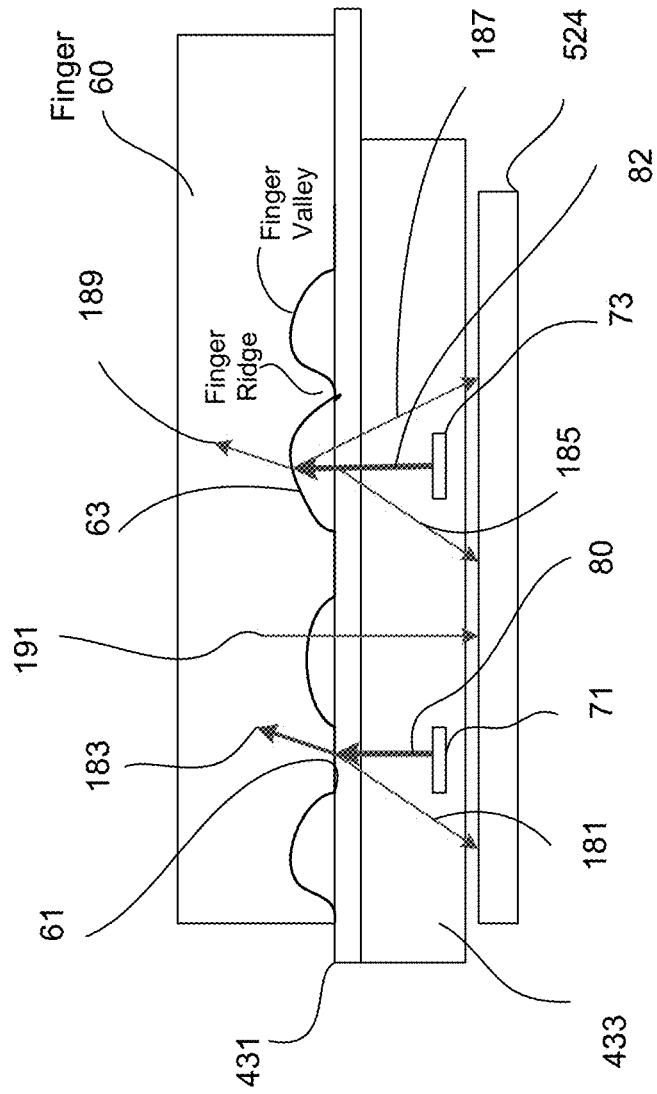
FIGS. 5A and 5B illustrate signal generation for the returned light from the sensing zone on the top sensing surface under two different optical conditions to obtain optical reflective patterns representing external fingerprint patterns formed on the outer skin of a finger and the operation of the under-screen optical sensor module.
Figure 5B:
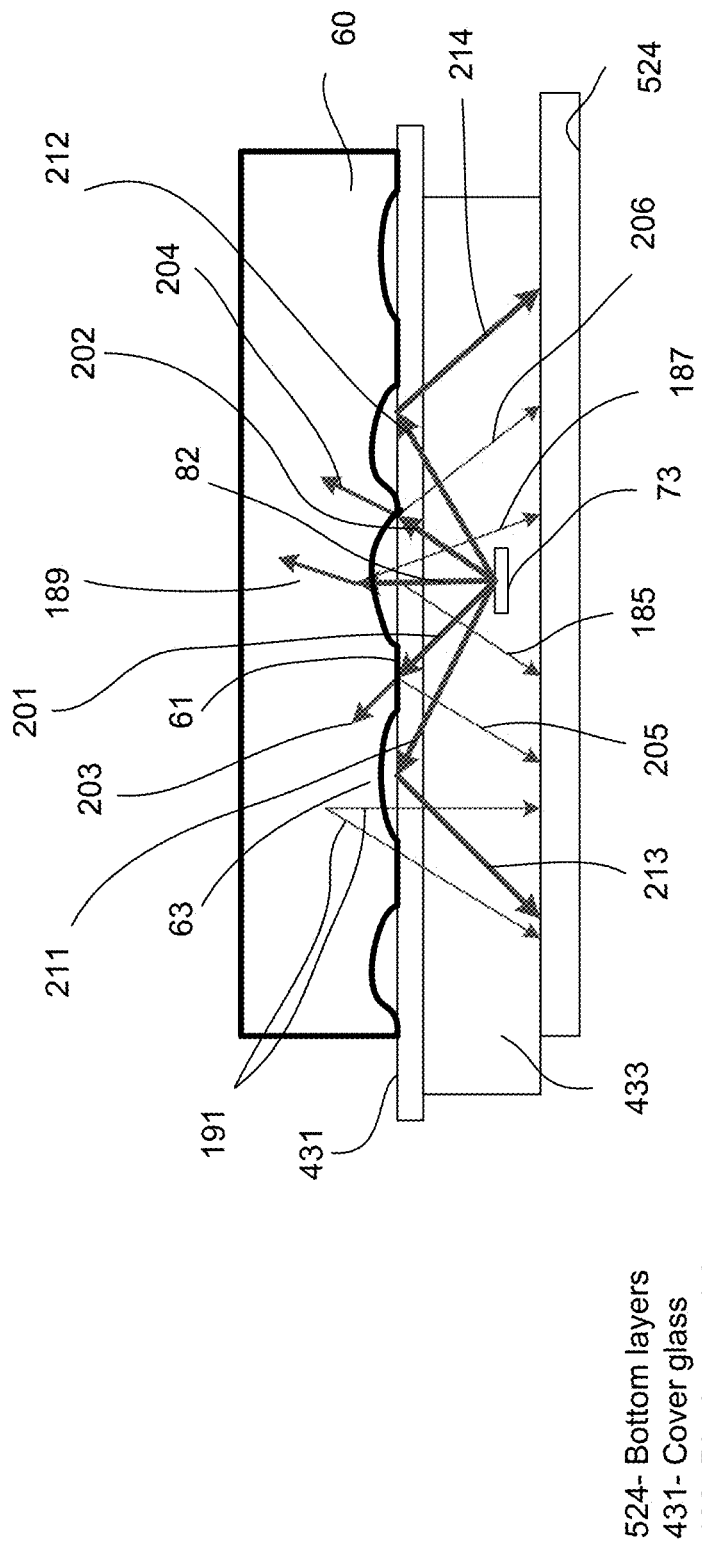
Figure 5C:
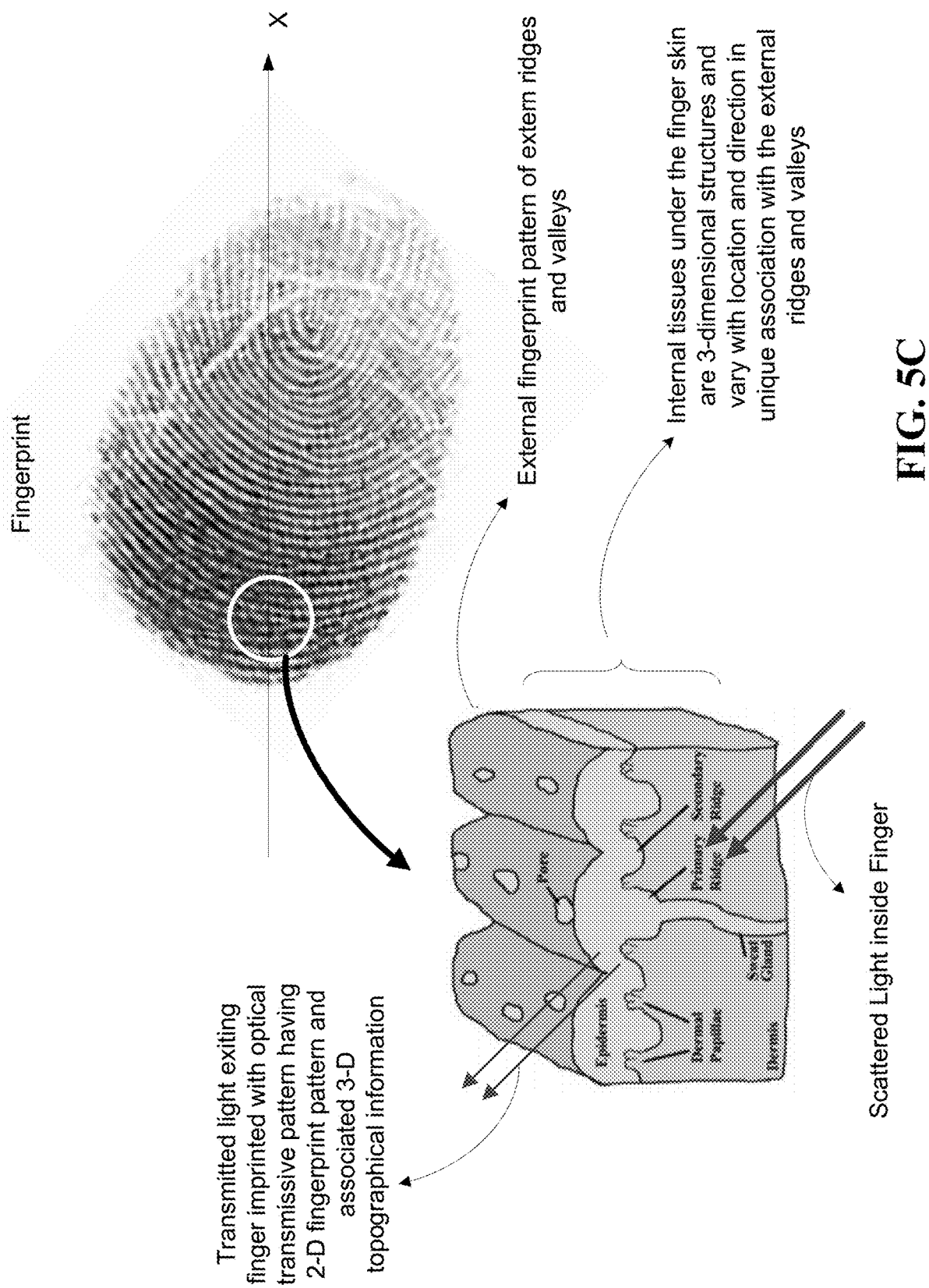
FIGS. 5C and 5D illustrate signal generation for the returned light from the sensing zone on the top sensing surface to obtain optical reflective patterns representing internal finger tissues associated with the external fingerprint patterns formed on the outer skin of a finger and the operation of the under-screen optical sensor module.
Figure 5D:
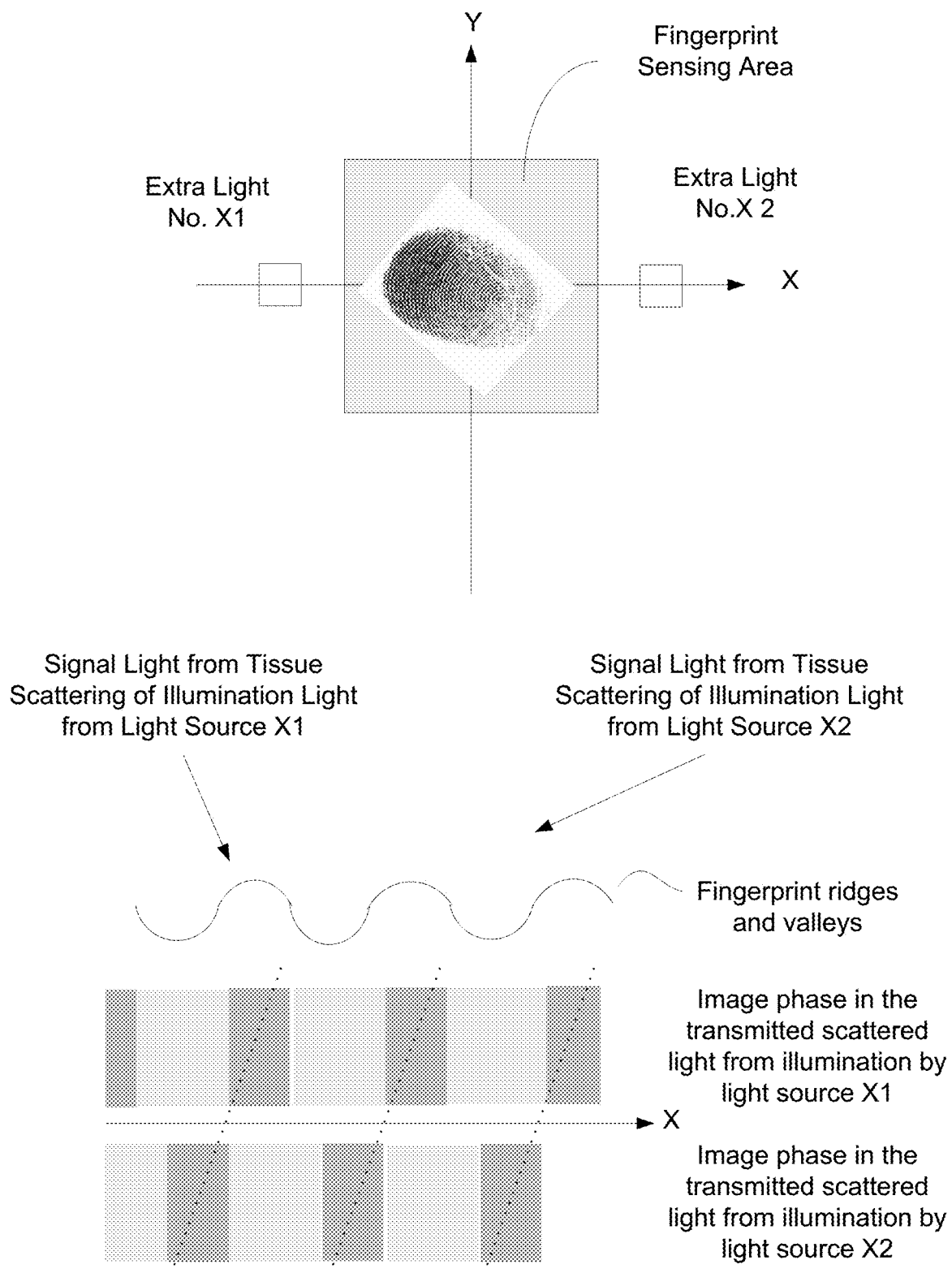
Figure 42A:
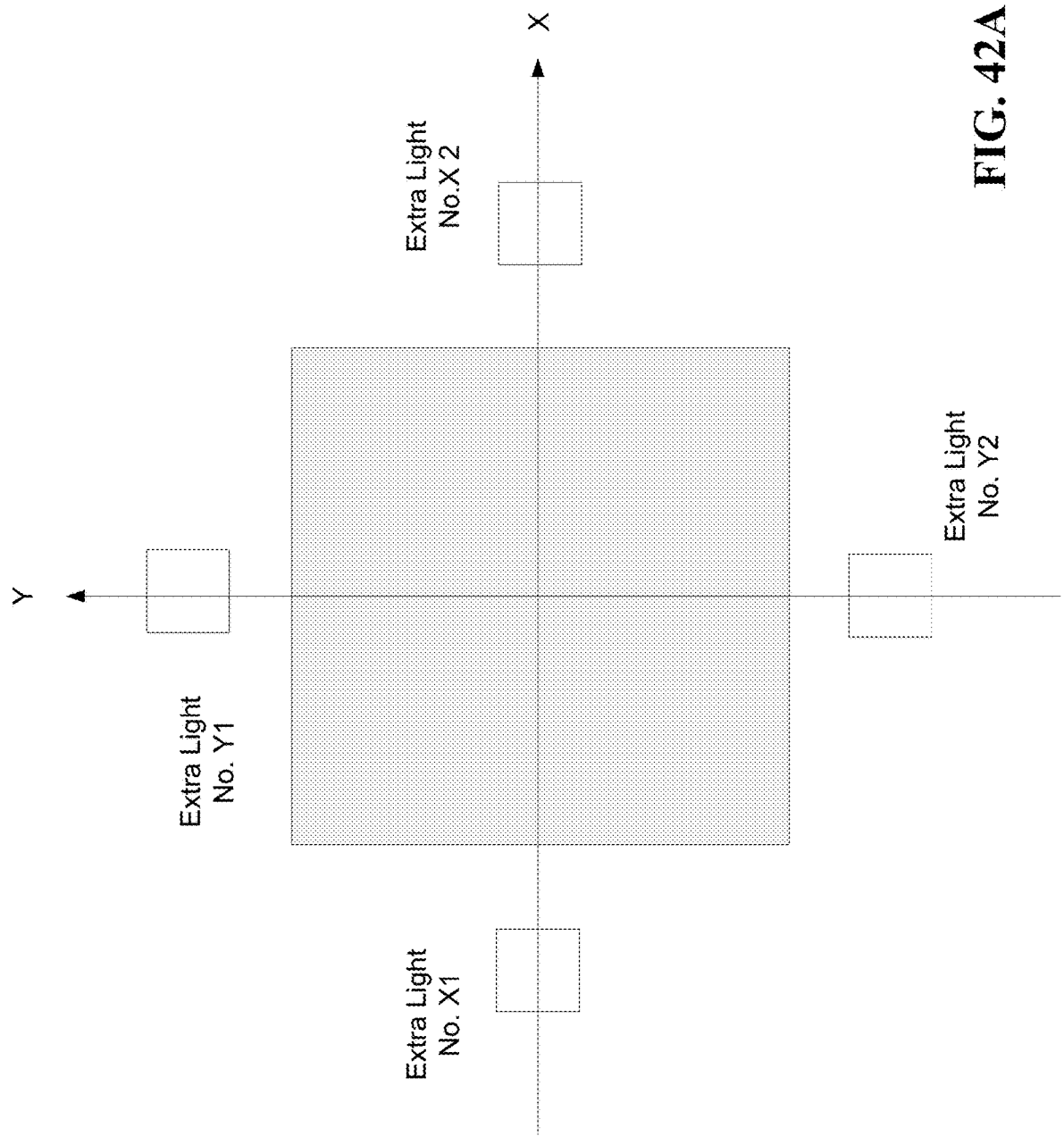

FIG. 42A shows an example for placing 4 extra illumination light sources in two orthogonal directions on opposite sides of the fingerprint sensing area based on the design in FIG. 5D.

FIG. 42B shows that a first illumination probe beam is directed to illuminate a designated fingerprint sensing area over the top transparent layer in a first illumination direction and to enter a user finger over the designated fingerprint sensing area to produce first scattered probe light.

Figure 43:
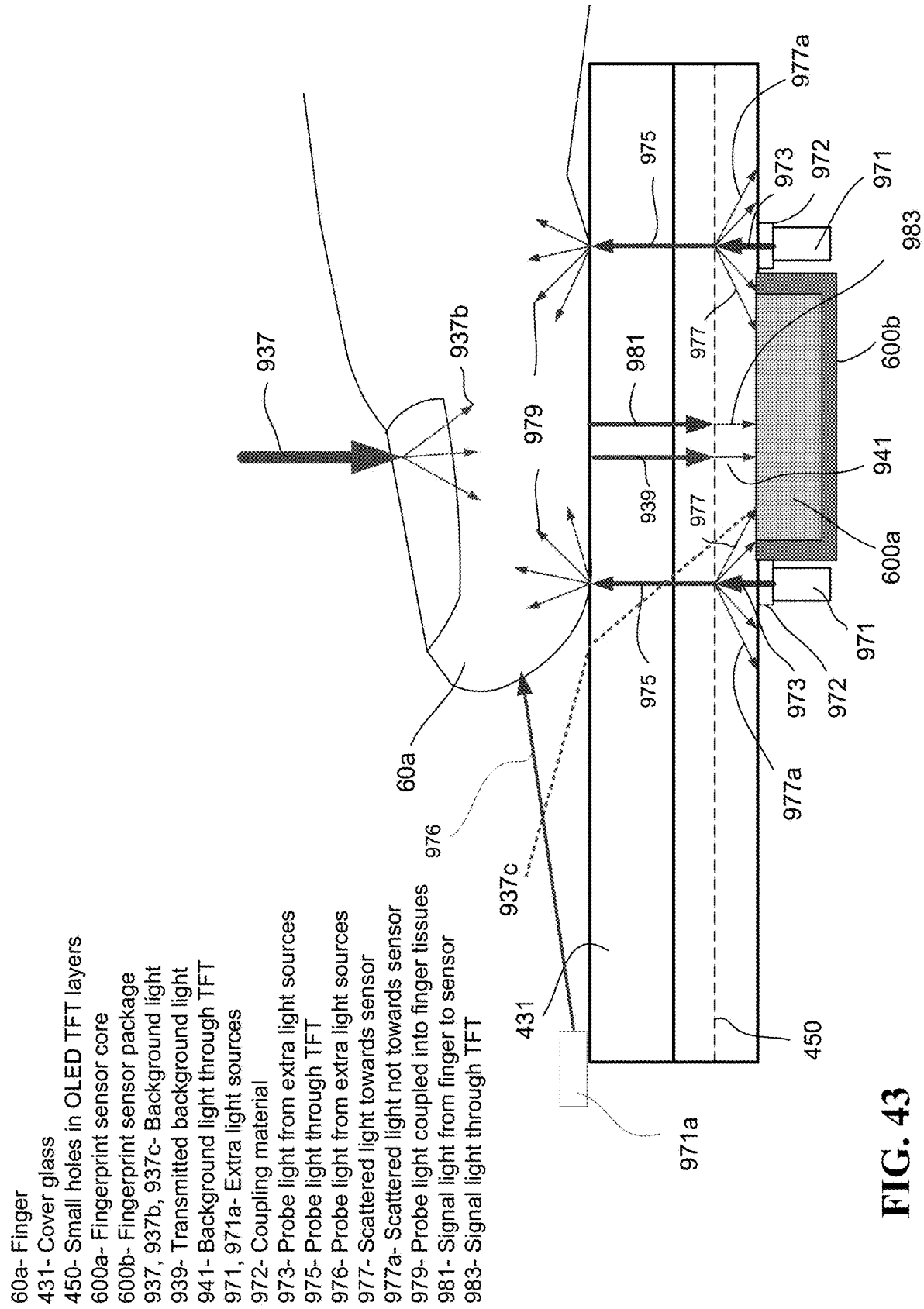

FIG. 43 at least one extra illumination light source is placed above the display panel and the top transparent layer and is away from the designed fingerprint sensing area to direct the illumination beam to the finger in the designated fingerprint sensing area above the top transparent layer to enter the finger and to cause scattering inside the finger which contributes to the part of the signal with an optical transmissive pattern for the optical fingerprint sensing.

FIG. 44 at least one extra illumination light source is placed below the top transparent layer and is away from the designed fingerprint sensing area to direct the illumination beam to one side of the finger in the designated fingerprint sensing area above the top transparent layer to enter the finger and to cause scattering inside the finger which contributes to the part of the signal with an optical transmissive pattern for the optical fingerprint sensing.

Figure 45:
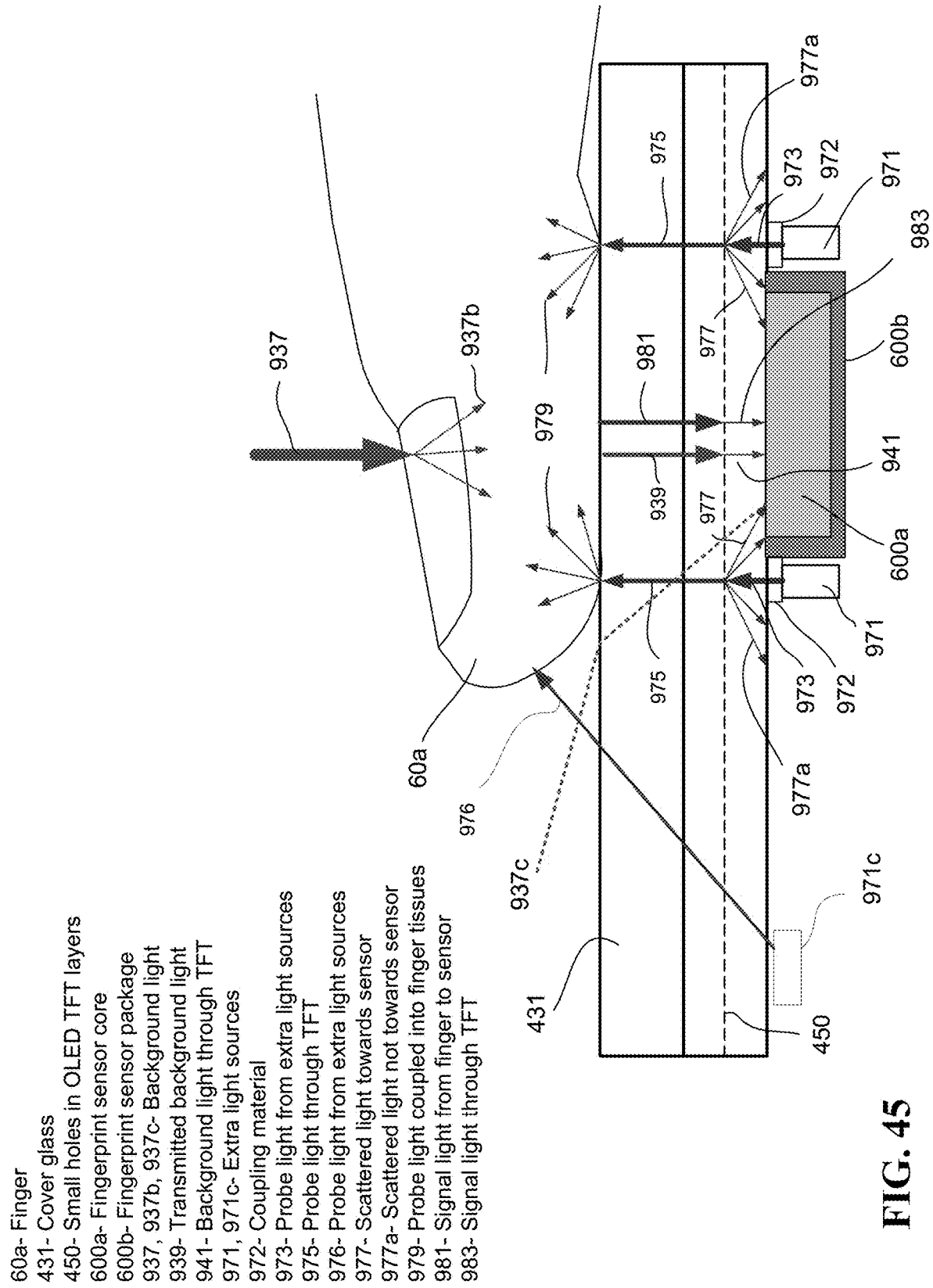

FIG. 45 at least one extra illumination light source is placed below the display panel and is away from the designed fingerprint sensing area to direct the illumination beam to one side of the finger in the designated fingerprint sensing area above the top transparent layer to enter the finger and to cause scattering inside the finger which contributes to the part of the signal with an optical transmissive pattern for the optical fingerprint sensing.

Figure 46:
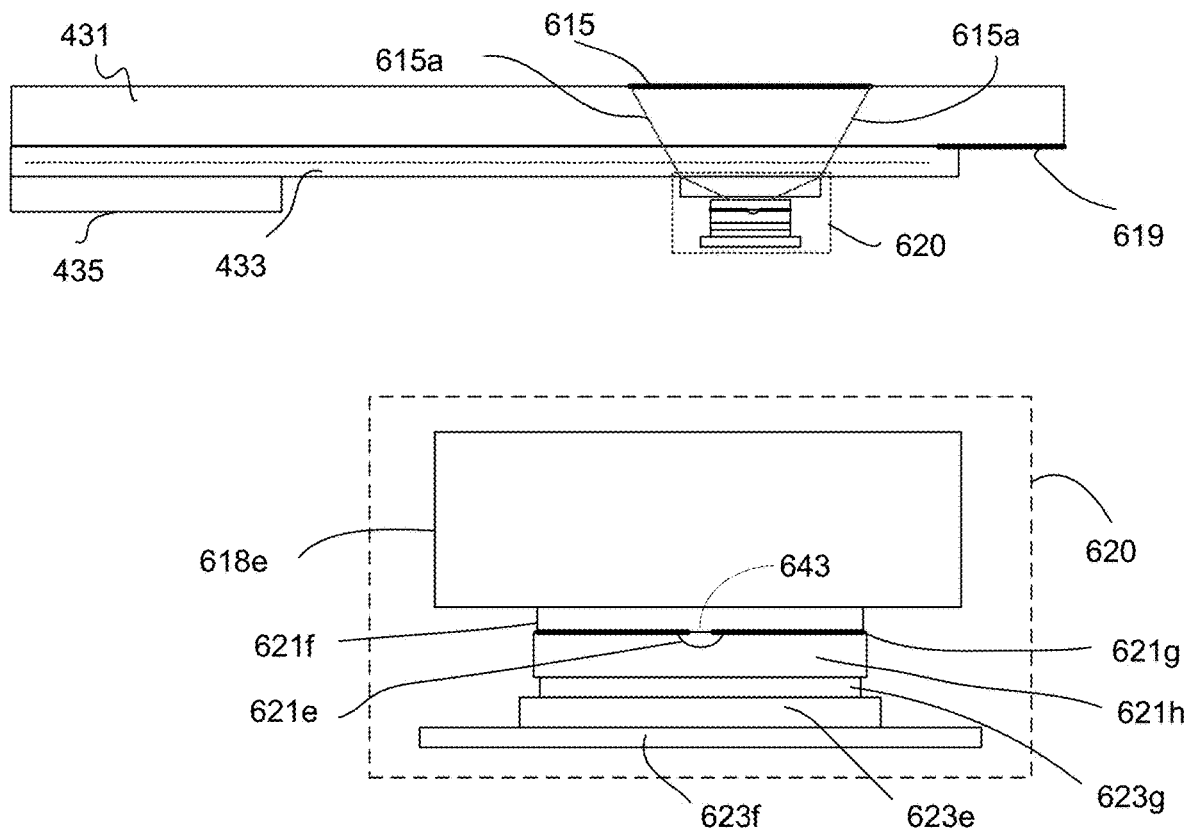

FIG. 46 shows an example of an under-screen optical sensor module based on a pinhole-lens assembly.

FIG. 47 shows an example of an under-screen optical sensor module based on a pinhole-lens assembly with matching material layers on the object side and imaging side of the pinhole-lens assembly.

FIGS. 48A and 48B show imaging operations of a pinhole camera and a pinhole-lens assembly to illustrate the improved spatial imaging resolution due to presence of a lens in the pinhole-lens assembly. The numerals in FIGS. 48A and 48B are used to represent the following:

661, 663—Light beam from an object;
621$f$—Substrate of the pinhole;
667—Image plane;
643—Pinhole;
673—Diverging light beam;
621$e$—Micro lens;
677—Converging light beam;
679—Image spot of a pinhole; and
681—Image spot of a pinhole+micro lens.

FIG. 49 shows imaging of a pinhole-lens assembly to illustrate the reduced image distortions due to presence of a high-index layer for supporting the pinhole located above the pinhole-lens assembly.

Figure 50:
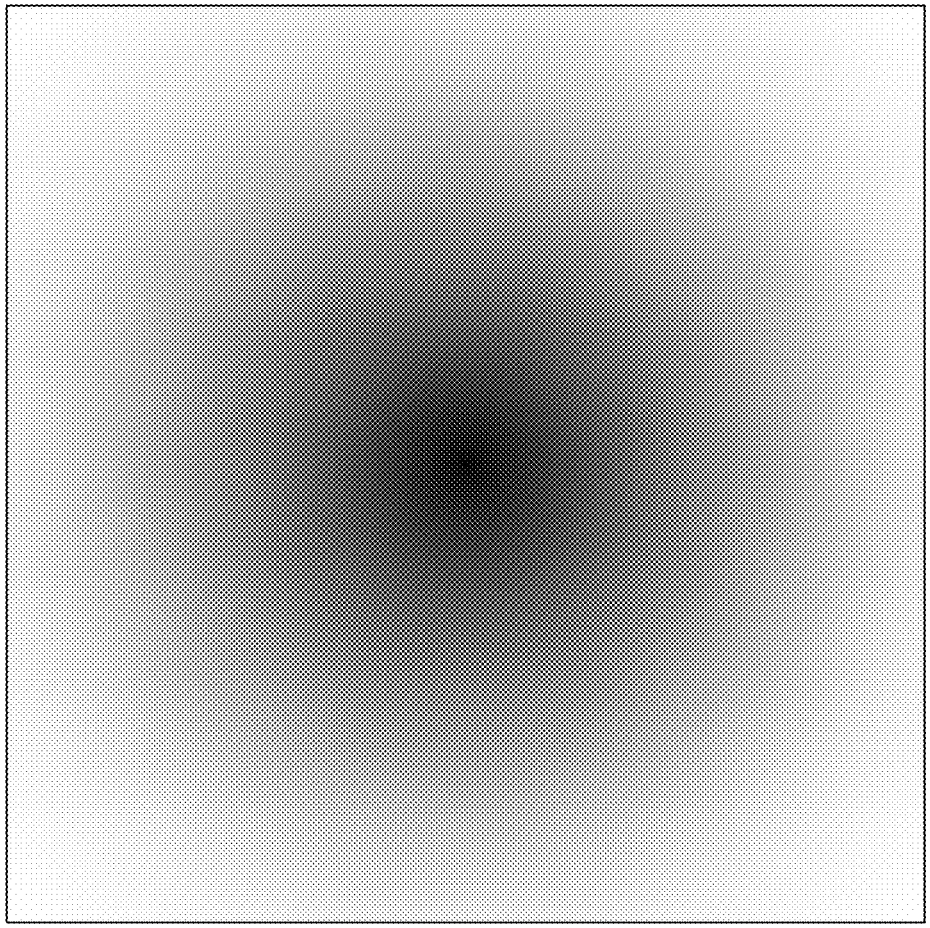

FIG. 50 shows an example of a gradient transmission filter profile for an optical filter used in an under-screen optical sensor module based on a pinhole-lens assembly to improve the image uniformity.

Figure 51:
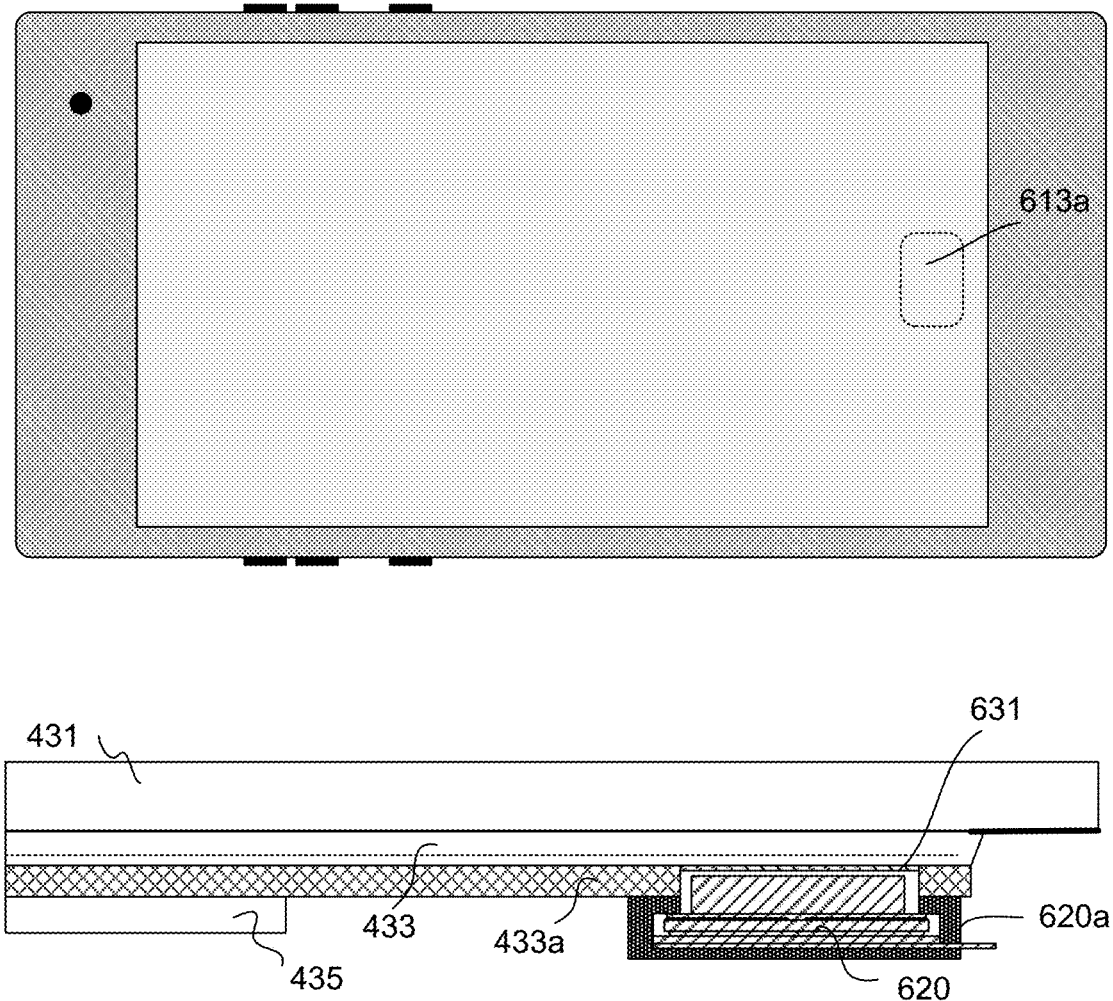

FIG. 51 shows an example of an under-screen optical sensor module based on a pinhole-lens assembly that uses a housing to block the environmental light.

DETAILED DESCRIPTION

Electronic devices or systems may be equipped with fingerprint authentication mechanisms to improve the security for accessing the devices. Such electronic devices or system may include, portable or mobile computing devices, e.g., smartphones, tablet computers, wrist-worn devices and other wearable or portable devices, larger electronic devices or systems, e.g., personal computers in portable forms or desktop forms, ATMs, various terminals to various electronic systems, databases, or information systems for commercial or governmental uses, motorized transportation systems including automobiles, boats, trains, aircraft and others.

Fingerprint sensing is useful in mobile applications and other applications that use or require secure access. For example, fingerprint sensing can be used to provide secure access to a mobile device and secure financial transactions including online purchases. It is desirable to include robust and reliable fingerprint sensing suitable for mobile devices and other applications. In mobile, portable or wearable devices, it is desirable for fingerprint sensors to minimize or eliminate the footprint for fingerprint sensing given the limited space on those devices, especially considering the demands for a maximum display area on a given device.

The disclosed devices or systems in this patent document use optical sensing techniques to perform optical fingerprint sensing and other optical sensing operations. Notably, the optical sensing disclosed in this patent document can be used to optically capture a 2-dimensional spatial pattern of external ridges and valleys of a fingerprint or the internal fingerprint pattern and the topographical information of the internal fingerprint pattern that are associated with the external ridges and valleys of a finger under the finger skin. The internal fingerprint pattern and the topographical information of the internal fingerprint pattern are not just 2-dimensional pattern but also contain spatial information are 3-dimensional in nature due to the spatial variations in the internal tissues below the skin that support and give rise to the external ridges and valleys.

Overview of Disclosed Optical Sensing

The light produced by a display screen for displaying images can pass through the top surface of the display screen in order to be viewed by a user. A finger can touch the top surface and thus interacts with the light at the top surface to cause the reflected or scattered light at the surface area of the touch to carry spatial image information of the finger to return to the display panel underneath the top surface. In touch sensing display devices, the top surface is the touch sensing interface with the user and this interaction between the light for displaying images and the user finger or hand constantly occurs but such information-carrying light returning back to the display panel is largely wasted and is not used in most touch sensing devices. In various mobile or portable devices with touch sensing displays and fingerprint sensing functions, a fingerprint sensor tends to be a separate device from the display screen, either placed on the same surface of the display screen at a location outside the display screen area such as in the popular Apple iPhones and Samsung Galaxy smartphones, or placed on the backside of a smartphone, such as some new models of smart phones by Huawei, Lenovo, Xiaomi or Google, to avoid taking up valuable space for placing a large display screen on the front side. Those fingerprint sensors are separate devices from the display screens and thus need to be compact to save space for display and other functions while still providing reliable and fast fingerprint sensing with a spatial image resolution above a certain acceptable level. However, the need to be compact and small and the need to provide a high spatial image resolution in capturing a fingerprint pattern are in direct conflict with each other in many fingerprint sensors because a high spatial image resolution in capturing a fingerprint pattern in based on various suitable fingerprint sensing technologies (e.g., capacitive touch sensing or optical imaging) requires a large sensor area with a large number of sensing pixels.

The optical sensor technology disclosed herein uses the light for displaying images in a display screen that is returned from the top surface of the device display assembly for fingerprint sensing and other sensing operations. The returned light carries information of an object in touch with the top surface (e.g., a finger) and the capturing and detecting this returned light constitute part of the design considerations in implementing a particular optical sensor module located underneath the display screen. Because the top surface of the touch screen assembly is used as a fingerprint sensing area, the optical image of this touched area should be captured by an optical imaging sensor array inside the optical sensor module with a high image fidelity to the original fingerprint for robust fingerprint sensing. The optical sensor module can be designed to achieve this desired optical imaging by properly configuring optical elements for capturing and detecting the returned light.

The disclosed technology can be implemented to provide devices, systems, and techniques that perform optical sensing of human fingerprints and authentication for authenticating an access attempt to a locked computer-controlled device such as a mobile device or a computer-controlled system, that is equipped with a fingerprint detection module. The disclosed technology can be used for securing access to various electronic devices and systems, including portable or mobile computing devices such as laptops, tablets, smartphones, and gaming devices, and other electronic devices or systems such as electronic databases, automobiles, bank ATMs, etc.

The optical sensor technology disclosed here can be implemented to detect a portion of the light that is used for displaying images in a display screen where such a portion of the light for the display screen may be the scattered light, reflected light or some stray light. For example, in some implementations of the disclosed optical sensor technology for an OLED display screen or another display screen having light emitting display pixels without using backlight, the image light produced by the OLED display screen, at or near the OLED display screen's top surface, may be reflected or scattered back into the OLED display screen as returned light when encountering an object such as a user finger or palm, or a user pointer device like a stylus. Such returned light can be captured for performing one or more optical sensing operations using the disclosed optical sensor technology. Due to the use of the light from OLED display screen's own OLED pixels for optical sensing, an optical sensor module based on the disclosed optical sensor technology can be, in some implementations, specially designed to be integrated to the OLED display screen in a way that maintains the display operations and functions of the OLED display screen without interference while providing optical sensing operations and functions to enhance overall functionality, device integration and user experience of the electronic device such as a smart phone or other mobile/wearable device or other forms of electronic devices or systems.

For example, an optical sensor module based on the disclosed optical sensor technology can be coupled to a display screen having light emitting display pixels without using backlight (e.g., an OLED display screen) to sense a fingerprint of a person by using the above described returned light from the light produced by OLED display screen. In operation, a person's finger, either in direct touch with the OLED display screen or in a near proximity of the OLED display screen, can produce the returned light back into the OLED display screen while carrying information of a portion of the finger illuminated by the light output by the OLED display screen. Such information may include, e.g., the spatial pattern and locations of the ridges and valleys of the illuminated portion of the finger. Accordingly, the optical sensor module can be integrated to capture at least a portion of such returned light to detect the spatial pattern and locations of the ridges and valleys of the illuminated portion of the finger by optical imaging and optical detection operations. The detected spatial pattern and locations of the ridges and valleys of the illuminated portion of the finger can then be processed to construct a fingerprint pattern and to perform fingerprint identification, e.g., comparing with a stored authorized user fingerprint pattern to determine whether the detected fingerprint is a match as part of a user authentication and device access process. This optical sensing based fingerprint detection by using the disclosed optical sensor technology uses the OLED display screens as an optical sensing platform and can be used to replace existing capacitive fingerprint sensors or other fingerprint sensors that are basically self-contained sensors as "add-on" components without using light from display screens or using the display screens for fingerprint sensing for mobile phones, tablets and other electronic devices.

The disclosed optical sensor technology can be implemented in ways that use a display screen having light emitting display pixels (e.g., an OLED display screen) as an optical sensing platform by using the light emitted from the display pixels of the OLED display screens for performing fingerprint sensing or other optical sensing functions after such emitted light interacts with an area on the top touch surface touched by a finger. This intimate relationship between the disclosed optical sensor technology and the OLED display screen provides a unique opportunity for using an optical sensor module to provide both (1) additional optical sensing functions and (2) useful operations or control features in connection with the touch sensing aspect of the OLED display screen.

Notably, in some implementations, an optical sensor module based on the disclosed optical sensor technology can be coupled to the backside of the OLED display screen without requiring a designated area on the display surface side of the OLED display screen that would occupy a valuable device surface real estate in some electronic devices such as a smartphone, a tablet or a wearable device where the exterior surface area is limited. Such an optical sensor module can be placed under the OLED display screen that vertically overlaps with the display screen area, and, from the user's perspective, the optical sensor module is hidden behind the display screen area. In addition, because the optical sensing of such an optical sensor module is by detecting the light that is emitted by the OLED display screen and is returned from the top surface of the display area, the disclosed optical sensor module does not require a special sensing port or sensing area that is separate from the display screen area. Accordingly, different from fingerprint sensors in other designs, including, e.g., Apple's iPhone/iPad devices or Samsung Galaxy smartphone models where the fingerprint sensor is located at a particular fingerprint sensor area or port (e.g., the home button) on the same surface of the display screen but located in a designated non-displaying zone that is outside the display screen area, the optical sensor module based on the disclosed optical sensor technology can be implemented in ways that would allow fingerprint sensing to be performed at a location on the OLED display screen by using unique optical sensing designs to route the returned light from the finger into an optical sensor and by providing proper optical imaging mechanism to achieve high resolution optical imaging sensing. In this regard, the disclosed optical sensor technology can be implemented to provide a unique on-screen fingerprint sensing configuration by using the same top touch sensing surface that displays images and provides the touch sensing operations without a separate fingerprint sensing area or port outside the display screen area.

Regarding the additional optical sensing functions beyond fingerprint detection, the optical sensing may be used to measure other parameters. For example, the disclosed optical sensor technology can measure a pattern of a palm of a person given the large touch area available over the entire OLED display screen (in contrast, some designated fingerprint sensors such as the fingerprint sensor in the home button of Apple's iPhone/iPad devices have a rather small and designated off-screen fingerprint sensing area that is highly limited in the sensing area size that may not be suitable for sensing large patterns). For yet another example, the disclosed optical sensor technology can be used not only to use optical sensing to capture and detect a pattern of a finger or palm that is associated with a person, but also to use optical sensing or other sensing mechanisms to detect whether the captured or detected pattern of a fingerprint or palm is from a live person's hand by a "live finger" detection mechanism, which may be based on, for example, the different optical absorption behaviors of the blood at different optical wavelengths, the fact that a live person's finger tends to be moving or stretching due to the person's natural movement or motion (either intended or unintended) or pulsing when the blood flows through the person's body in connection with the heartbeat. In one implementation, the optical sensor module can detect a change in the returned light from a finger or palm due to the heartbeat/blood flow change and thus to detect whether there is a live heartbeat in the object presented as a finger or palm. The user authentication can be based on the combination of the both the optical sensing of the fingerprint/palm pattern and the positive determination of the presence of a live person to enhance the access control. For yet another example, the optical sensor module may include a sensing function for measuring a glucose level or a degree of oxygen saturation based on optical sensing in the returned light from a finger or palm. As yet another example, as a person touches the OLED display screen, a change in the touching force can be reflected in one or more ways, including fingerprint pattern deforming, a change in the contacting area between the finger and the screen surface, fingerprint ridge widening, or a blood flow dynamics change. Those and other changes can be measured by optical sensing based on the disclosed optical sensor technology and can be used to calculate the touch force. This touch force sensing can be used to add more functions to the optical sensor module beyond the fingerprint sensing.

With respect to useful operations or control features in connection with the touch sensing aspect of the OLED display screen, the disclosed optical sensor technology can provide triggering functions or additional functions based on one or more sensing results from the optical sensor module to perform certain operations in connection with the touch sensing control over the OLED display screen. For example, the optical property of a finger skin (e.g., the index of refraction) tends to be different from other artificial objects. Based on this, the optical sensor module may be designed to selectively receive and detect returned light that is caused by a finger in touch with the surface of the OLED display screen while returned light caused by other objects would not be detected by the optical sensor module. This object-selective optical detection can be used to provide useful user controls by touch sensing, such as waking up the smartphone or device only by a touch via a person's finger or palm while touches by other objects would not cause the device to wake up for energy efficient operations and to prolong the battery use. This operation can be implemented by a control based on the output of the optical sensor module to control the waking up circuitry operation of the OLED display screen which, most of the OLED pixels are put in a "sleep" mode by being turned off without emitting light while part of the OLED pixels in the OLED display screen are turned on in a flash mode to intermittently emit flash light to the screen surface for sensing any touch by a person's finger or palm. Another "sleep" mode configuration can be achieved by using one or more extra LED light sources built into the optical sensor module to produce the "sleep" mode wake-up sensing light flashes where all the OLED pixels are turned off during the sleep mode so that the optical sensor module can detect returned light of such wake-up sensing light caused by the finger touch on the OLED display screen and, upon a positive detection, the OLED pixels on the OLED display screen are turned on or "woken up". In some implementations, the wake-up sensing light can be in the infrared invisible spectral range so a user will not experience any visual of a flash light. For another example, the fingerprint sensing by the optical sensor module is based on sensing of the returned light from the surface of the OLED display screen in the course of the normal OLED display screen operation, the OLED display screen operation can be controlled to provide an improved fingerprint sensing by eliminating background light for optical sensing of the fingerprint. In one implementation, for example, each display scan frame generates a frame of fingerprint signals. If, two frames of fingerprint signals with the display are generated in one frame when the OLED display screen is turned on and in the other frame when the OLED display screen is turned off, the subtraction between those two frames of signals can be used to reduce the ambient background light influence. By operating the fingerprint sensing frame rate is at one half of the display frame rate in some implementations, the background light noise in fingerprint sensing can be reduced.

As discussed above, an optical sensor module based on the disclosed optical sensor technology can be coupled to the backside of the OLED display screen without requiring creation of a designated area on the surface side of the OLED display screen that would occupy a valuable device surface real estate in some electronic devices such as a smartphone, a tablet or a wearable device. This aspect of the disclosed technology can be used to provide certain advantages or benefits in both device designs and product integration or manufacturing.

In some implementations, an optical sensor module based on the disclosed optical sensor technology can be configured as a non-invasive module that can be easily integrated to a display screen having light emitting display pixels (e.g., an OLED display screen) without requiring changing the design of the OLED display screen for providing a desired optical sensing function such as fingerprint sensing. In this regard, an optical sensor module based on the disclosed optical sensor technology can be independent from the design of a particular OLED display screen design due to the nature of the optical sensor module: the optical sensing of such an optical sensor module is by detecting the light that is emitted by the OLED display screen and is returned from the top surface of the display area, and the disclosed optical sensor module is coupled to the backside of the OLED display screen as a under-screen optical sensor module for receiving the returned light from the top surface of the display area and thus does not require a special sensing port or sensing area that is separate from the display screen area. Accordingly, such a under-screen optical sensor module can be used to combine with OLED display screens to provide optical fingerprint sensing and other sensor functions on an OLED display screen without using a specially designed OLED display screen with hardware especially designed for providing such optical sensing. This aspect of the disclosed optical sensor technology enables a wide range of OLED display screens in smartphones, tablets or other electronic devices with enhanced functions from the optical sensing of the disclosed optical sensor technology.

For example, for an existing phone assembly design that does not provide a separate fingerprint sensor as in certain Apple iPhones or Samsung Galaxy models, such an existing phone assembly design can integrate the under-screen optical sensor module as disclosed herein without changing the touch sensing-display screen assembly to provide an added on-screen fingerprint sensing function. Because the disclosed optical sensing does not require a separate designated sensing area or port as in the case of certain Apple iPhones/Samsung Galaxy phones with a front fingerprint sensor outside the display screen area, or some smartphones with a designated rear fingerprint sensor on the backside like in some models by Huawei, Xiaomi, Google or Lenovo, the integration of the on-screen fingerprint sensing disclosed herein does not require a substantial change to the existing phone assembly design or the touch sensing display module that has both the touch sensing layers and the display layers. Based on the disclosed optical sensing technology in this document, no external sensing port and no extern hardware button are needed on the exterior of a device are needed for adding the disclosed optical sensor module for fingerprint sensing. The added optical sensor module and the related circuitry are under the display screen inside the phone housing and the fingerprint sensing can be conveniently performed on the same touch sensing surface for the touch screen.

For another example, due to the above described nature of the optical sensor module for fingerprint sensing, a smartphone that integrates such an optical sensor module can be updated with improved designs, functions and integration mechanism without affecting or burdening the design or manufacturing of the OLED display screens to provide desired flexibility to device manufacturing and improvements/upgrades in product cycles while maintaining the availability of newer versions of optical sensing functions to smartphones, tablets or other electronic devices using OLED display screens. Specifically, the touch sensing layers or the OLED display layers may be updated in the next product release without adding any significant hardware change for the fingerprint sensing feature using the disclosed under-screen optical sensor module. Also, improved on-screen optical sensing for fingerprint sensing or other optical sensing functions by such an optical sensor module can be added to a new product release by using a new version of the under-screen optical sensor module without requiring significant changes to the phone assembly designs, including adding additional optical sensing functions.

The above and other features of the disclosed optical sensor technology can be implemented to provide a new generation of electronic devices with improved fingerprint sensing and other sensing functions, especially for smartphones, tablets and other electronic devices with display screens having light emitting display pixels without using backlight (e.g., an OLED display screen) to provide various touch sensing operations and functions and to enhance the user experience in such devices.

In practical applications, the performance of optical sensing for fingerprint sensing and other sensing functions in an electronic device equipped with optical fingerprint sensing may be degraded by the presence of undesired background light from the environment where a portion of the background light may enter the optical sensor module. Such background light causes the optical detectors in the optical sensor module to produce a noise signal that undesirable reduces the signal to noise ratio of the optical fingerprint sensing detection. In some conditions, such background noise can be high to a degree that may overwhelm the signal level of the useful signal that carries the optical fingerprint information or other useful information (e.g., biometric information) and could potentially cause unreliable optical sensing operation or even malfunction of the optical sensing. For example, one of sources for the undesired background light at the optical sensor module may be from the daylight from the sun and the impact of the sunlight can be particularly problematic for outdoor operations or in a sheltered environment with strong sunlight. For another example, other light sources present at locations at or near the location of the device with the disclosed optical fingerprint sensing may also lead to the undesired background light at the optical sensor module.

The undesired impact of the background light at the optical sensor module may be mitigated by reducing the amount of the undesired background light that can enter the optical sensor module, enhancing the optical signal level of the optical sensing signal carrying the fingerprint or other useful information beyond the signal level by using the returned OLED display light, or a combination of both background reduction and enhancing optical sensing signal level. In implementations, the background reduction can be achieved by using one or more optical filtering mechanisms in connection with the under-screen optical sensor module. In enhancing the optical signal level of the optical sensing signal carrying the fingerprint or other useful information, one or more extra illumination light sources may be added to the device to provide additional optical illumination light beyond the signal level caused by the returned OLED display light.

Using extra illumination light sources for optical fingerprint sensing and other optical sensing functions can also provide independent control over various features in providing illumination light for optical sensing, e.g., the selection of the illumination light wavelengths separate from the OLED display light in terms of the optical transmission property of human tissues, providing illumination for optical sensing operations beyond the spectral range in the OLED display light, controlling the mode of the illumination for optical sensing such as the timing or/and duration of illumination separate from the OLED display light, achieving a sufficiently high illumination level while maintaining an efficient use of power to prolong the battery operating time (an important factor for mobile computing or communication devices), and strategic placing the extra illumination light sources at certain locations to achieve illumination configurations that are difficult or impossible when using the OLED display light for illumination for optical sensing.

In addition, unlike many fingerprint sensing technologies that detect 2-dimensional spatial pattern of a fingerprint, the disclosed optical fingerprint sensing technology can be implemented to capture not only a 2-dimensional spatial pattern of external ridges and valleys of a fingerprint but also internal fingerprint pattern associated with the external ridges and valleys of a finger under the finger skin. The disclosed optical fingerprint sensing by capturing information on the internal fingerprint pattern associated with the external ridges and valleys of a finger under the finger skin is substantially immune from the contact conditions between the finger and the top touch surface of the device (e.g., dirty contact surface) and the conditions of the external finger skin condition (e.g., dirty, dry or wet fingers, or reduced external variations between ridges and valleys in fingers of certain users such as aged users).

In implementations of the disclosed technical features, additional sensing functions or sensing modules, such as a biomedical sensor, e.g., a heartbeat sensor in wearable devices like wrist band devices or watches, may be provided. In general, different sensors can be provided in electronic devices or systems to achieve different sensing operations and functions.

General Architecture of Optical Sensing Module Under Display Panel

Figure 1:
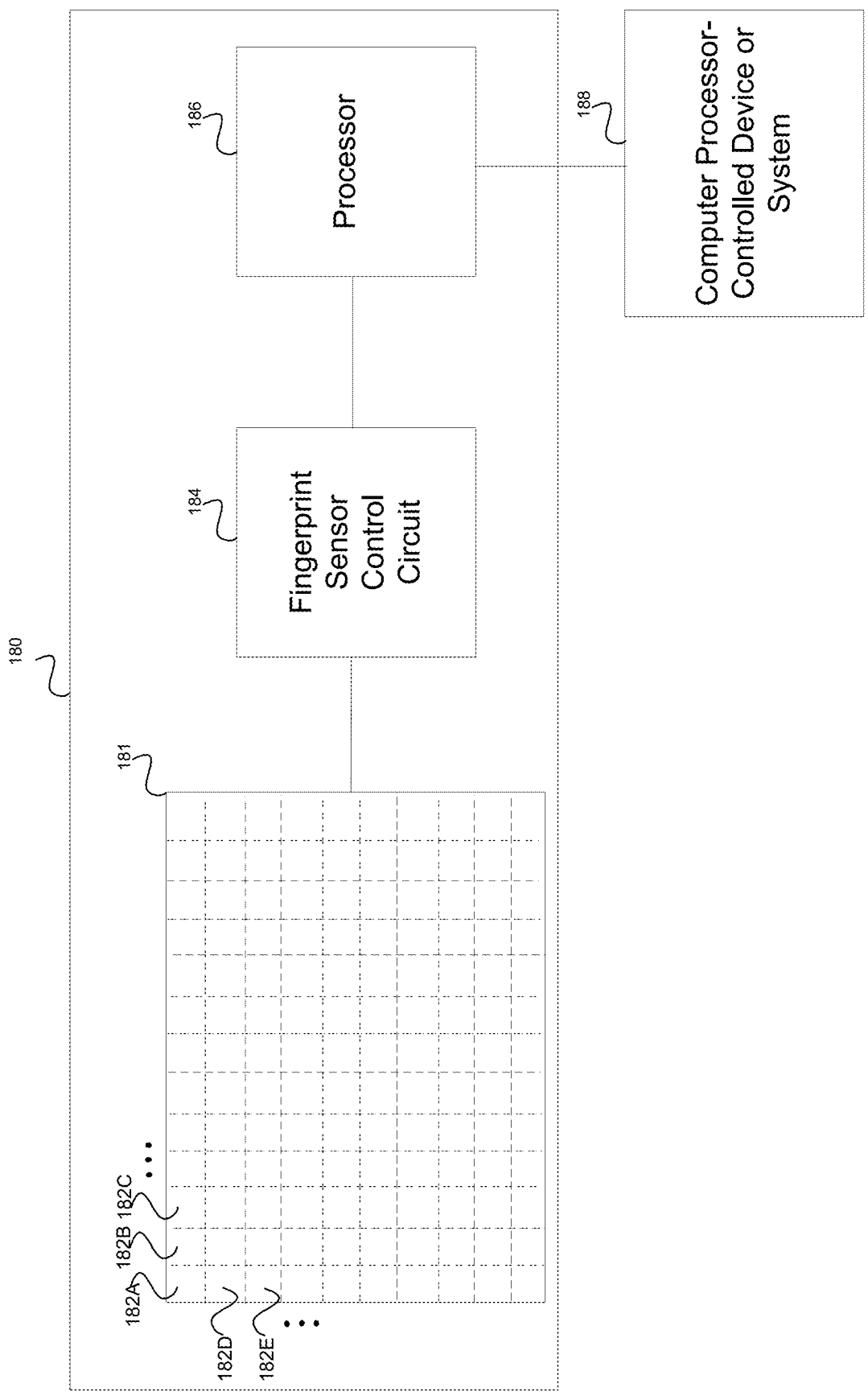
FIG. 1 is a block diagram of an example of a system with a fingerprint sensing module which can be implemented to include an optical fingerprint sensor disclosed in this document.

FIG. 1 is a block diagram of an example of a system 180 with a fingerprint sensing module 180 including a fingerprint sensor 181 which can be implemented to include an optical fingerprint sensor based on the optical sensing of fingerprints as disclosed in this document. The system 180 includes a fingerprint sensor control circuit 184, and a digital processor 186 which may include one or more processors for processing fingerprint patterns and determining whether an input fingerprint pattern is one for an authorized user. The fingerprint sensing system 180 uses the fingerprint sensor 181 to obtain a fingerprint and compares the obtained fingerprint to a stored fingerprint to enable or disable functionality in a device or system 188 that is secured by the fingerprint sensing system 180. In operation, the access to the device 188 is controlled by the fingerprint processing processor 186 based on whether the captured user fingerprint is from an authorized user. As illustrated, the fingerprint sensor 181 may include multiple fingerprint sensing pixels such as pixels 182A-182E that collectively represent at least a portion of a fingerprint. For example, the fingerprint sensing system 180 may be implemented at an ATM as the system 188 to determine the fingerprint of a customer requesting to access funds or other transactions. Based on a comparison of the customer's fingerprint obtained from the fingerprint sensor 181 to one or more stored fingerprints, the fingerprint sensing system 180 may, upon a positive identification, cause the ATM system 188 to grant the requested access to the user account, or, upon a negative identification, may deny the access. For another example, the device or system 188 may be a smartphone or a portable device and the fingerprint sensing system 180 is a module integrated to the device 188. For another example, the device or system 188 may be a gate or secured entrance to a facility or home that uses the fingerprint sensor 181 to grant or deny entrance. For yet another example, the device or system 188 may be an automobile or other vehicle that uses the fingerprint sensor 181 to link to the start of the engine and to identify whether a person is authorized to operate the automobile or vehicle.

Figure 2A:
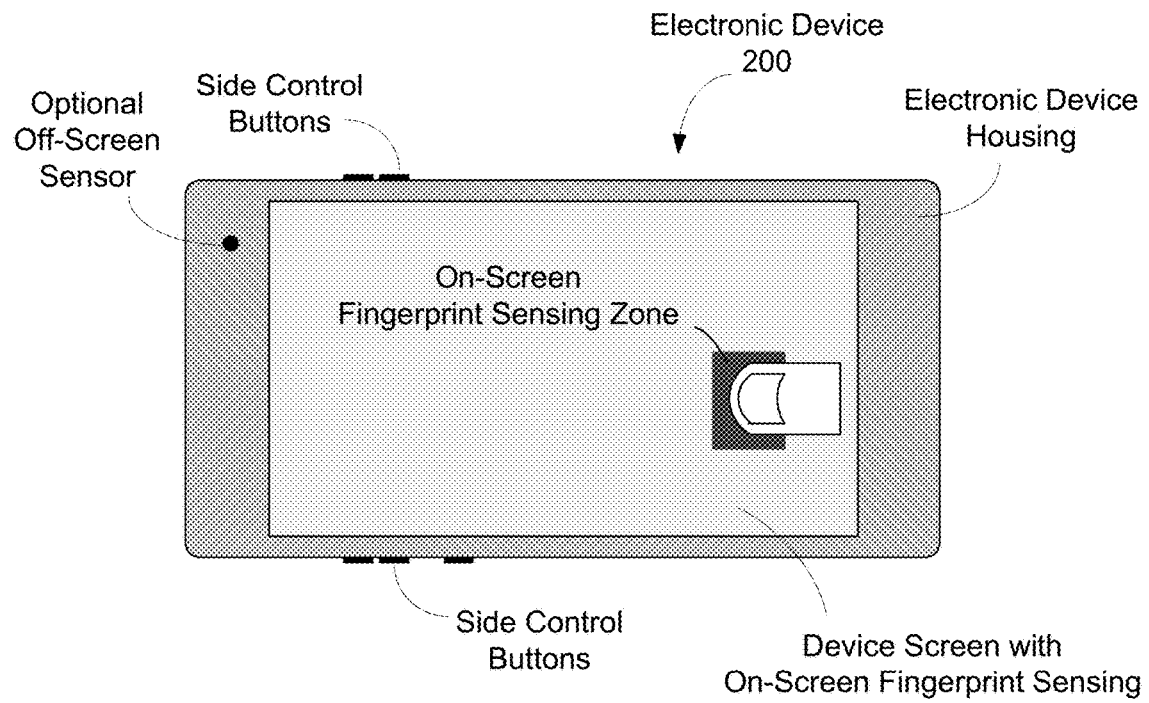
FIGS. 2A and 2B illustrate one exemplary implementation of an electronic device 200 having a touch sensing display screen assembly and an optical sensor module positioned underneath the touch sensing display screen assembly.
Figure 2B:
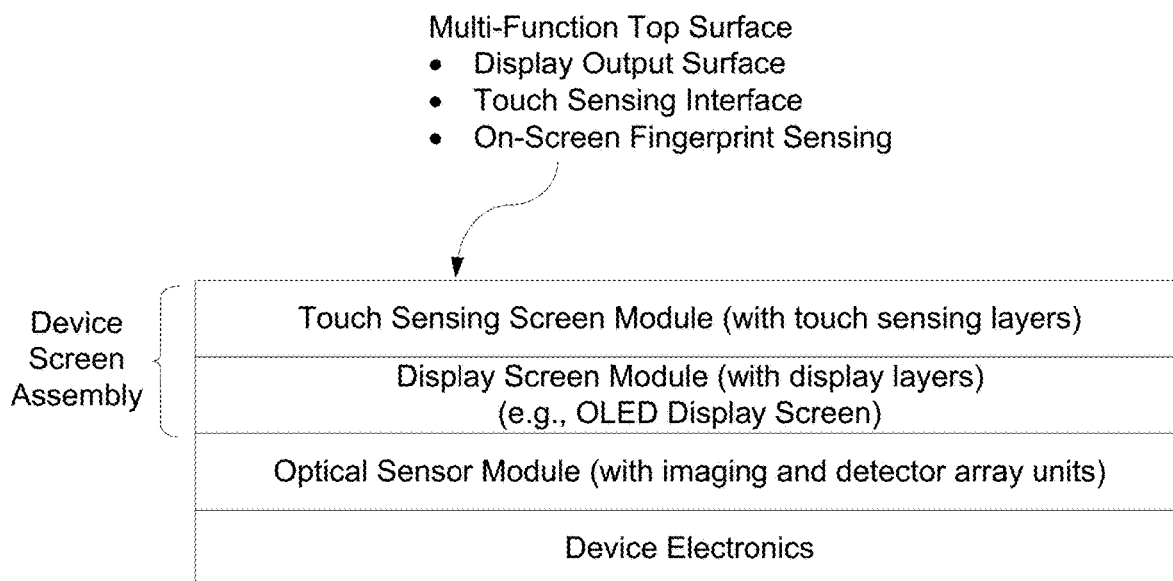

As a specific example, FIGS. 2A and 2B illustrate one exemplary implementation of an electronic device 200 having a touch sensing display screen assembly and an optical sensor module positioned underneath the touch sensing display screen assembly. In this particular example, the display technology can be implemented by an OLED display screen or another display screen having light emitting display pixels without using backlight. The electronic device 200 can be a portable device such as a smartphone or a tablet and can be the device 188 as shown in FIG. 1.

FIG. 2A shows the front side of the device 200 which may resemble some features in some existing smartphones or tablets. The device screen is on the front side of the device 200 occupying either entirety, a majority or a significant portion of the front side space and the fingerprint sensing function is provided on the device screen, e.g., one or more sensing areas for receiving a finger on the device screen. As an example, FIG. 2A shows a fingerprint sensing zone in the device screen for a finger to touch which may be illuminated as a visibly identifiable zone or area for a user to place a finger for fingerprint sensing. Such a fingerprint sensing zone can function like the rest of the device screen for displaying images. As illustrated, the device housing of the device 200 may have, in various implementations, side facets that support side control buttons that are common in various smartphones on the market today. Also, one or more optional sensors may be provided on the front side of the device 200 outside the device screen as illustrated by one example on the left upper corner of the device housing in FIG. 2A.

FIG. 2B shows an example of the structural construction of the modules in the device 200 relevant to the optical fingerprint sensing disclosed in this document. The device screen assembly shown in FIG. 2B includes, e.g., the touch sensing screen module with touch sensing layers on the top, and a display screen module with display layers located underneath the touch sensing screen module. An optical sensor module is coupled to, and located underneath, the display screen assembly module to receive and capture the returned light from the top surface of the touch sensing screen module and to guide and image the returned light onto an optical sensor array of optical sensing pixels or photodetectors which convert the optical image in the returned light into pixel signals for further processing. Underneath the optical sensor module is the device electronics structure containing certain electronic circuits for the optical sensor module and other parts in the device 200. The device electronics may be arranged inside the device housing and may include a part that is under the optical sensor module as shown in FIG. 2B.

In implementations, the top surface of the device screen assembly can be a surface of an optically transparent layer serving as a user touch sensing surface to provide multiple functions, such as (1) a display output surface through which the light carrying the display images passes through to reach a viewer's eyes, (2) a touch sensing interface to receive a user's touches for the touch sensing operations by the touch sensing screen module, and (3) an optical interface for on-screen fingerprint sensing (and possibly one or more other optical sensing functions). This optically transparent layer can be a rigid layer such as a glass or crystal layer or a flexible layer.

One example of a display screen having light emitting display pixels without using backlight is an OLED display having an array of individual emitting pixels, and a thin film transistor (TFT) structure or substrate which may include arrays of small holes and may be optically transparent and a cover substrate to protect the OLED pixels. Referring to FIG. 2B, the optical sensor module in this example is placed under the OLED display panel to capture the returned light from the top touch sensing surface and to acquire high resolution images of fingerprint patterns when user's finger is in touch with a sensing area on the top surface. In other implementations, the disclosed under-screen optical sensor module for fingerprint sensing may be implemented on a device without the touch sensing feature. In addition, a suitable display panel may be in various screen designs different from OLED displays.

Figure 2C:
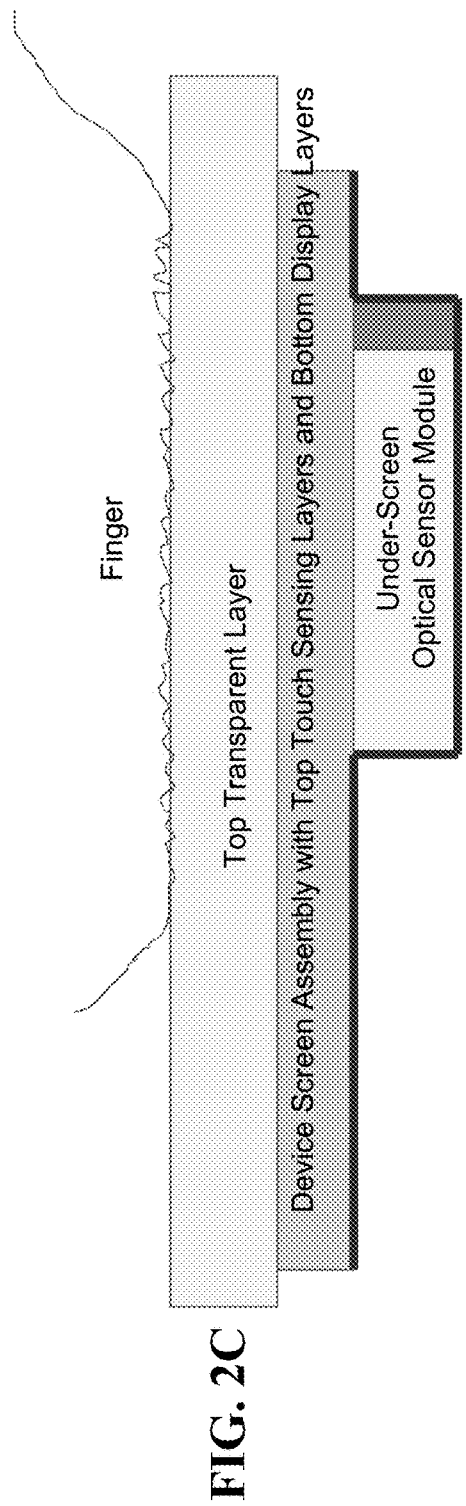
FIGS. 2C and 2D illustrate an example of a device that implements the optical sensor module in FIGS. 2A and 2B.
Figure 2D:
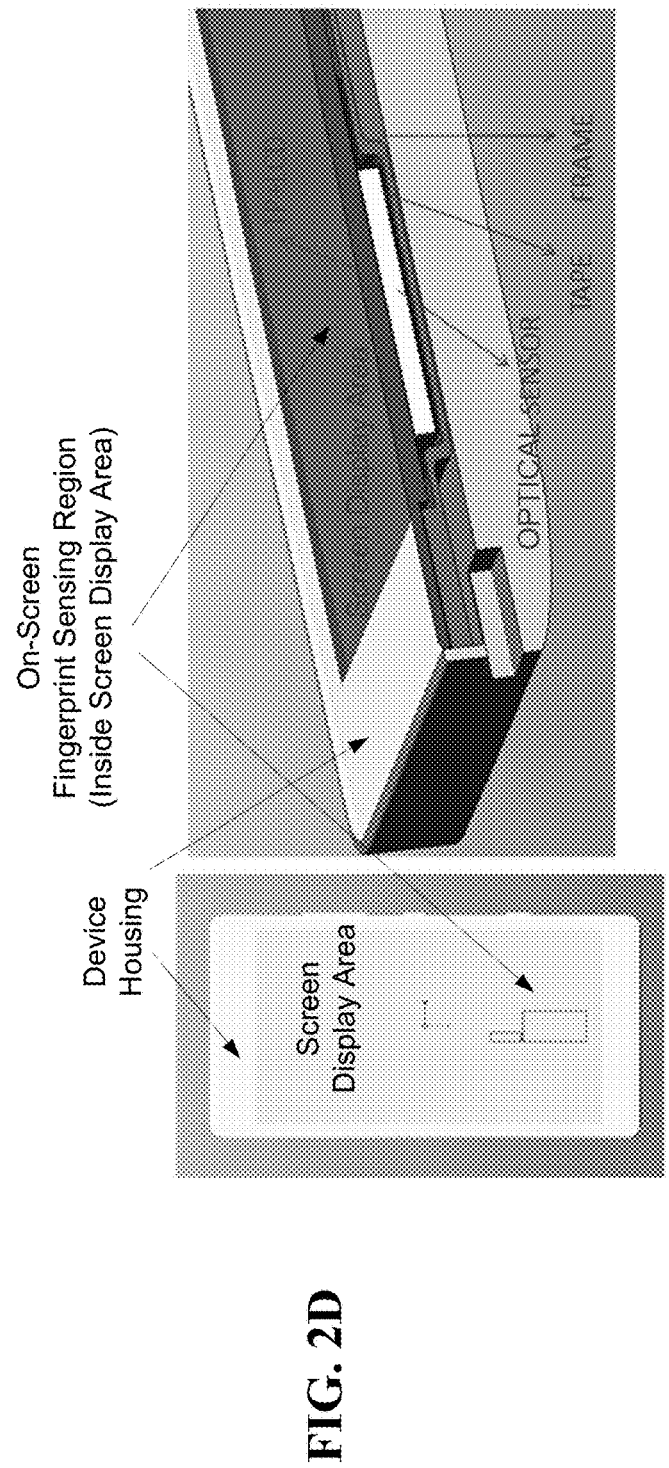

FIGS. 2C and 2D illustrate an example of a device that implements the optical sensor module in FIGS. 2A and 2B. FIG. 2C shows a cross sectional view of a portion of the device containing the under-screen optical sensor module. FIG. 2D shows, on the left, a view of the front side of the device with the touch sensing display indicating a fingerprint sensing area on the lower part of the display screen, and on the right, a perspective view of a part of the device containing the optical sensor module that is under the device display screen assembly. FIG. 2D also shows an example of the layout of the flexible tape with circuit elements.

In the design examples in FIGS. 2A, 2B, 2C and 2D, the optical fingerprint sensor design is different from some other fingerprint sensor designs using a separate fingerprint sensor structure from the display screen with a physical demarcation between the display screen and the fingerprint sensor (e.g., a button like structure in an opening of the top glass cover in some mobile phone designs) on the surface of the mobile device. In the illustrated designs here, the optical fingerprint sensor for detecting fingerprint sensing and other optical signals are located under the top cover glass or layer (e.g., FIG. 2C) so that the top surface of the cover glass serves as the top surface of the mobile device as a contiguous and uniform glass surface across both the display screen layers and the optical detector sensor that are vertically stacked and vertically overlap. This design for integrating optical fingerprint sensing and the touch sensitive display screen under a common and uniform surface provides benefits, including improved device integration, enhanced device packaging, enhanced device resistance to exterior elements, failure and wear and tear, and enhanced user experience over the ownership period of the device.

Figure 3:
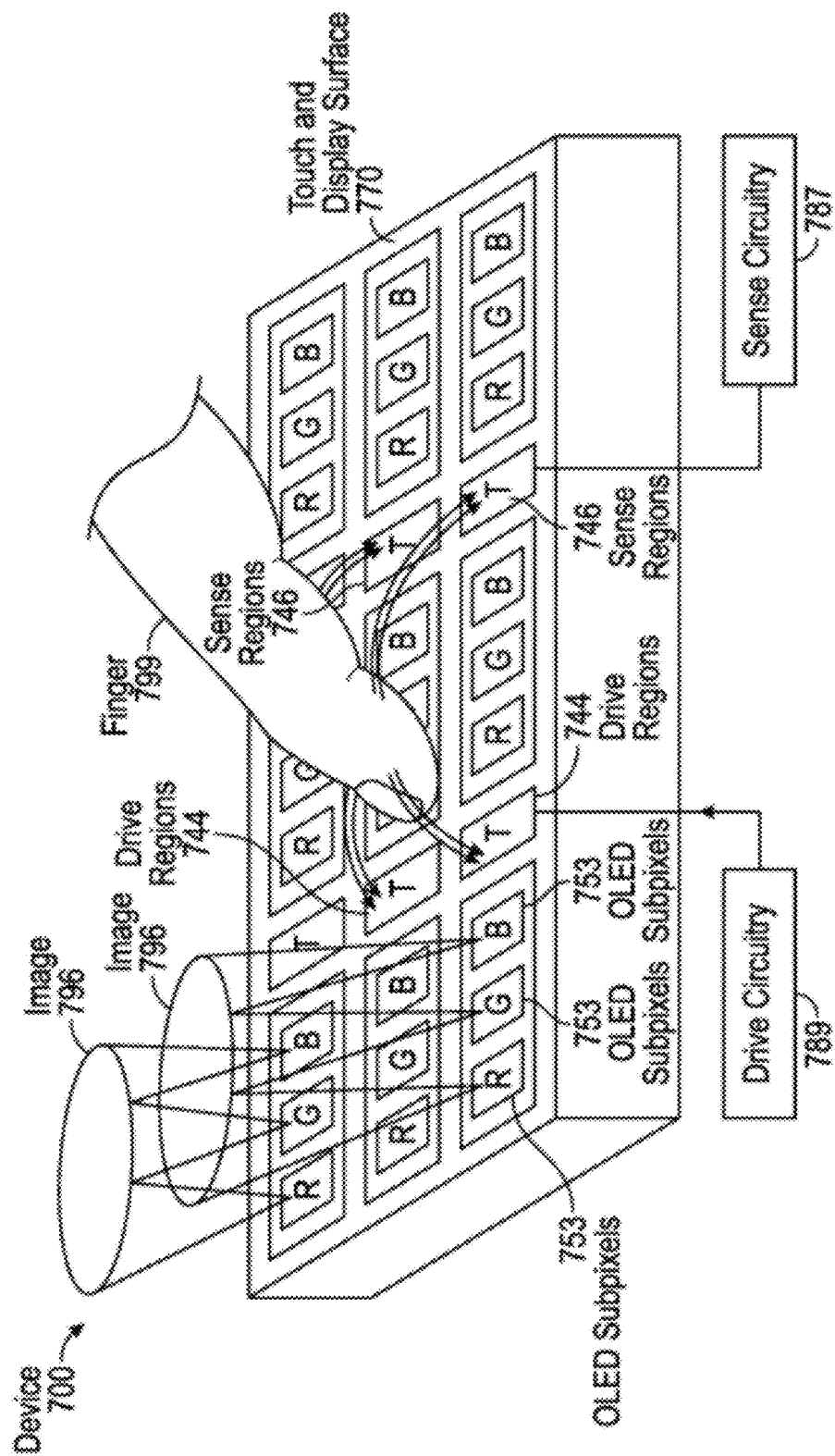
FIG. 3 illustrates one example of an OLED display and touch sensing assembly suitable for implementing the disclosed optical fingerprint sensing technology.

Various OLED display designs and touch sensing designs can be used for the device screen assembly above the optical sensor module in FIGS. 2A, 2B, 2C and 2D. FIG. 3 illustrates one example of an OLED display and touch sensing assembly, which is FIG. 7B of U.S. Patent Publication No. US 2015/0331508 A1 published on Nov. 19, 2015, a patent application entitled "Integrated Silicon-OLED Display and Touch Sensor Panel" by Apple, Inc., which is incorporated by reference as part of the disclosure of this patent document. OLEDs can be implemented in various types or configurations, including, but not limited to, passive-matrix OLEDs (PMOLEDs), active-matrix OLEDs (AMOLEDs), transparent OLEDs, cathode-common OLEDs, anode-common OLEDs, White OLEDs (WOLEDs), and RGB-OLEDs. The different types of OLEDs can have different uses, configurations, and advantages. In the example of a system having an integrated Silicon-OLED display and touch sensor panel, the system can include a Silicon substrate, an array of transistors, one or more metallization layers, one or more vias, an OLED stack, color filters, touch sensors, and additional components and circuitry. Additional components and circuitry can include an electrostatic discharge device, a light shielding, a switching matrix, one or more photodiodes, a near-infrared detector and near-infrared color filters. The integrated Silicon-OLED display and touch sensor panel can be further configured for near-field imaging, optically-assisted touch, and fingerprint detection. In some examples, a plurality of touch sensors and/or display pixels can be grouped into clusters, and the clusters can be coupled to a switching matrix for dynamic change of touch and/or display granularity. In the OLED example in FIG. 3 and other implementations, touch sensors and touch sensing circuitry can include, for example, touch signal lines, such as drive lines and sense lines, grounding regions, and other circuitry. One way to reduce the size of an integrated touch screen can be to include multi-function circuit elements that can form part of the display circuitry designed to operate as circuitry of the display system to generate an image on the display. The multi-function circuit elements can also form part of the touch sensing circuitry of a touch sensing system that can sense one or more touches on or near the display. The multi-function circuit elements can be, for example, capacitors in display pixels of an LCD that can be configured to operate as storage capacitors/electrodes, common electrodes, conductive wires/pathways, etc., of the display circuitry in the display system, and that can also be configured to operate as circuit elements of the touch sensing circuitry. The OLED display example in FIG. 3 can be implemented to include multi-touch functionality to an OLED display without the need of a separate multi-touch panel or layer overlaying the OLED display. The OLED display, display circuitry, touch sensors, and touch circuitry can be formed on a Silicon substrate. By fabricating the integrated OLED display and touch sensor panel on a Silicon substrate, extremely high pixels per inch (PPI) can be achieved. Other arrangements different from FIG. 3 for the OLED and touch sensing structures are also possible. For example, the touch sensing layers can be an assembly that is located on top of the OLED display assembly.

Referring back to FIGS. 2A and 2B, the illustrated under-screen optical sensor module for on-screen fingerprint sensing may be implemented in various configurations.

In one implementation, a device based on the above design can be structured to include a device screen a that provides touch sensing operations and includes a display panel structure having light emitting display pixels each operable to emit light for forming a display image, a top transparent layer formed over the device screen as an interface for being touched by a user for the touch sensing operations and for transmitting the light from the display structure to display images to a user, and an optical sensor module located below the display panel structure to receive light that is emitted by at least a portion of the light emitting display pixels of the display structure and is returned from the top transparent layer to detect a fingerprint.

This device can be further configured with various features.

For example, a device electronic control module can be included in the device to grant a user's access to the device if a detected fingerprint matches a fingerprint an authorized user. In addition, the optical sensor module is configured to, in addition to detecting fingerprints, also detect a biometric parameter different form a fingerprint by optical sensing to indicate whether a touch at the top transparent layer associated with a detected fingerprint is from a live person, and the device electronic control module is configured to grant a user's access to the device if both (1) a detected fingerprint matches a fingerprint an authorized user and (2) the detected biometric parameter indicates the detected fingerprint is from a live person. The biometric parameter can include, e.g., whether the finger contains a blood flow, or a heartbeat of a person.

For example, the device can include a device electronic control module coupled to the display panel structure to supply power to the light emitting display pixels and to control image display by the display panel structure, and, in a fingerprint sensing operation, the device electronic control module operates to turn off the light emitting display pixels in one frame to and turn on the light emitting display pixels in a next frame to allow the optical sensor array to capture two fingerprint images with and without the illumination by the light emitting display pixels to reduce background light in fingerprint sensing.

For another example, a device electronic control module may be coupled to the display panel structure to supply power to the light emitting display pixels and to turn off power to the light emitting display pixels in a sleep mode, and the device electronic control module may be configured to wake up the display panel structure from the sleep mode when the optical sensor module detects the presence of a person's skin at the designated fingerprint sensing region of the top transparent layer. More specifically, in some implementations, the device electronic control module can be configured to operate one or more selected light emitting display pixels to intermittently emit light, while turning off power to other light emitting display pixels, when the display panel structure is in the sleep mode, to direct the intermittently emitted light to the designated fingerprint sensing region of the top transparent layer for monitoring whether there is a person's skin in contact with the designated fingerprint sensing region for waking up the device from the sleep mode. Also, the display panel structure may be designed to include one or more LED lights in addition to the light emitting display pixels, and the device electronic control module may be configured to operate the one or more LED lights to intermittently emit light, while turning off power to light emitting display pixels when the display panel structure is in the sleep mode, to direct the intermittently emitted light to the designated fingerprint sensing region of the top transparent layer for monitoring whether there is a person's skin in contact with the designated fingerprint sensing region for waking up the device from the sleep mode.

For another example, the device can include a device electronic control module coupled to the optical sensor module to receive information on multiple detected fingerprints obtained from sensing a touch of a finger and the device electronic control module is operated to measure a change in the multiple detected fingerprints and determines a touch force that causes the measured change. For instance, the change may include a change in the fingerprint image due to the touch force, a change in the touch area due to the touch force, or a change in spacing of fingerprint ridges.

For another example, the top transparent layer can include a designated fingerprint sensing region for a user to touch with a finger for fingerprint sensing and the optical sensor module below the display panel structure can include a transparent block in contact with the display panel substrate to receive light that is emitted from the display panel structure and returned from the top transparent layer, an optical sensor array that receives the light and an optical imaging module that images the received light in the transparent block onto the optical sensor array. The optical sensor module can be positioned relative to the designated fingerprint sensing region and structured to selectively receive returned light via total internal reflection at the top surface of the top transparent layer when in contact with a person's skin while not receiving the returned light from the designated fingerprint sensing region in absence of a contact by a person's skin.

For yet another example, the optical sensor module can be structured to include an optical wedge located below the display panel structure to modify a total reflection condition on a bottom surface of the display panel structure that interfaces with the optical wedge to permit extraction of light out of the display panel structure through the bottom surface, an optical sensor array that receives the light from the optical wedge extracted from the display panel structure, and an optical imaging module located between the optical wedge and the optical sensor array to image the light from the optical wedge onto the optical sensor array.

Specific examples of under-screen optical sensor modules for on-screen fingerprint sensing are provided below.

Figure 4A:
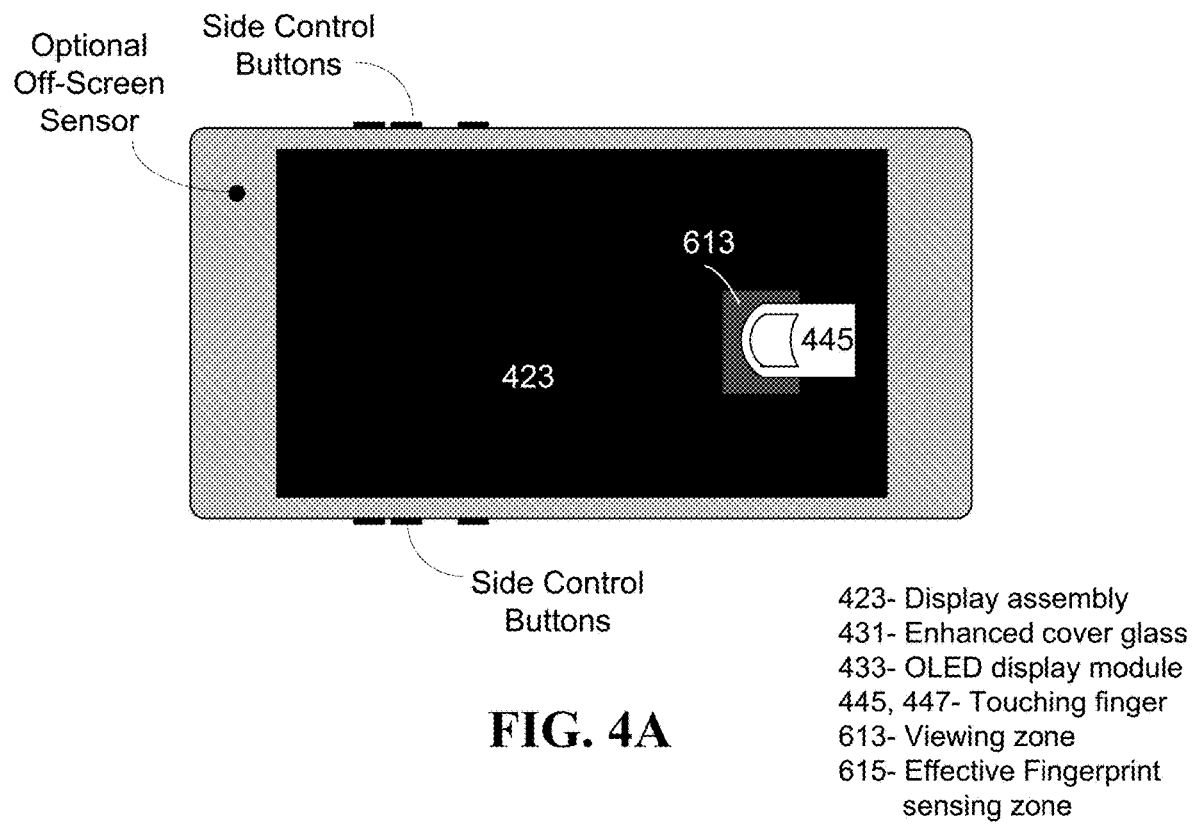
FIGS. 4A and 4B show an example of one implementation of an optical sensor module under the display screen assembly for implementing the design in FIGS. 2A and 2B.
Figure 4B:
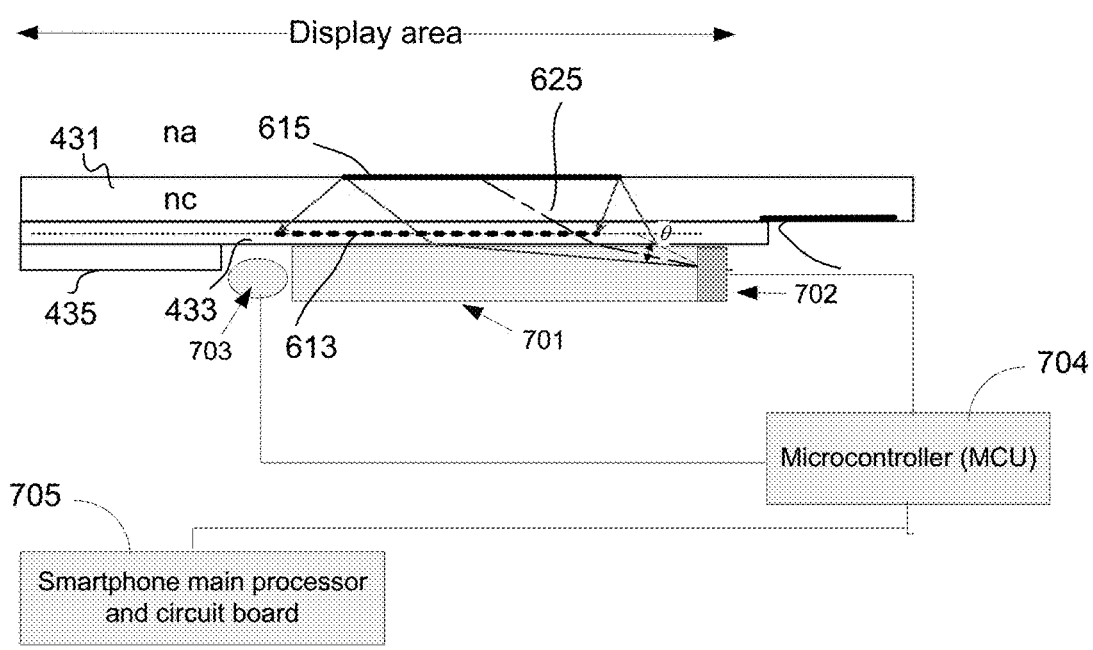

FIG. 4A and FIG. 4B show an example of one implementation of an optical sensor module under the display screen assembly for implementing the design in FIGS. 2A and 2B. The device in FIGS. 4A-4B includes a display assembly 423 with a top transparent layer 431 formed over the device screen assembly 423 as an interface for being touched by a user for the touch sensing operations and for transmitting the light from the display structure to display images to a user. This top transparent layer 431 can be a cover glass or a crystal material in some implementations. The device screen assembly 423 can include an OLED display module 433 under the top transparent layer 431. The OLED display module 433 includes, among others, OLED layers including an array of OLED pixels that emit light for displaying images. The OLED layers have electrodes and wiring structure optically acting as an array of holes and light scattering objects. The array of holes in the OLED layers allows transmission of light from the top transparent layer 431 through the OLED layers to reach the optical sensor module under the OLED layers and the light scattering caused by the OLED layers affects the optical detection by the under-screen optical sensor module for fingerprint sensing. A device circuit module 435 may be provided under the OLED display panel to control operations of the device and perform functions for the user to operate the device.

The optical sensor module in this particular implementation example is placed under OLED display module 433. The OLED pixels in a fingerprint illumination zone 613 can be controlled to emit light to illuminate the fingerprint sensing zone 615 on the top transparent layer 431 within the device screen area for a user to place a finger therein for fingerprint identification. As illustrated, a finger 445 is placed in the illuminated fingerprint sensing zone 615 as the effective sensing zone for fingerprint sensing. A portion of the reflected or scattered light in the zone 615 illuminated by the OLED pixels in the fingerprint illumination zone 613 is directed into the optical sensor module underneath the OLED display module 433 and a photodetector sensing array inside the optical sensor module receives such light and captures the fingerprint pattern information carried by the received light.

In this design of using the OLED pixels in the fingerprint illumination zone 613 within the OLED display panel to provide the illumination light for optical fingerprint sensing, the OLED pixels in the fingerprint illumination zone 613 can be controlled to turn on intermittently with a relatively low cycle to reduce the optical power used for the optical sensing operations. For example, while the rest of the OLED pixels in the OLED panel are turned off (e.g., in a sleep mode), the OLED pixels in the fingerprint illumination zone 613 can be turned on intermittently to emit illumination light for optical sensing operations, including performing optical fingerprint sensing and waking up the OLED panel. The fingerprint sensing operation can be implemented in a 2-step process in some implementations: first, a few of the OLED pixels in the fingerprint illumination zone 613 within the OLED display panel are turned on in a flashing mode without turning on other OLED pixels in the fingerprint illumination zone 613 to use the flashing light to sense whether a finger touches the sensing zone 615 and, once a touch in the zone 615 is detected, the OLED pixels in the fingerprint illumination zone 613 are turned on to activate the optical sensing module to perform the fingerprint sensing. Also, upon activating the optical sensing module to perform the fingerprint sensing, the OLED pixels in the fingerprint illumination zone 613 may be operated at a brightness level to improve the optical detection performance for fingerprint sensing, e.g., at a higher brightness level than their bright level in displaying images.

In the example in FIG. 4B, the under-screen optical sensor module includes a transparent block 701 that is coupled to the display panel to receive the returned light from the top surface of the device assembly that is initially emitted by the OLED pixels in the fingerprint sensing zone 613, and an optical imaging block 702 that performs the optical imaging and imaging capturing. Light from OLED pixels in the fingerprint illumination zone 613, after reaching the cover top surface, e.g., the cover top surface at the sensing area 615 where a user finger touches, is reflected or scattered back from the cover top surface. When fingerprint ridges in close contact of the cover top surface in the sensing area 615, the light reflection under the fingerprint ridges is different, due to the presence of the skin or tissue of the finger in contact at that location, from the light reflection at another location under the fingerprint valley, where the skin or tissue of the finger is absent. This difference in light reflection conditions at the locations of the ridges and valleys in the touched finger area on the cover top surface forms an image representing an image or spatial distribution of the ridges and valleys of the touched section of the finger. The reflection light is directed back towards the OLED pixels, and, after passing through the small holes of the OLED display module 433, reaches the interface with the low index optically transparent block 701 of the optical sensor module. The low index optically transparent block 701 is constructed to have a refractive index less than a refractive index of the OLED display panel so that the returned light can be extracted out of the OLED display panel into the optically transparent block 701. Once the returned light is received inside the optically transparent block 701, such received light enters the optical imaging unit as part of the imaging sensing block 702 and is imaged onto the photodetector sensing array or optical sensing array inside the block 702. The light reflection differences between fingerprint ridges and valleys create the contrast of the fingerprint image. As shown in FIG. 4B is a control circuit 704 (e.g., a microcontroller or MCU) which is coupled to the imaging sensing block 702 and to other circuitry such as the device main processor 705 on a main circuit board.

In this particular example, the optical light path design is such the light ray enters the cover top surface within the total reflect angles on the top surface between the substrate and air interface will get collected most effectively by the imaging optics and imaging sensor array in the block 702. In this design the image of the fingerprint ridge/valley area exhibits a maximum contrast. Such an imaging system may have undesired optical distortions that would adversely affect the fingerprint sensing. Accordingly, the acquired image may be further corrected by a distortion correction during the imaging reconstruction in processing the output signals of the optical sensor array in the block 702 based on the optical distortion profile along the light paths of the returned light at the optical sensor array. The distortion correction coefficients can be generated by images captured at each photodetector pixel by scanning a test image pattern one line pixel at a time, through the whole sensing area in both X direction lines and Y direction lines. This correction process can also use images from tuning each individual pixel on one at a time, and scanning through the whole image area of the photodetector array. This correction coefficients only need to be generated one time after assembly of the sensor.

The background light from environment (e.g., sun light or room light) may enter the image sensor through OLED panel top surface, through TFT substrate holes in the OLED display assembly 433. Such background light can create a background baseline in the interested images from fingers and is undesirable. Different methods can be used to reduce this baseline intensity. One example is to tune on and off the OLED pixels in the fingerprint illumination zone 613 at a certain frequency F and the image sensor accordingly acquires the received images at the same frequency by phase synchronizing the pixel driving pulse and image sensor frame. Under this operation, only one of the image phases has the lights emitted from pixels. By subtracting even and odd frames, it is possible to obtain an image which most consists of light emitted from the modulated OLED pixels in the fingerprint illumination zone 613. Based on this design, each display scan frame generates a frame of fingerprint signals. If two sequential frames of signals by turning on the OLED pixels in the fingerprint illumination zone 613 in one frame and off in the other frame are subtracted, the ambient background light influence can be minimized or substantially eliminated. In implementations, the fingerprint sensing frame rate can be one half of the display frame rate.

A portion of the light from the OLED pixels in the fingerprint illumination zone 613 may also go through the cover top surface, and enter the finger tissues. This part of light power is scattered around and a part of this scattered light may go through the small holes on the OLED panel substrate, and is eventually collected by the imaging sensor array in the optical sensor module. The light intensity of this scattered light depends on the finger's skin color, the blood concentration in the finger tissue and this information carried by this scattered light on the finger is useful for fingerprint sensing and can be detected as part of the fingerprint sensing operation. For example, by integrating the intensity of a region of user's finger image, it is possible to observe the blood concentration increase/decrease depends on the phase of the user's heart-beat. This signature can be used to determine the user's heart beat rate, to determine if the user's finger is a live finger, or to provide a spoof device with a fabricated fingerprint pattern.

Referring to the OLED display example in FIG. 3, an OLED display usually has different color pixels, e.g., adjacent red, green and blue pixels form one color OLED pixels. By controlling which color of pixels within each color pixel to turn on and recording corresponding measured intensity, the user's skin color may be determined. As an example, when a user registers a finger for fingerprint authentication operation, the optical fingerprint sensor also measures intensity of the scatter light from finger at color A, and B, as intensity Ia, Ib. The ratio of Ia/Ib could be recorded to compare with later measurement when user's finger is placed on the sensing area to measure fingerprint. This method can help reject the spoof device which may not match user's skin color.

In some implementations, to provide a fingerprint sensing operation using the above described optical sensor module when the OLED display panel is not turn on, one or more extra LED light sources 703 designated for providing fingerprint sensing illumination can be placed on the side of the transparent block 701 as shown in FIG. 4B. This designated LED light 703 can be controlled by the same electronics 704 (e.g., MCU) for controlling the image sensor array in the block 702. The designated LED light 703 can be pulsed for a short time, at a low duty cycle, to emit light intermittently and to provide pulse light for image sensing. The image sensor array can be operated to monitor the light pattern reflected off the OLED panel cover substrate at the same pulse duty cycle. If there is a human finger touching the sensing area 615 on the screen, the image that is captured at the imaging sensing array in the block 702 can be used to detect the touching event. The control electronics or MCU 704 connected to the image sensor array in the block 702 can be operated to determine if the touch is by a human finger touch. If it is confirmed that it is a human finger touch event, the MCU 704 can be operated to wake up the smartphone system, turn on the OLED display panel (or at least the off the OLED pixels in the fingerprint illumination zone 613 for performing the optical fingerprint sensing), and use the normal mode to acquire a full fingerprint image. The image sensor array in the block 702 will send the acquired fingerprint image to the smartphone main processor 705 which can be operated to match the captured fingerprint image to the registered fingerprint database. If there is a match, the smartphone will unlock the phone, and start the normal operation. If the captured image is not matched, the smartphone will feedback to user that the authentication is failed. User may try again, or input passcode.

In the example in FIG. 4 (specifically, FIG. 4B), the under-screen optical sensor module uses the optically transparent block 701 and the imaging sensing block 702 with the photodetector sensing array to optically image the fingerprint pattern of a touching finger in contact with the top surface of the display screen onto the photodetector sensing array. The optical imaging axis or detection axis 625 from the sensing zone 615 to the photodetector array in the block 702 is illustrated in FIG. 4B. The optically transparent block 701 and the front end of the imaging sensing block 702 before the photodetector sensing array forma a bulk imaging module to achieve proper imaging for the optical fingerprint sensing. Due to the optical distortions in this imaging process, a distortion correction can be used, as explained above, to achieve the desired imaging operation.

2-Dimensional Optical Reflective Pattern from a Finger

When probe light is directed to a finger, a portion of the probe light can be reflected, diffracted or scattered at the finger skin surface to produce reflected, diffracted or scattered probe light without entering the internal side of the finger. This portion of the probe light without entering the finger can carry a 2-dimensional optical reflective pattern across the reflected probe light beam caused by the external ridges and valleys of the finger and can be detected to obtain the fingerprint pattern of the external ridges and valleys. This is explained with reference to the examples in FIGS. 5A and 5B in this subsection.

In addition, a portion of the probe light may enter the finger and is scattered by the internal tissues in the finger. Depending on the optical wavelength of the probe light inside the finger, the internal tissues in the finger be optically absorptive and thus can be severally attenuated except for probe light in an optical transmission spectral range roughly from 590 nm and 950 nm. The probe light that can transmit through the finger tissues carries an optical transmissive pattern across the beam and this transmitted probe light beam can carry both a 2-dimensional pattern of the ridges and valleys and an additional topographical information of the internal issues associated with the ridges and valleys due to the internal path through such internal tissues before exiting the finger skin. This optical transmissive pattern is explained with reference to examples in FIGS. 5C and 5D in the next subsection.

In the optical sensing by the under-screen optical sensor module in FIGS. 4A-4B and other designs disclosed herein, the optical signal from the sensing zone 615 on the top transparent layer 431 to the under-screen optical sensor module include different light components.

FIGS. 5A and 5B illustrate signal generation for the returned light from the sensing zone 615 for OLED-emitted light or other illumination light at different incident angle ranges under two different optical conditions to facilitate the understanding of the operation of the under-screen optical sensor module.

FIG. 5A shows optical paths of selected OLED-emitted light rays from OLED pixels in the OLED display module 433 that are incident to and transmit through the top transparent layer 431 at small incident angles at the top surface of the transparent layer 431 without the total internal reflection. Such OLED-emitted light rays at small incident angles generates different returned light signals including light signals that carry fingerprint pattern information to the under-screen optical sensor module. Specifically, two OLED pixels 71 and 73 at two different locations are shown to emit OLED output light beams 80 and 82 that are directed to the top transparent layer 431 in a direction that is either perpendicular to the top transparent layer 431 or at relatively small incident angles without experiencing the total reflection at the interfaces of the top transparent layer 431. In the particular example illustrated in FIG. 5A, a finger 60 is in contact with the sensing zone 615 on the e top transparent layer 431 and a finger ridge 61 is located above the OLED pixel 71 and a finger valley 63 is located above the OLED pixel 73. As illustrated, the OLED light beam 80 from the OLED pixel 71 toward the finger ridge 61 reaches the finger ridge 61 in contact with the top transparent layer 431 after transmitting through the top transparent layer 431 to generate a transmitted light beam 183 in the finger tissue and another scattered light beam 181 back towards the OLED display module 433. The OLED light beam 82 from the OLED pixel 73 reaches the finger valley 63 located above the top transparent layer 431 after transmitting through the top transparent layer 431 to generate the reflected light beam 185 from the interface with the top transparent layer 431 back towards the OLED display module 433, a second light beam 189 that enters the finger tissue and a third light beam 187 reflected by the finger valley surface.

In the example in FIG. 5A, it is assumed that the finger skin's equivalent index of refraction is about 1.44 at the optical wavelength of 550 nm and the cover glass index of refraction is about 1.51 for the top transparent layer 431. It is also assumed that the finger is clean and dry so that the void between adjacent finger valley and ridge is air. Under those assumptions, the display OLED pixel 71 is turned on at the finger skin ridge location 61 to produce the beam 80. The finger ridge-cover glass interface reflects part of the beam 80 as reflected light 181 to bottom layers 524 below the OLED display module 433. The reflectance is low and is about 0.1%. The majority of the light beam 80 (around 99%) becomes the transmitted beam 183 that transmits into the finger tissue 60 which causes scattering of the light 183 to contribute to the returned scattered light 191 towards the OLED display module 433 and the bottom layers 524.

The OLED-emitted beam 82 from the OLED pixel 73 towards the external valley 63 first passes the interface of the top transparent layer 431 and the air gap due to the presence of the external valley 63 to produce the reflected beam 185 and the remaining portion of the light beam 82 is incident onto the valley 62 to produce the transmitted light beam 189 inside the finger and a reflected beam 187. Similar to the transmitted beam 183 at the finger ridge 61, the transmitted light beam 189 from the OLED pixel 73 in the finger tissue is scattered by the finger tissues and a portion of this scattered light also contributes to the returned scattered light 191 that is directed to towards the OLED display module 433 and the under layers 524. Under the assumptions stated above, about 3.5% of the beam 82 from the display OLED group 73 at the finger skin valley location 63 is reflected by the cover glass surface as the reflected light 185 to the bottom layers 524, and the finger valley surface reflects about 3.3% of the incident light power of the remainder of the beam 82 as the reflected light 187 to bottom layers 524. The total reflection represented by the two reflected beams 185 and 187 is about 6.8% and is much stronger than the reflection 181 at about 0.1% at a finger ridge 61. Therefore, the light reflections 181 and 185/187 from various interface or surfaces at finger valleys 63 and finger ridges 61 of a touching finger are different and form an optical reflective pattern in which the reflection ratio difference carries the fingerprint map information and can be measured to extract the fingerprint pattern of the portion that is in contact with the top transparent layer 431 and is illuminated the OLED light or other illumination light such as extra illumination light sources.

At each finger valley 63, the majority of the beam 82 towards the finger valley 63 (more than 90%) is transmitted into the finger tissues 60 as the transmitted light 189. Part of the light power in the transmitted light 189 is scattered by internal tissues of the finger to contribute to the scattered light 191 towards and into the bottom layers 524. Therefore, the scattered light 191 towards and into the bottom layers 524 includes contributions from both the transmitted light 189 at finger valleys 63 and transmitted light 183 at finger ridges 61.

The example in FIG. 5A shows incident OLED-emitted light to the top transparent layer 431 at small incident angles without the total internal reflection in the top transparent layer 431. For OLED-emitted light incident to the top transparent layer 431 at relatively large incident angles at or greater than the critical angle for the total internal reflection, another higher-contrast optical reflective pattern can be generated to capture the 2-dimensional fingerprint pattern of the external ridges and valleys of a finger. FIG. 5B shows examples of selected OLED-emitted light rays from an OLED pixel 73 in the OLED display module 433 located under a finger valley 63 where some of the illustrated light rays are under a total reflection condition at the interface with the top transparent layer 431 at locations adjacent to the particular finger valley 73. Those illustrated examples of incident light rays generate different returned light signals including light signals that carry fingerprint pattern information to the under-screen optical sensor module. It is assumed that the cover glass 431 and the OLED display module 433 are glued together without any air gap in between so that an OLED light beam emitted by an OLED pixel 73 with a large incident angle to the cover glass 431 at or greater than the critical angle will be totally reflected at the cover glass-air interface. When the display OLED pixel 73 is turned on, the divergent light beams emitted by the OLED pixel 73 can be divided into three groups: (1) central beams 82 with small incident angles to the cover glass 431 without the total reflection, (2) high contrast beams 201, 202, 211, 212 that are totally reflected at the cover glass 431 when nothing touches the cover glass surface and can be coupled into finger tissues when a finger touches the cover glass 431, and (3) escaping beams having very large incident angles that are totally reflected at the cover glass 431 even at a location where the finger is in contact.

For the central light beams 82, as explained in FIG. 5A, the cover glass surface reflects about 0.1%~3.5% to produce the reflected light beam 185 that is transmitted into bottom layers 524, the finger skin reflects about 0.1%~3.3% at the air-finger valley interface to produce a second reflected light beam 187 that is also transmitted into bottom layers 524. As explained above with reference to FIG. 5A, the reflection difference in the reflected rays at small incident angles varies spatially and is dependent on whether the light beams 82 or light beams 80 meet with finger skin valley 63 or ridge 61. The rest of the such incident light rays with small incident angles becomes the transmitted light beams 189 and 183 that are coupled into the finger tissues 60.

FIG. 5B shows high contrast light beams 201 and 202 as examples. The cover glass surface reflects nearly 100% as reflected light beams 205 and 206 respectively if nothing touches the cover glass surface at their respective incident positions. When the finger skin ridges touch the cover glass surface and at the incident positions of the illustrated OLED-emitted light beams 201 and 202, there is no longer the condition for the total internal reflection and thus most of the light power is coupled into the finger tissues 60 as transmitted light beams 203 and 204. For such beams with large incident angles, this change between being under the total internal reflection condition in absence of a finger skin and being out of the total internal reflection condition with a significantly reduced reflection when a finger skin touches is used to produce a contrast pattern in the reflection.

FIG. 5B further shows additional high contrast light beams 211 and 212 as examples for which the cover glass surface reflects nearly 100% to produce corresponding reflected light beams 213 and 214 respectively under the total internal reflection condition if nothing touches the cover glass surface. For example, when the finger touches the cover glass surface and the finger skin valleys happen to be at the incident positions of the light beams 211 and 212, no light power is coupled into finger tissues 60 due to the total internal reflection. If, by contrast, finger ridges happen to be at the incident positions of the light beams 211 and 212, the light power that is coupled into finger tissues 60 increases due to the lack of the total internal reflection caused by the contact of the finger skin.

Similar to the situation in FIG. 5A, light beams (e.g., transmitted beams 203 and 204) that are coupled into finger tissues 60 will experience random scattering by the figure tissues to form the scattered light 191 that propagates towards the bottom layers 524.

The illumination for the examples shown in FIG. 5B can be caused by illumination by the OLED-emitted light or illumination light from extra illumination light sources. In high contrast light beams illuminated area, finger skin ridges and valleys cause different optical reflections and the reflection difference pattern carries the fingerprint pattern information. The high contrast fingerprint signals can be achieved by comparing the difference.

Therefore, as shown in FIGS. 5A and 5B, incident illumination light rays from either OLED-emitted light or extra illumination light sources can produce two types of optical reflection patterns representing the same 2-dimensional fingerprint pattern of a finger: a low contrast optical reflective pattern formed by incident illumination light rays at small incident angles without the total internal reflection and a high contrast optical reflective pattern formed by incident illumination light rays at large incident angles based on a total internal reflection.

2-Dimensional and 3-Dimensional Optical Transmissive Pattern from a Finger

In both FIGS. 5A and 5B, a portion of the incident illumination light rays from either OLED-emitted light or extra illumination light passes through the top transparent layer 431 and enters the finger to cause the scattered light 191 that propagates through the internal tissues of the finger and to penetrate through the finger skin to enter the top transparent layer 431 towards the bottom layers 524. As explained below, such scattered light 191, once transmitting through the internal tissues and the finger skin, carries an optical transmissive pattern of the finger that contains both (1) a 2-dimensional spatial pattern of external ridges and valleys of a fingerprint (2) an internal fingerprint pattern associated with internal finger tissue structures that give rise to the external ridges and valleys of a finger due to the propagation of the scattered light from the internal side of the finger towards the finger skin and transmits the finger skin. Accordingly, the scattered light 191 from the finger can be measured by the optical sensor array and the measurements can be processed for fingerprint sensing. Notably, the internal fingerprint pattern associated with internal finger tissue structures that give rise to the external ridges and valleys of a finger is not substantially affected by the sensing surface condition of the top surface of the top transparent layer 431 or the skin conditions of the finger (e.g., dirty, wet/dry or aged finger patterns) and may still provide sufficient information for fingerprint sensing when the external fingerprint pattern on the external finger skin has a reduced ridge-valley contrast, is somewhat damaged or otherwise is not suitable for providing sufficient fingerprint information in the optical reflective pattern. While the external fingerprint pattern may be duplicated by using artificial materials for invading the fingerprint sensing, the internal fingerprint pattern of a user's finger imprinted in the optical transmissive pattern is extremely difficult to replicate and thus can be used as an anti-spoofing mechanism in the fingerprint sensing.

FIG. 5C shows an example of an external fingerprint pattern formed by external ridges and valleys of a person's finger and the internal finger issues that are under the skin and are uniquely associated with the external ridges and valleys. See, e.g., Chapter 2 of "*The Fingerprint Sourcebook*" by Holder et al. (U.S. Department of Justice, Office of Justice Programs, National Institute of Justice, Washington, D.C., 2011). As illustrated in FIG. 5C, the internal tissues include the papillary layer under the finger skin that has topographical features from which external ridges and valleys are formed as an expression of the underlying topographical features. In addition, the internal tissues also contain additional structures that are not identically replicated on the external ridges and valleys such as the internal primary and secondary ridges, the sweat glands connected to the primary ridges and other internal structures. As illustrated in FIG. 5C, when probe light propagates from the internal side of the finger outward to the finger skin, the probe light interacts with the internal tissues under the finger skin to carry not only the 2-dimensional fingerprint pattern of the papillary layer that is identical to the external fingerprint pattern formed by the external ridges and valleys but also additional topographical information from the internal tissue structures that is not carried by the external ridges and valleys. Such additional topographical information from the internal tissue structures cannot be obtained from the optical reflective pattern obtained from the optical reflection off the external finger skin. The additional topographical information from the internal tissue structures below the finger skin is valuable information for fingerprint sensing and is 3-dimensional since the internal tissue structures vary with both the lateral position under the skin and the depth from the skin surface (topographical information). Such additional topographical information from the internal tissue structures of a finger can be used, for example, to distinguish a natural finger from an artificial object manufactured with similar or identical external fingerprint pattern as the natural finger.

Referring to FIG. 5C, different illumination probe light beams go through different parts of the under-skin internal tissue structures and thus are imprinted with different 3-D topographical information associated with the different optical paths in different directions of such illumination probe light beams. Imaging processing techniques can be used to process the optical transmissive patterns carried by such different illumination probe light beams to extract the topographical features associated with the under-skin internal tissue structures. The extracted topographical features can be synthesized to construct a 3-D representation or rendition of the under-skin internal tissue structures associated with the fingerprint pattern and this constructed 3-D representation of the under-skin internal tissue structures associated with the fingerprint pattern can be used as a unique and additional identification for the fingerprint pattern and can be used to distinguish a true fingerprint pattern from a real finger of a user from a fabricated fingerprint pattern that would invariably lack of the underlying internal tissue structures of the real finger. In particular, as the number of the different illumination probe light beams in the different directions increases, the more detailed topographical information on the under-skin internal tissue structures can be captured by the optical sensor module. In using the fingerprint for a secured access to the device, the fingerprint identification process can be designed to combine the identification of the 2-D fingerprint pattern and the additional examination of the extracted 3-D representation or rendition of the under-skin internal tissue structures associated with the fingerprint pattern to determine whether or not to grant the access. The extracted topographical features and the constructed 3-D representation or rendition of the under-skin internal tissue structures associated with the fingerprint pattern can be an anti-spoofing mechanism and can used alone or in combination with other anti-spoofing techniques to enhance the security and accuracy of the fingerprint sensing.

One way for the disclosed optical fingerprint sensing technology to capture additional topographical information from the internal tissue structures of a finger is by directing different illumination probe light beams at different directions to detect the different optical shadowing patterns produced by the internal tissue structures under the finger skin that are superimposed over the 2-dimensional fingerprint pattern that is common to all images obtained from the illumination by the different illumination probe light beams at different directions.

FIG. 5D shows that two extra illumination light sources X1 and X2 are placed on two opposite sides of the fingerprint sensing area on the top transparent layer 431 along the X direction so that they can direct two different illumination probe beams to the finger in opposite directions. The images from both illumination probe beams carry the same 2-D fingerprint pattern but different image shadowing patterns due to their different illumination directions with respect to the internal tissue structures under the finger skin. Specifically, the first extra illumination light source X1 is placed on the left side of the fingerprint sensing area along the X direction so that the first illumination probe beam from the first extra illumination light source X1 is from the left to the right in FIG. 5D. This illumination by the first extra illumination light source X1 causes a shadowing pattern in the first fingerprint image at the under-OLED optical sensor array due to the interaction with the internal tissue structures under the finger skin and this shadowing pattern is shifted spatially towards the right in the X direction. The illumination by the second extra illumination light source X2 on the right side causes a shadowing pattern in the second fingerprint image at the under-OLED optical sensor array due to the interaction with the internal tissue structures under the finger skin and this shadowing pattern is shifted spatially towards the left in the X direction. In implementation of this technique, additional extra illumination light sources may be added, e.g., in the Y direction or in other directions.

In this example, the first illumination probe beam in the first illumination direction from the first extra illumination light source X1 leads to generation of the first scattered probe light by scattering of tissues inside the finger that propagates the internal tissues associated with ridges and valleys of the finger to carry both (1) a first 2-dimensional transmissive pattern representing a fingerprint pattern formed by bridges and valleys of the finger, and (2) a first fingerprint topographical pattern that is associated with the illumination of internal tissues of ridges and valleys of the finger in the first illumination direction and is embedded within the first 2-dimensional transmissive pattern. Similarly, the second illumination probe beam in the second illumination direction from the second extra illumination light source X2 leads to generation of the first scattered probe light by scattering of tissues inside the finger that propagates the internal tissues associated with ridges and valleys of the finger to carry both (1) a second 2-dimensional transmissive pattern representing the fingerprint pattern formed by bridges and valleys of the finger, and (2) a second fingerprint topographical pattern that is associated with the illumination of internal tissues of ridges and valleys of the finger in the second illumination direction and is embedded within the second 2-dimensional transmissive pattern. The two extra illumination light sources X1 and X2 are turned on sequentially at different times so that the optical sensor array can be operated to detect transmitted part of the first scattered probe light that passes through the top transparent layer and the display panel to reach the optical sensor array so as to capture both the first 2-dimensional transmissive pattern, and the first fingerprint topographical pattern and then the second 2-dimensional transmissive pattern and the second fingerprint topographical pattern. The shadowing patterns shown in FIG. 5D are embedded in the captured 2-D fingerprint patterns and are one form of the fingerprint topographical pattern that is associated with the illumination of internal tissues of ridges and valleys of the finger at a particular direction.

In various implementations, two or more extra illumination light sources can be located outside the optical sensor module at different locations to produce different illumination probe beams to illuminate the designated fingerprint sensing area on the top transparent layer in different illumination directions. Since this technique is based on the ability for the probe light to transmit through the finger tissues, each extra illumination light source should be structured to produce probe light in an optical spectral range with respect to which tissues of a human finger exhibit optical transmission to allow probe light to enter a user finger to produce scattered probe light by scattering of tissues inside the finger that propagates towards and passes the top transparent layer to carry both (1) fingerprint pattern information and (2) different fingerprint topographical information associated with the different illumination directions, respectively, caused by transmission through internal tissues of ridges and valleys of the finger. A probe illumination control circuit can be coupled to control the extra illumination light sources to sequentially turn on and off in generating the different illumination probe beams at different times, one beam at a time, so that the optical sensor module located below the display panel is operable to sequentially detect the scattered probe light from the different illumination probe beams to capture both (1) the fingerprint pattern information and (2) the different fingerprint topographical information associated with the different illumination directions, respectively.

In addition to using light sources that are independent of the OLED pixels as the extra illumination light sources located outside the optical sensor module at different locations to produce the different illumination probe beams in different illumination directions, such two or more extra illumination light sources use two or more different OLED pixels at selected different locations with respect to the optical sensor module and outside OLED display area on top of the optical sensor module to produce the different illumination probe beams to illuminate the designated fingerprint sensing area on the top transparent layer in different illumination directions. This can be done by turning on such OLED pixels at different times while turning off all other OLED pixels to obtain the directional illumination at two or more different directions to measure the spatially shifted shadowing patterns caused by the internal tissue structures of the finger.

One notable feature of the disclosed technique in FIG. 5D is the simplicity of the illumination arrangement, the optical detection and the signal processing which can lead to compact optical sensor packaging for mobile and other applications that desire compact sensing device packaging, and real-time processing since the detection and the subsequent processing are simple operations that can be achieved at high speed without complex signal processing. Various optical imaging techniques for capturing 3-D images require complex optical imaging systems and complex and time-consuming signal processing, such as optical coherence tomography (OCT) imaging based on complex OCT data processing such as fast Fourier transform (FFT) and others that are not suitable for 3-D optical fingerprint sensing in smartphones and other mobile devices.

In the examples above, the illumination light for obtaining an optical transmissive pattern of a finger can be from the OLED pixels of the OLED display or extra illumination light sources that are separate from the OLED display. In addition, a portion of the environmental or background light that is within the optical transmission spectral band of a finger (e.g., optical wavelengths between 650 nm and 950 nm) and penetrates through a finger may also be directed into the under-OLED optical sensor array to measure an optical transmissive pattern associated with a fingerprint pattern of the finger. Depending on the intensity of the environmental or background light (e.g., the natural daylight or sunlight), optical attenuation may be provided in the optical path to the optical sensor module to avoid detection saturation at the optical sensor array. In using a portion of the environmental or background light for obtaining the optical transmissive pattern of a finger in optical sensing, proper spatial filtering can be implemented to block the environmental light that does transmits through the finger from entering the optical sensor module since such environmental light does not carry internal fingerprint pattern and can adversely flood the optical detectors in the optical sensor module.

Therefore, the disclosed optical fingerprint sensing can use transmitted light through a finger to capture an optical transmissive pattern of the finger with information on the internal fingerprint pattern associated with the external ridges and valleys of a finger under the finger skin. The transmission of the light is through the finger tissues and the stratum corneum of the finger skin and thus is imprinted with the fingerprint information by the internal structural variations inside the finger skin caused by the fingerprint ridge area and valley area and such internal structural variations manifest light signals with different brightness patterns in different illumination directions caused by the finger tissue absorption, refraction, and reflection, by finger skin structure shading, and/or by optical reflectance difference at the finger skin. This optical transmissive pattern is substantially immune from the contact conditions between the finger and the top touch surface of the device (e.g., dirty contact surface) and the conditions of the external finger skin condition (e.g., dirty, dry or wet fingers, or reduced external variations between ridges and valleys in fingers of certain users such as aged users), Examples of Under-Screen Optical Sensor Module Designs for Capturing Optical Reflective and Transmissive Patterns The disclosed under-screen optical sensing technology can be in various configurations to optically capture fingerprints based on the design in FIGS. 2A and 2B.

For example, the specific implementation in FIG. 4B based on optical imaging by using a bulk imaging module in the optical sensing module can be implemented in various configurations. FIGS. 6A-6C, 7, 8A-8B, 9, 10A-10B, 11 and 12 illustrate examples of various implementations and additional features and operations of the under-screen optical sensor module designs for optical fingerprint sensing.

Figure 6A:
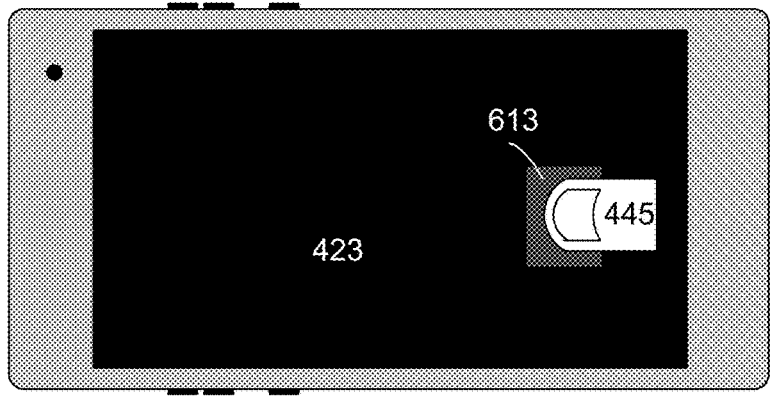
FIGS. 6A-6C show examples of an under-screen optical sensor module based on optical imaging via a lens for capturing a fingerprint from a finger pressing on the display cover glass.
Figure 6B:
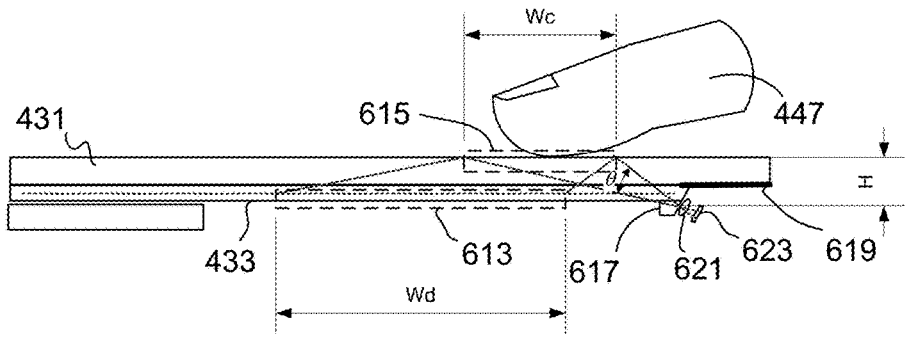
Figure 6C:
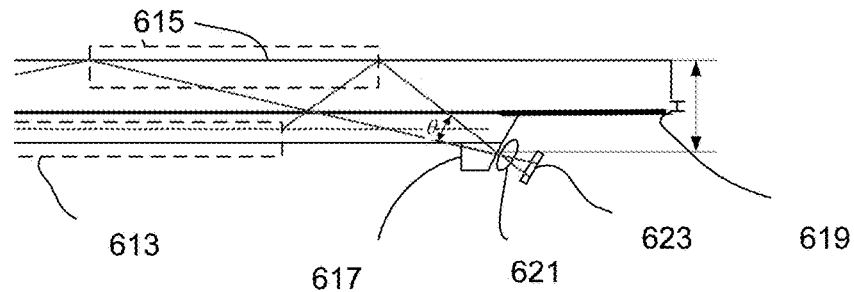

FIG. 6A, FIG. 6B and FIG. 6C show an example of a under-screen optical sensor module based on optical imaging via a lens for capturing a fingerprint from a finger 445 pressing on the display cover glass 423. FIG. 6C is an enlarged view of the optical sensor module part shown in FIG. 6B. The under-screen optical sensor module as shown in FIG. 6B is placed under the OLED display module 433 includes an optically transparent spacer 617 that is engaged to the bottom surface of the OLED display module 433 to receive the returned light from the sensing zone 615 on the top surface of the top transparent layer 431, an imaging lens 621 that is located between and spacer 617 and the photodetector array 623 to image the received returned light from the sensing zone 615 onto the photodetector array 623. Like the imaging system in the example in FIG. 4B, this imaging system in FIG. 6B for the optical sensor module can experience image distortions and a suitable optical correction calibration can be used to reduce such distortions, e.g., the distortion correction methods described for the system in FIG. 4B.

Similar to the assumptions in FIGS. 5A and 5B, it is assumed that the finger skin's equivalent index of refraction to be about 1.44 at 550 nm and a bare cover glass index of refraction to be about 1.51 for the cover glass 423. When the OLED display module 433 is glued onto the cover glass 431 without any air gap, the total inner reflection happens in large angles at or larger than the critical incident angle for the interface. The total reflection incident angle is about 41.8° if nothing is in contact with the cover glass top surface, and the total reflection angle is about 73.7° if the finger skin touches the cover glass top surface. The corresponding total reflection angle difference is about 31.9°.

In this design, the micro lens 621 and the photodiode array 623 define a viewing angle θ for capturing the image of a contact finger in the sensing zone 615. This viewing angle can be aligned properly by controlling the physical parameters or configurations in order to detect a desired part of the cover glass surface in the sensing zone 615. For example, the viewing angle may be aligned to detect the total inner reflection of the OLED display assembly. Specifically, the viewing angle θ is aligned to sense the effective sensing zone 615 on the cover glass surface. The effective sensing cover glass surface 615 may be viewed as a mirror so that the photodetector array effectively detects an image of a viewing zone or the fingerprint illumination zone 613 in the OLED display that is projected by the sensing cover glass surface 615 onto the photodetector array. If the OLED pixels in the viewing zone/fingerprint illumination zone 613 are turned on to emit light, the photodiode/photodetector array 623 can receives the image of the zone 613 that is reflected by the sensing cover glass surface 615. When a finger touches the sensing zone 615, some of the light can be coupled into the fingerprint's ridges and this will cause the photodetector array to receive light from the location of the ridges to appear as a darker image of the fingerprint. Because the geometrics of the optical detection path are known, the fingerprint image distortion caused in the optical path in the optical sensor module can be corrected.

Consider, as a specific example, that the distance H in FIG. 6B from the detection module central axis to the cover glass top surface is 2 mm. This design can directly cover 5 mm of an effective sensing zone 615 with a width Wc on the cover glass. Adjusting the spacer 617 thickness can adjust the detector position parameter H, and the effective sensing zone width Wc can be optimized. Because H includes the thickness of the cover glass 431 and the display module 433, the application design should take these layers into account. The spacer 617, the micro lens 621, and the photodiode array 623 can be integrated under the color coating 619 on the bottom surface of the top transparent layer 431.

Figure 7:
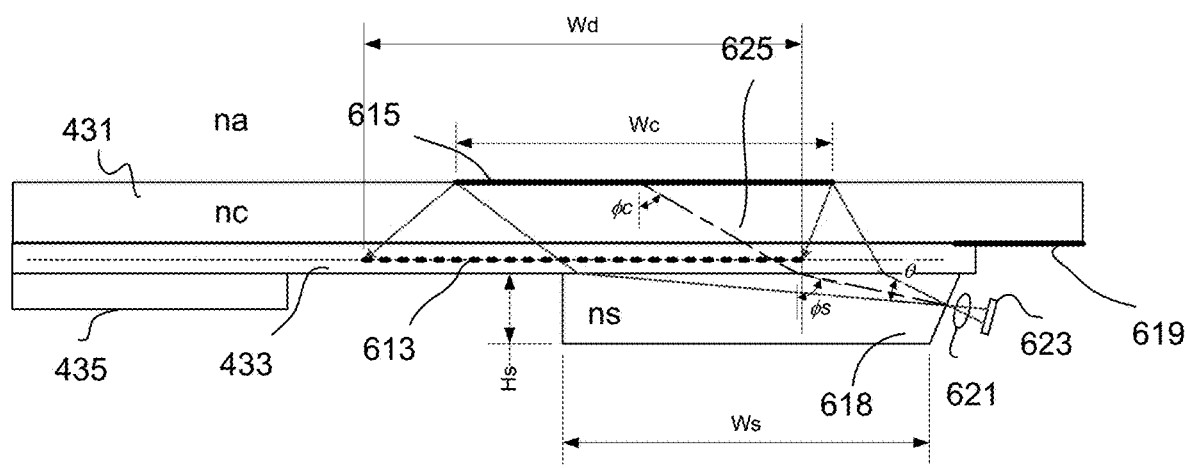
FIG. 7 shows an example of further design considerations of the optical imaging design for the optical sensor module shown in FIGS. 6A-6C.

FIG. 7 shows an example of further design considerations of the optical imaging design for the optical sensor module shown in FIGS. 6A-6C by using a special spacer 618 to replace the spacer 617 in FIGS. 6B-6C to increase the size of the sensing area 615. The spacer 618 is designed with a width Ws and thickness is Hs to have a low refraction index (RI) ns, and is placed under the OLED display module 433, e.g., being attached (e.g., glued) to the bottom surface the OLED display module 433. The end facet of the spacer 618 is an angled or slanted facet that interfaces with the micro lens 621. This relative position of the spacer and the lens is different from FIGS. 6B-6C where the lens is placed underneath the spacer 617. The micro lens 621 and a photodiode array 623 are assembled into the optical detection module with a detection angle width θ. The detection axis 625 is bent due to optical refraction at the interface between the spacer 618 and display module 433 and at the interface between the cover glass 431 and the air. The local incident angle φ1 and φ2 are decided by the refractive indices RIs, ns, nc, and na of the materials for the components.

If nc is greater than ns, φ1 is greater than φ2. Thus, the refraction enlarges the sensing width Wc. For example, assuming the finger skin's equivalent RI is about 1.44 at 550 nm and the cover glass index RI is about 1.51, the total reflection incident angle is estimated to be about 41.8° if nothing touches the cover glass top surface, and the total reflection angle is about 73.7° if the finger skin touches the cover glass top surface. The corresponding total reflection angle difference is about 31.9°. If the spacer 618 is made of same material of the cover glass, and the distance from the detection module center to the cover glass top surface is 2 mm, if detection angle width is θ=31.9°, the effective sensing area width Wc is about 5 mm. The corresponding central axis's local incident angle is $\phi1=\phi2=57.75°$. If the material for the special spacer 618 has a refractive index ns about 1.4, and Hs is 1.2 mm and the detection module is tilted at $\phi1=70°$. The effective sensing area width is increased to be greater than 6.5 mm. Under those parameters, the detection angle width in the cover glass is reduced to 19°. Therefore, the imaging system for the optical sensor module can be designed to desirably enlarge the size of the sensing area 615 on the top transparent layer 431.

When the RI of the special spacer 618 is designed to be sufficiently low (e.g., to use MgF2, CaF2, or even air to form the spacer), the width Wc of the effective sensing area 615 is no longer limited by the thickness of the cover glass 431 and the display module 433. This property leaves designer desired flexibility. In principle, if the detection module has enough resolution, the effective sensing area can even be increased to cover all the display screen.

Since the disclosed optical sensor technology can be used to provide a large sensing area for capturing a pattern, the disclosed under-screen optical sensor modules may be used to capture and detect not only a pattern of a finger but a larger size patter such a person's palm that is associated with a person for user authentication.

Figure 8A:
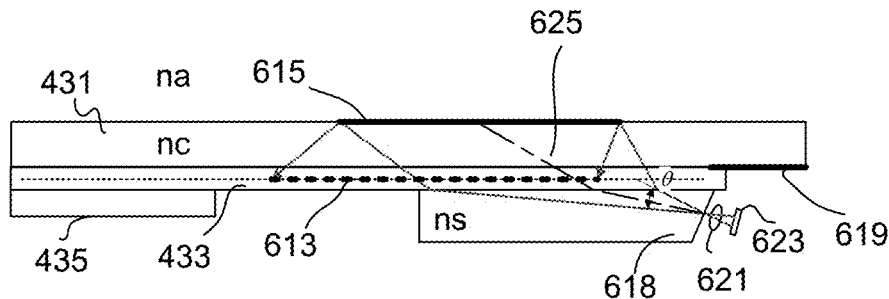
FIGS. 8A-8B show examples of further design considerations of the optical imaging design for the optical sensor module shown in FIG. 7.
Figure 8B:
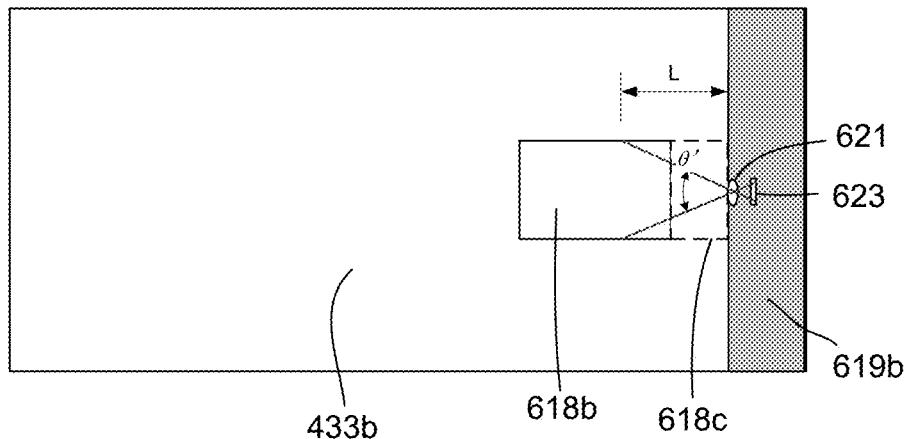

FIGS. 8A-8B show an example of further design considerations of the optical imaging design for the optical sensor module shown in FIG. 7 by setting the detection angle θ' of the photodetector array relative in the display screen surface and the distance L between the lens 621 and the spacer 618. FIG. 8A shows a cross-sectional view along the direction perpendicular to the display screen surface and FIG. 8B shows a view of the device from either the bottom or top of the displace screen. A filling material 618c can be used to fill the space between the lens 621 and the photodetector array 623. For example, the filling material 618c can be same material of the special spacer 618 or another different material. In some designs, the filling material 618c may the air space.

Figure 9:
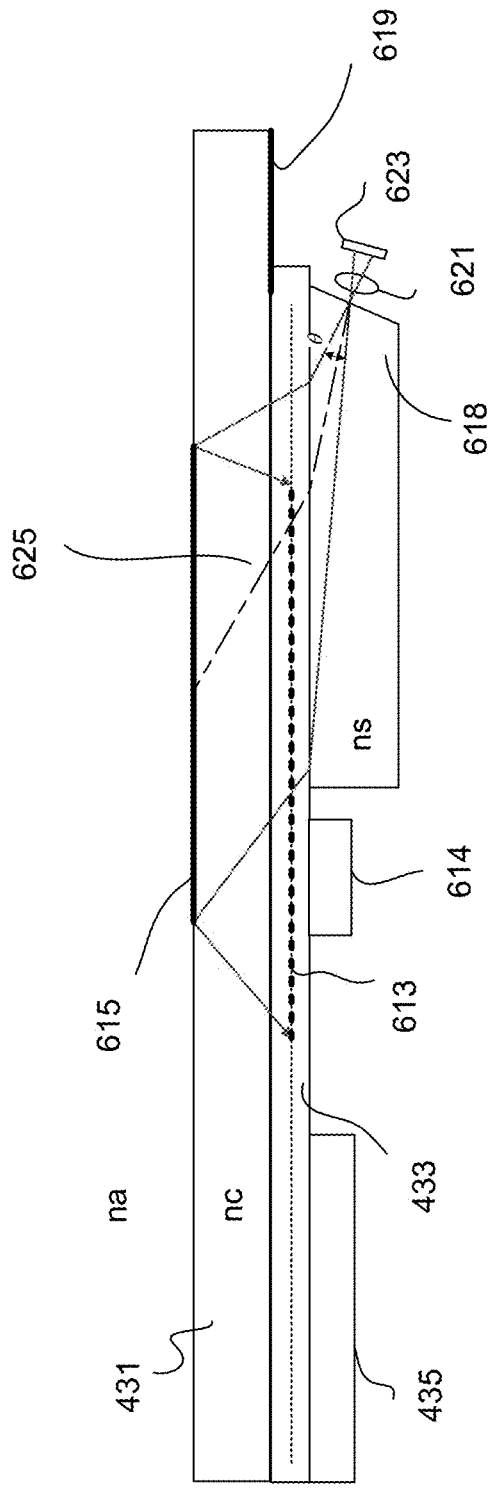
FIG. 9 shows another example of a under-screen optical sensor module based on the design in FIG. 7 where the viewing zone or the fingerprint illumination zone in the OLED display module is designed to include one or more extra light sources to provide additional illumination to the sensing zone.

FIG. 9 shows another example of a under-screen optical sensor module based on the design in FIG. 7 where the viewing zone or the fingerprint illumination zone 613 in the OLED display module 433 is designed to include one or more extra light sources 614 that are attached to or glued into the same position or region of the viewing zone 613 to provide additional illumination to the sensing zone 615, thus increasing the light intensity in optical sensing operations. This is one of ways for improving the optical sensing sensitivity. The extra light sources 614 may be of an expanded type, or be a collimated type so that all the points within the effective sensing zone 615 is illuminated. The extra light sources 614 may be a single element light source or an array of light sources. As mentioned above, the OLED pixels in the viewing zone or the fingerprint illumination zone 613 in the OLED display module 433 may be operated a higher brightness level during the optical fingerprint sensing operation above the brightness level used for displaying images in the OLED display.

FIGS. 10A-10B show an example of a under-screen optical sensor module that uses an optical coupler 628 shaped as a thin wedge to improve the optical detection at the optical sensor array 623. FIG. 10A shows a cross section of the device structure with an under-screen optical sensor module for fingerprint sensing and FIG. 10B shows a top view of the device screen. The optical wedge 628 (with a refractive index ns) is located below the display panel structure to modify a total reflection condition on a bottom surface of the display panel structure that interfaces with the optical wedge 628 to permit extraction of light out of the display panel structure through the bottom surface. The optical sensor array 623 receives the light from the optical wedge 628 extracted from the display panel structure and the optical imaging module 621 is located between the optical wedge 628 and the optical sensor array 623 to image the light from the optical wedge 628 onto the optical sensor array 623. In the illustrated example, the optical wedge 628 includes a slanted optical wedge surface facing the optical imaging module and the optical sensing array 623. Also, as shown, there is a free space between the optical wedge 628 and the optical imaging module 621.

If the light is totally reflected at the sensing surface of the cover glass 431, the reflectance is 100%, of the highest efficiency. However, the light will also be totally reflected at the OLED bottom surface 433b if it is parallel to the cover glass surfaces. The wedge coupler 628 is used to modify the local surface angle so that the light can be coupled out for the detection at the optical sensor array 623. The micro holes in the TFT layers of the OLED display module 431 provide the desired light propagation path for light to transmit through the OLED display module 431 for the under-screen optical sensing. The actual light transmission efficiency may gradually be reduced if the light transmission angle becomes too large or when the TFT layer becomes too thick. When the angle is close to the total reflection angle, namely about 41.8° when the cover glass refractive index is 1.5, the fingerprint image looks good. Accordingly, the wedge angle of the wedge coupler 628 may be adjusted to be of a couple of degrees so that the detection efficiency can be increased or optimized. If the cover glass' refractive index is selected to be higher, the total reflection angle becomes smaller. For example, if the cover glass is made of Sapphire which refractive index is about 1.76, the total reflection angle is about 34.62°. The detection light transmission efficiency in the display is also improved. Therefore, this design of using a thin wedge to set the detection angle to be higher than the total reflection angle, and/or to use high refractive index cover glass material to improve the detection efficiency.

In the under-screen optical sensor module designs in FIGS. 6A-10B, the sensing area 615 on the top transparent surface is not vertical or perpendicular to the detection axis 625 of the optical sensor module so that the image plane of the sensing area is also not vertical or perpendicular to the detection axis 625. Accordingly, the plane of the photodetector array 523 can be tilted relative the detection axis 625 to achieve high quality imaging at the photodetector array 623.

Figure 11:
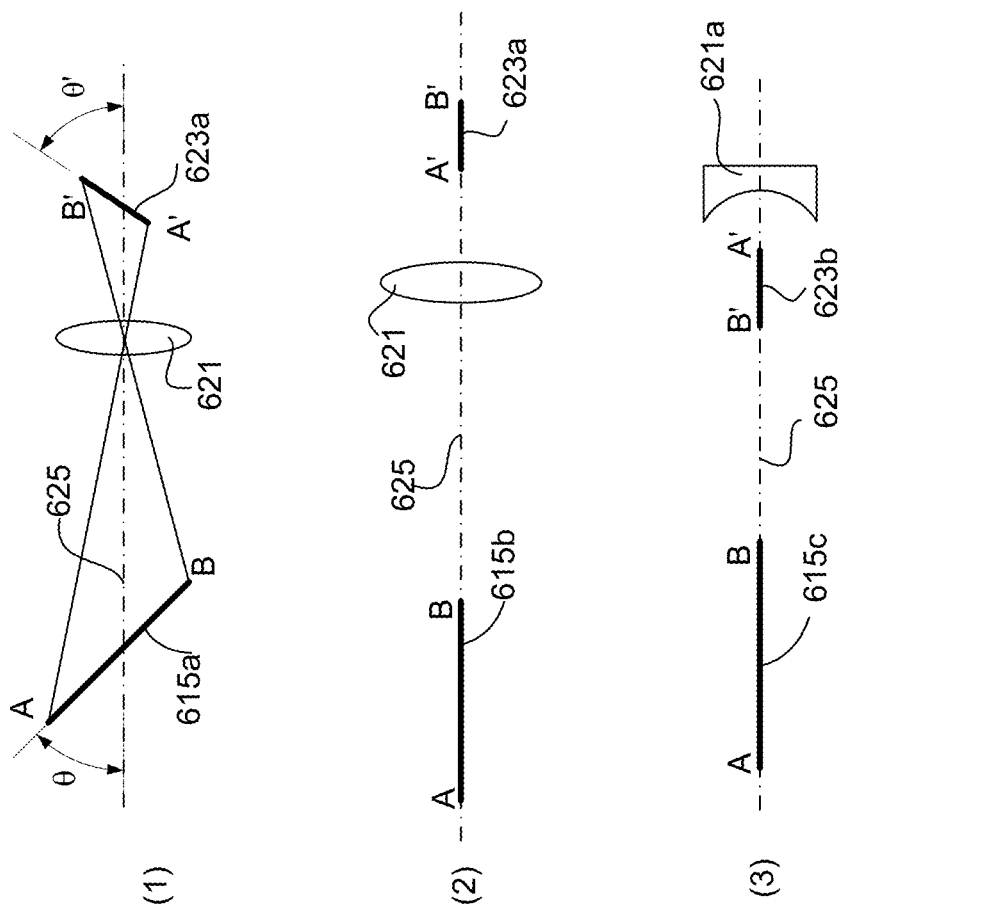
FIG. 11 shows imaging of the fingerprint sensing area on the top transparent layer via an imaging module under different tiling conditions where an imaging device images the fingerprint sensing area onto an optical sensor array and the imaging device may be optically transmissive or optically reflective.

FIG. 11 shows three example configurations for this tiling. FIG. 11 (1) shows the sensing area 615a is tilted and is not perpendicular the detection axis 625. In a specified case shown in (2), the sensing area 615b is aligned to be on the detection axis 625, its image plane will also be located on the detection axis 625. In practice, the lens 621 can be partially cut off so as to simplify the package. In various implementations, the micro lens 621 can also be of transmission type or reflection type. For example, a specified approach is illustrated in (3). The sensing area 615c is imaged by an imaging mirror 621a. A photodiode array 623b is aligned to detect the signals.

In the above designs where the lens 621 is used, the lens 621 can be designed to have an effective aperture that is larger than the aperture of the holes in the OLED display layers that allow transmission of light through the OLED display for optical fingerprint sensing. This design can reduce the undesired influence of the wiring structures and other scattering objects in the OLED display module.

In some implementations of the disclosed fingerprint technology, the fingerprint sensing contrast at the optical sensor array 623 can be improved by controlling the OLED pixels (613) of the display screen that provide the illumination for capturing the fingerprint patterns in the fingerprint touch sensing. When the fingerprint sensor is activated, e.g., due to presence of a touch, the OLED pixels in the local viewing zone 613 can be turned on with high brightness to improve the fingerprint sensing contrast. For example, the brightness of the OLED pixels in the local viewing zone 613 can be controlled to be higher than its maximum brightness when the same OLED pixels in the local viewing zone 613 are used as a regular display.

The under-screen optical sensing disclosed in this patent document can be adversely affected by noise from various factors including the background light from the environment in which a device is used. Various techniques for reducing the background light noise are provided.

For example, the undesired background light in the fingerprint sensing may be reduced by providing proper optical filtering in the light path. One or more optical filters may be used to reject the environment light wavelengths, such as near IR and partial of the red light etc. In some implementation, such optical filter coatings may be made on the surfaces of the optical parts, including the display bottom surface, prism surfaces, sensor surface etc. For example, human fingers absorb most of the energy of the wavelengths under ~580 nm, if one or more optical filters or optical filtering coatings can be designed to reject light in wavelengths from 580 nm to infrared, undesired contributions to the optical detection in fingerprint sensing from the environment light may be greatly reduced. More details on background reduction based on optical filtering are provided in later sections.

Figure 12:
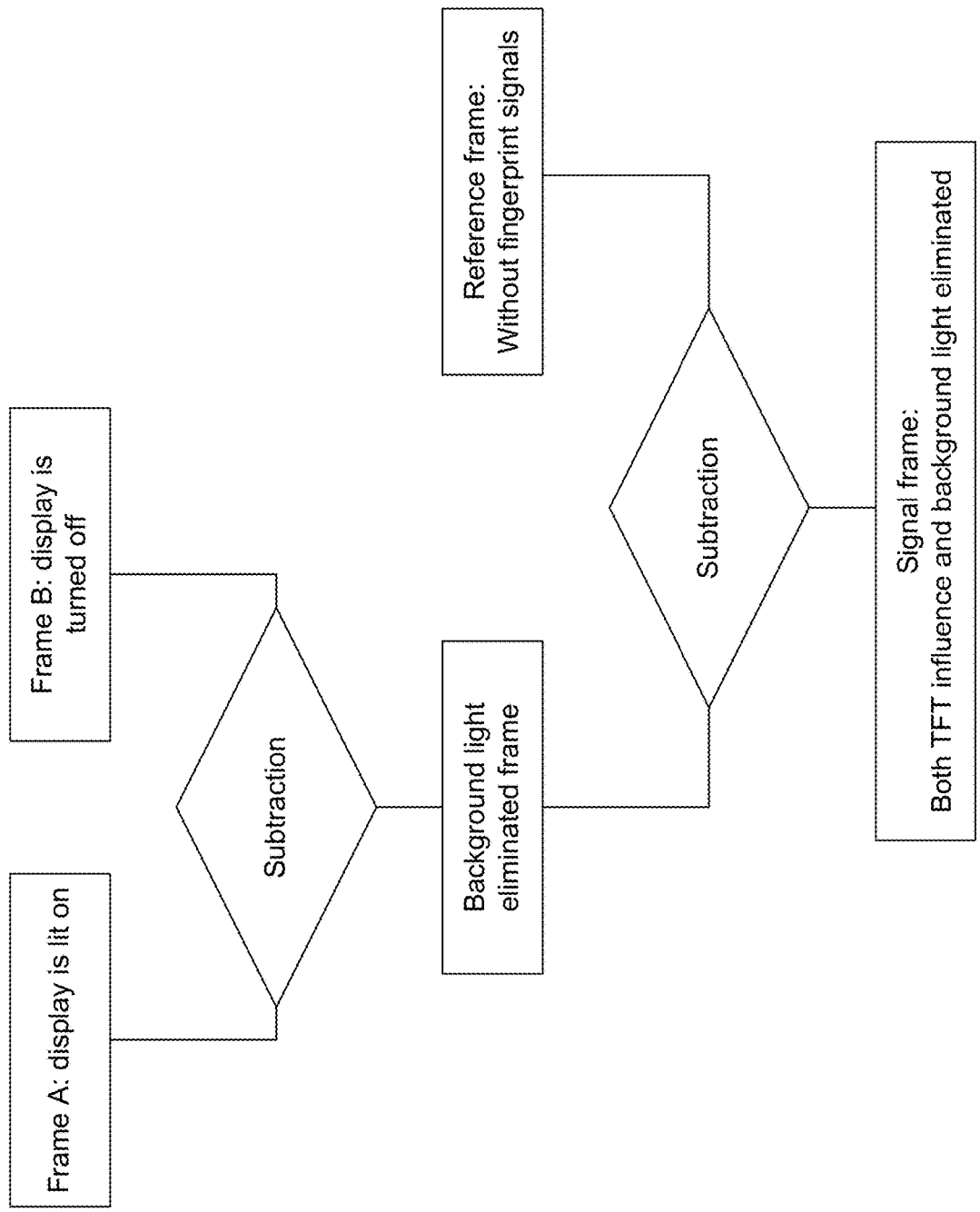
FIG. 12 shows an example of an operation of the fingerprint sensor for reducing or eliminating undesired contributions from the background light in fingerprint sensing.
Figure 13:
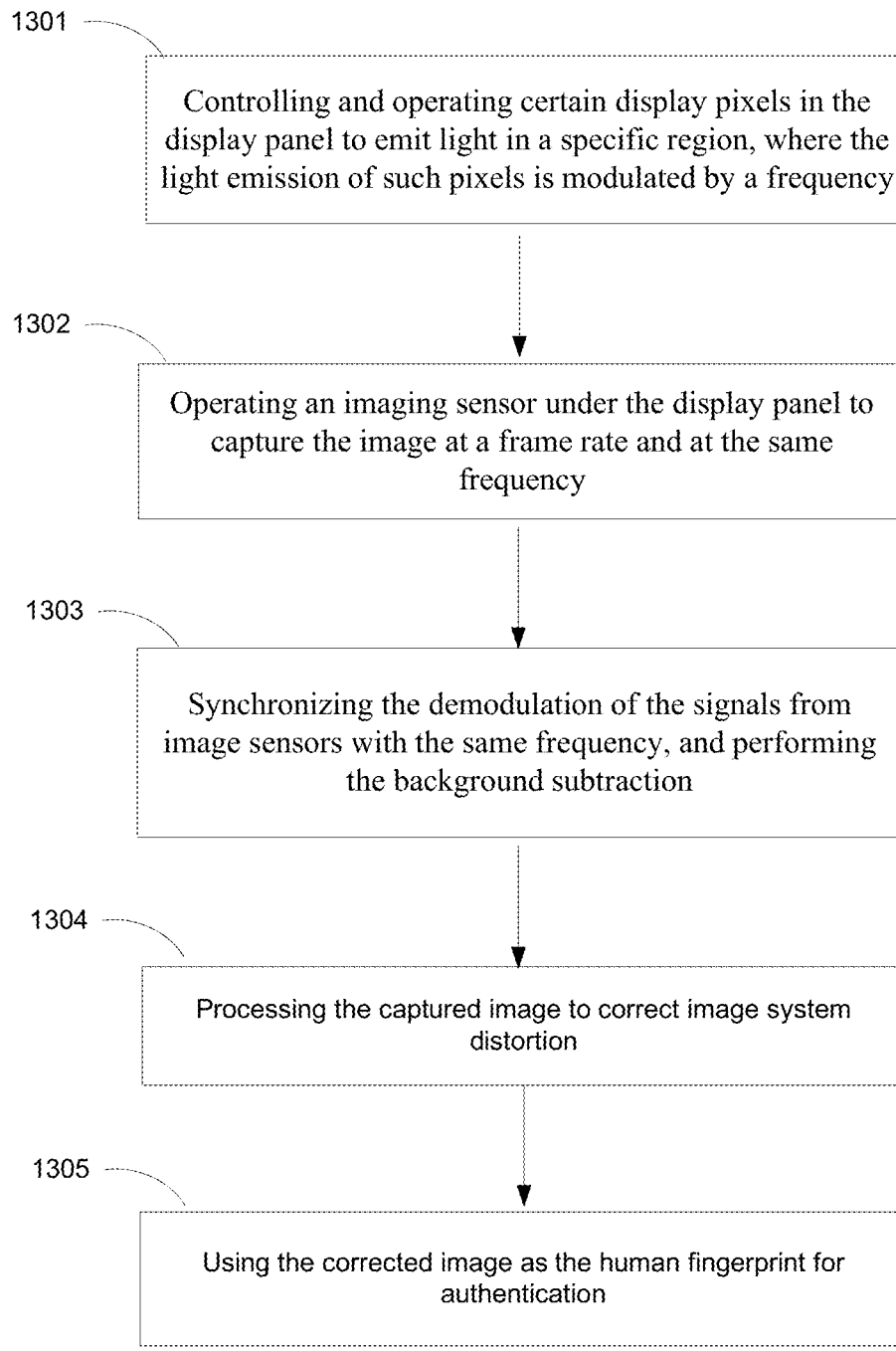
FIG. 13 shows a process for operating an under-screen optical sensor module for capturing a fingerprint pattern.

FIGS. 12 and 13 show two examples of techniques based on particularly ways of capturing and processing optical signals at the optical sensor module.

FIG. 12 shows an example of an operation of the fingerprint sensor for reducing or eliminating undesired contributions from the background light in fingerprint sensing. The optical sensor array can be used to capture various frames and the captured frames can be used to perform differential and averaging operations among multiple frames to reduce the influence of the background light. For example, in frame A the OLED display is turned on to illuminate the finger touching area, in frame B the illumination is changed or turned off. Subtraction of the signals of frame B from the signals of frame A can be used in the image processing to reduce the undesired background light influence.

FIG. 13 shows an example of an operation process for correcting the image distortion in the optical sensor module. At step 1301, certain display pixels are controlled and operated to emit light in a specific region, and the light emission of such pixels is modulated by a frequency F. At step 1302, an imaging sensor under the display panel is operated to capture the image at a frame rate at the same frequency F. In the optical fingerprint sensing operation, a finger is placed on top of the display panel cover substrate and the presence of the finger modulates the light reflection intensity of the display panel cover substrate top surface. The imaging sensor under the display captures the fingerprint modulated reflection light pattern. At step 1303, the demodulation of the signals from image sensors is synchronized with the frequency F, and the background subtraction is performed. The resultant image has a reduced background light effect and includes images from pixel emitting lights. At step 1304, the capture image is processed and calibrated to correct image system distortions. At step 1305, the corrected image is used as a human fingerprint image for user authentication.

The same optical sensors used for capturing the fingerprint of a user can be used also to capture the scattered light from the illuminated finger as shown by the back scattered light 191 in FIGS. 5A and 5B. The detector signals from the back scattered light 191 in FIGS. 5A and 5B in a region of interest can be integrated to produce an intensity signal. The intensity variation of this intensity signal is evaluated to determine the heart rate of the user.

The above fingerprint sensor may be hacked by malicious individuals who can obtain the authorized user's fingerprint, and copy the stolen fingerprint pattern on a carrier object that resembles a human finger. Such unauthorized fingerprint patterns may be used on the fingerprint sensor to unlock the targeted device. Hence, a fingerprint pattern, although a unique biometric identifier, may not be by itself a completely reliable or secure identification. The under-screen optical sensor module can also be used to as an optical anti-spoofing sensor for sensing whether an input object with fingerprint patterns is a finger from a living person and for determining whether a fingerprint input is a fingerprint spoofing attack. This optical anti-spoofing sensing function can be provided without using a separate optical sensor. The optical anti-spoofing can provide high-speed responses without compromising the overall response speed of the fingerprint sensing operation.

Figure 14A:
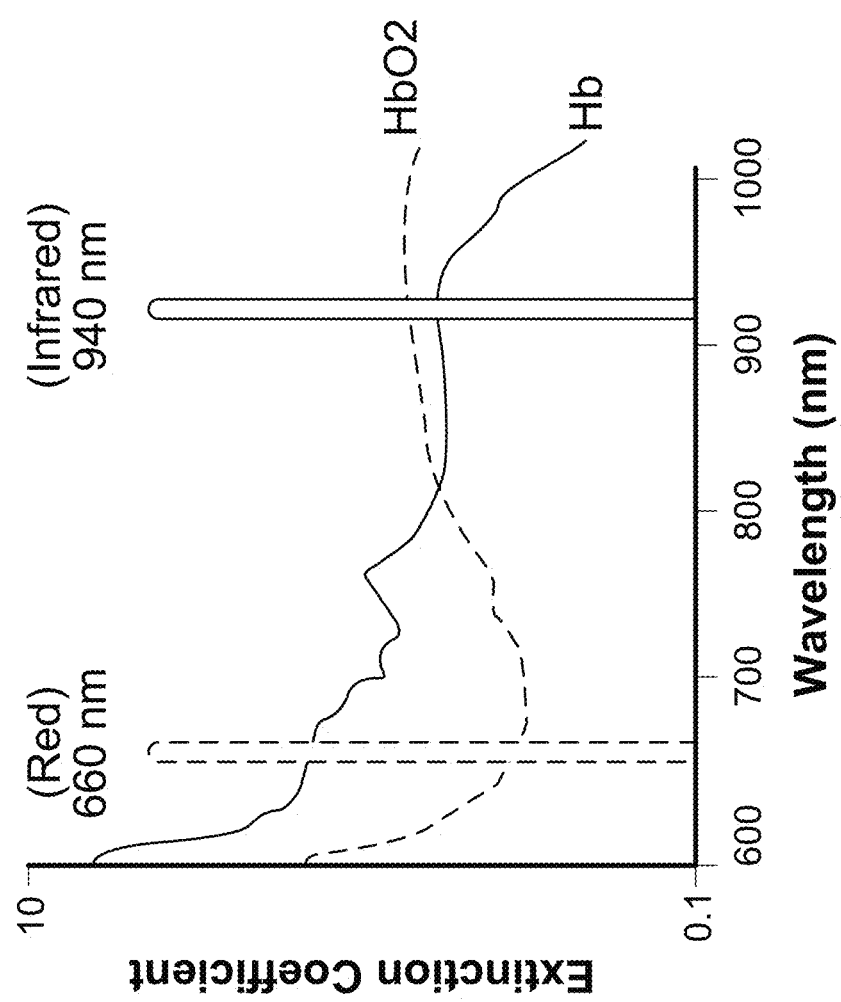
FIG. 14A shows exemplary optical extinction coefficients of materials being monitored in blood where the optical absorptions are different between the visible spectral range.

FIG. 14A shows exemplary optical extinction coefficients of materials being monitored in blood where the optical absorptions are different between the visible spectral range e.g., red light at 660 nm and the infrared range, e.g., IR light at 940 nm. By using probe light to illuminate a finger at a first visible wavelength (Color A) and a second different wavelength such as an IR wavelength (Color B), the differences in the optical absorption of the input object can be captured determine whether the touched object is a finger from a live person. Since the OLED pixels include OLED pixels emitting light of different colors to emit probe light at least two different optical wavelengths to use the different optical absorption behaviors of the blood for live finger detection. When a person' heart beats, the pulse pressure pumps the blood to flow in the arteries, so the extinction ratio of the materials being monitored in the blood changes with the pulse. The received signal carries the pulse signals. These properties of the blood can be used to detect whether the monitored material is a live-fingerprint or a fake fingerprint.

Figure 14B:
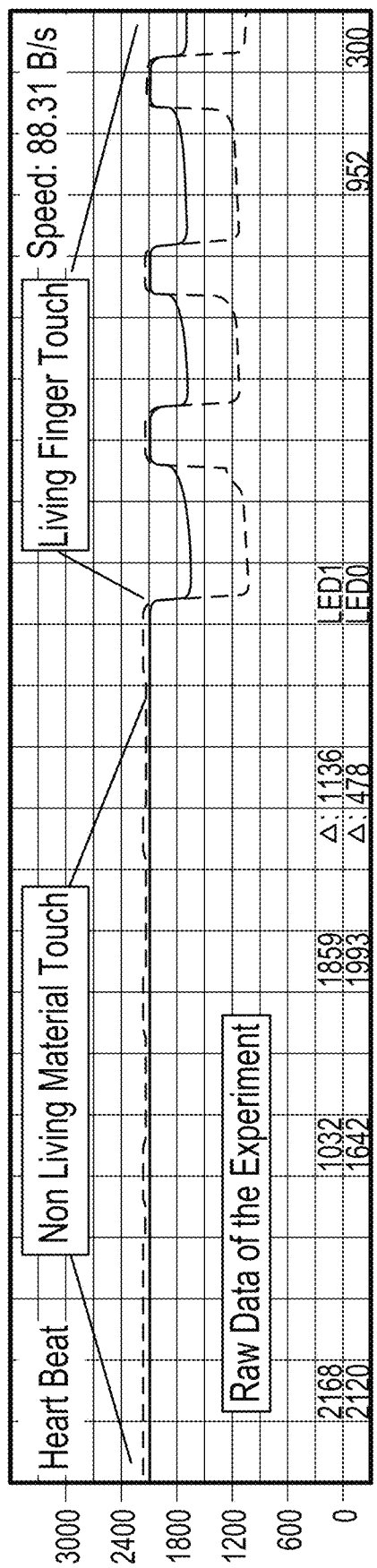
FIG. 14B shows a comparison between optical signal behaviors in the reflected light from a nonliving material and a live finger.

FIG. 14B shows a comparison between optical signal behaviors in the reflected light from a nonliving material (e.g., a fake finger) and a live finger. The optical fingerprint sensor can also operate as a heartbeat sensor to monitor a living organism. When two or more wavelengths of the probe light are detected, the extinction ratio difference can be used to quickly determine whether the monitored material is a living organism, such as live fingerprint. In the example shown in FIG. 14B, probe light at different wavelengths were used, one at a visible wavelength and another at an IR wavelength as illustrated in FIG. 14A.

When a nonliving material touches the top cover glass above the fingerprint sensor module, the received signal reveals strength levels that are correlated to the surface pattern of the nonliving material and the received signal does not contain signal components associated with a finger of a living person. However, when a finger of a living person touches the top cover glass, the received signal reveals signal characteristics associated with a living person, including obviously different strength levels because the extinction ratios are different for different wavelengths. This method does not take long time to determine whether the touching material is a part of a living person. In FIG. 14B, the pulse-shaped signal reflects multiple touches instead of blood pulse. Similar multiple touches with a nonliving material does not show the difference caused by a living finger.

This optical sensing of different optical absorption behaviors of the blood at different optical wavelengths can be performed in a short period for live finger detection and can be faster than optical detection of a person's heart beat using the same optical sensor.

Figure 15:
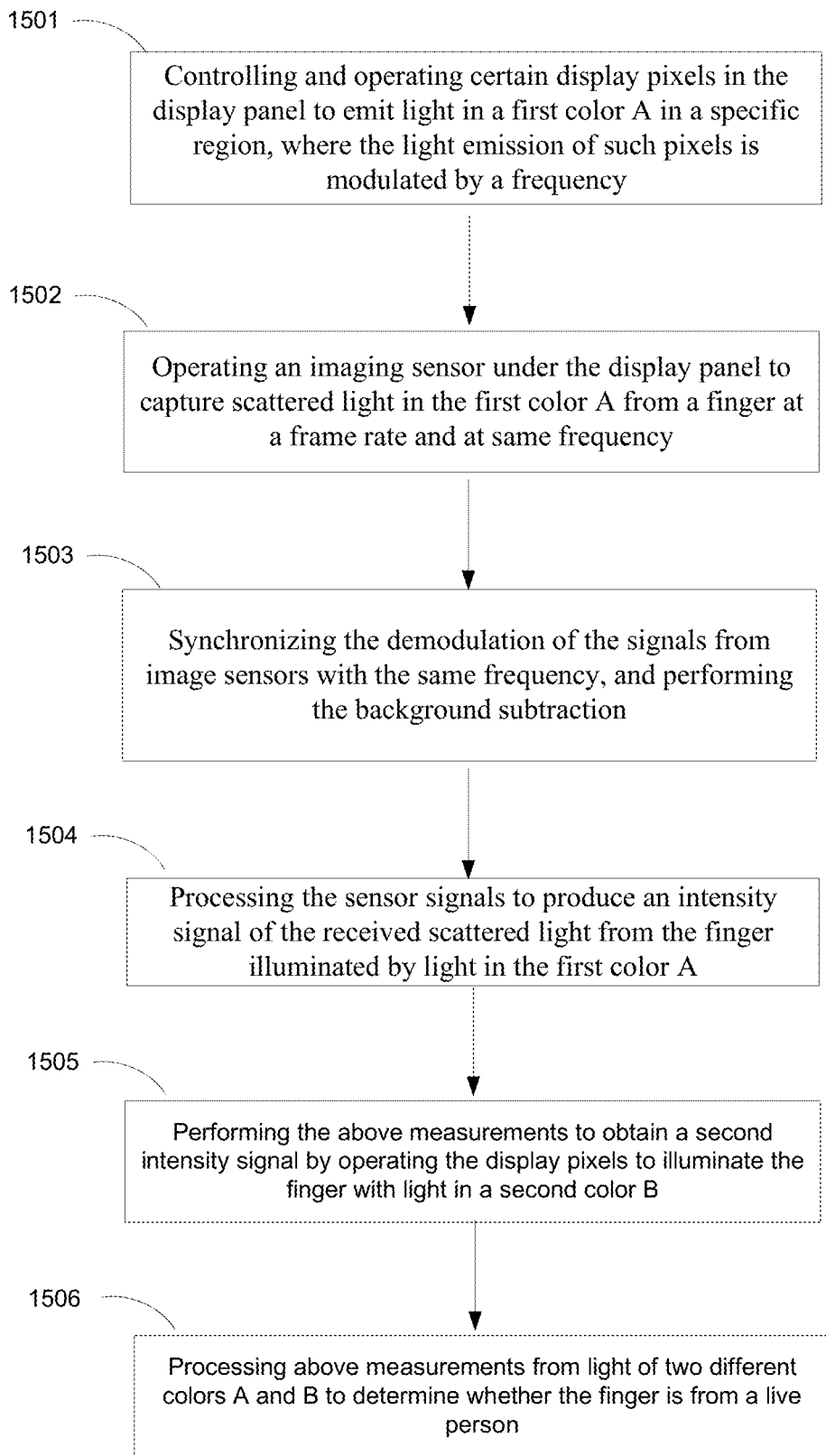
FIG. 15 shows an example of an operation process for determining whether an object in contact with the OLED display screen is part of a finger of a live person by operating the OLED pixels to illuminate the finger in two different light colors.

FIG. 15 shows an example of an operation process for determining whether an object in contact with the OLED display screen is part of a finger of a live person by operating the OLED pixels to illuminate the finger in two different light colors.

For yet another example, the disclosed optical sensor technology can be used to detect whether the captured or detected pattern of a fingerprint or palm is from a live person's hand by a "live finger" detection mechanism by other mechanisms other than the above described different optical absorptions of blood at different optical wavelengths. For example, a live person's finger tends to be moving or stretching due to the person's natural movement or motion (either intended or unintended) or pulsing when the blood flows through the person's body in connection with the heartbeat. In one implementation, the optical sensor module can detect a change in the returned light from a finger or palm due to the heartbeat/blood flow change and thus to detect whether there is a live heartbeat in the object presented as a finger or palm. The user authentication can be based on the combination of the both the optical sensing of the fingerprint/palm pattern and the positive determination of the presence of a live person to enhance the access control. For yet another example, as a person touches the OLED display screen, a change in the touching force can be reflected in one or more ways, including fingerprint pattern deforming, a change in the contacting area between the finger and the screen surface, fingerprint ridge widening, or a blood flow dynamics change. Those and other changes can be measured by optical sensing based on the disclosed optical sensor technology and can be used to calculate the touch force. This touch force sensing can be used to add more functions to the optical sensor module beyond the fingerprint sensing.

Figure 16:
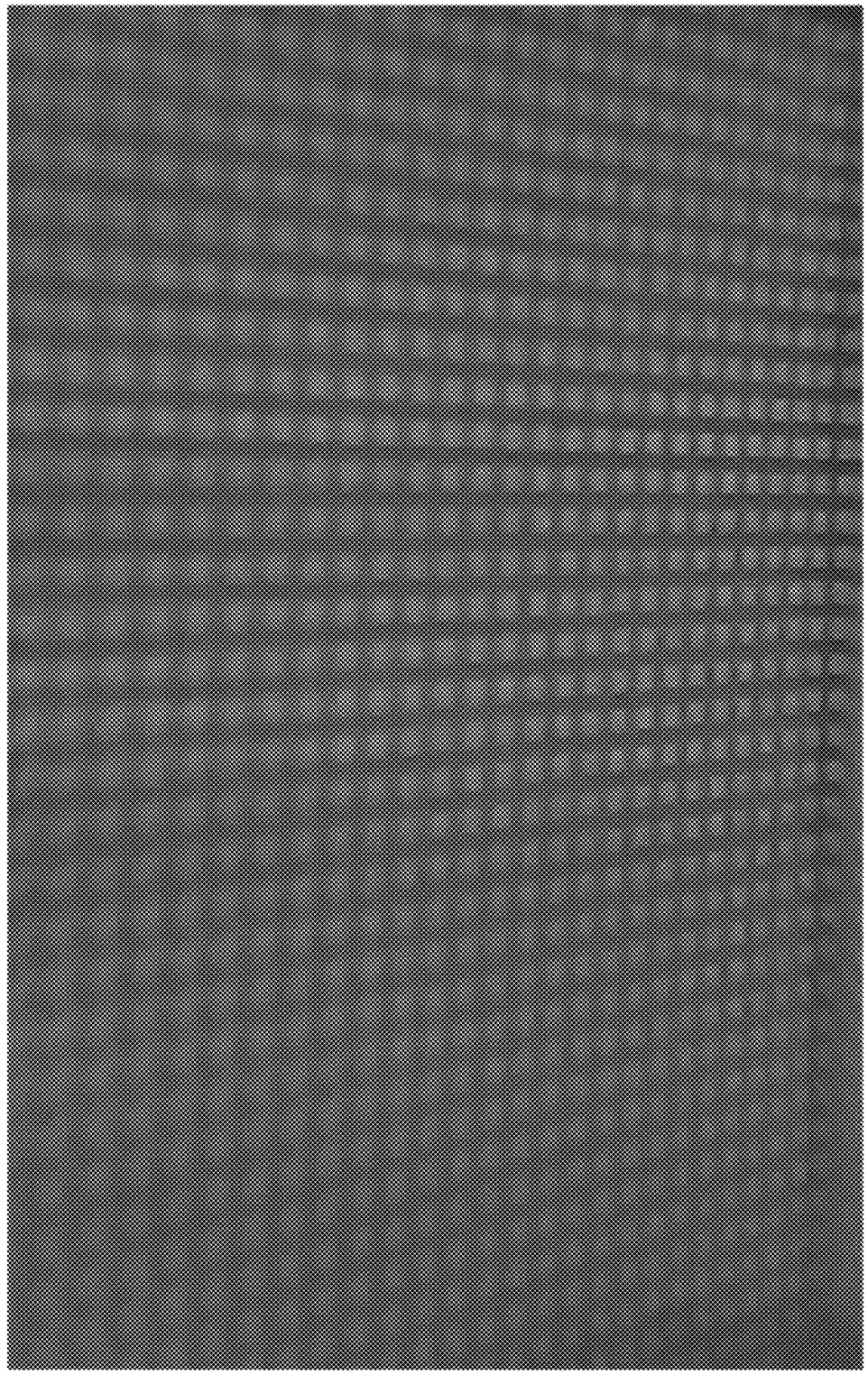
FIG. 16 shows an example of a standard calibration pattern produced by the OLED display for calibrating the imaging sensing signals output by the optical sensor array for fingerprint sensing.

In the above examples where the fingerprint pattern is captured on the optical sensor array via an imaging module as in FIG. 4B and FIG. 6B, optical distortions tend to degrade the image sensing fidelity. Such optical distortions can be corrected in various ways. FIG. 16 shows an example of a standard calibration pattern produced by the OLED display for calibrating the imaging sensing signals output by the optical sensor array for fingerprint sensing. The fingerprint sensing module calibrates the output coordinates referencing on the image of the standard pattern.

In light of the disclosure in this patent document, various implementations can be made for the optical sensor module as disclosed.

For example, a display panel can be constructed in which each pixel emitting lights, and can be controlled individually; the display panel includes an at least partially transparent substrate; and a cover substrate, which is substantially transparent. An optical sensor module is placed under the display panel to sense the images form on the top of the display panel surface. The optical sensor module can be used to sense the images form from light emitting from display panel pixels. The optical sensor module can include a transparent block with refractive index lower than the display panel substrate, and an imaging sensor block with an imaging sensor array and an optical imaging lens. In some implementations, the low refractive index block has refractive index in the range of 1.35 to 1.46 or 1 to 1.35.

For another example, a method can be provided for fingerprint sensing, where light emitting from a display panel is reflected off the cover substrate, a finger placed on top of the cover substrate interacts with the light to modulate the light reflection pattern by the fingerprint. An imaging sensing module under the display panel is used to sense the reflected light pattern image and reconstruct fingerprint image. In one implementation, the emitting light from the display panel is modulated in time domain, and the imaging sensor is synchronized with the modulation of the emitting pixels, where a demodulation process will reject most of the background light (light not from pixels being targeted).

Various design considerations for the disclosed under-screen optical sensor module for optical fingerprint sensing are further described in in the International Patent Application No. PCT/US2016/038445 entitled "MULTIFUNCTION FINGERPRINT SENSOR HAVING OPTICAL SENSING CAPABILITY" filed on Jun. 20, 2016 (claiming priority from U.S. Provisional Patent Application No. 62/181,718, filed on Jun. 18, 2015 and published under International Publication No. WO 2016/205832 A1 on Dec. 22, 2016) and International Patent Application No. PCT/CN2016/104354 entitled "MULTIFUNCTION FINGERPRINT SENSOR HAVING OPTICAL SENSING AGAINST FINGERPRINT SPOOFING" filed on Nov. 2, 2016 (claiming priority from U.S. Provisional Patent Application No. 62/249,832, filed on Nov. 2, 2015 and published under International Publication No. WO 2017/076292 A1). The entire disclosures of the above mentioned patent applications are incorporated by reference as part of the disclosure of this patent document.

In various implementations of the under-screen optical sensor module technology for fingerprint sensing disclosed herein, the optical imaging of the illuminated touched portion of a finger to the optical sensor array in the under-screen optical sensor module can be achieved without using an imagine module such as a lens by imaging the returned light from the touched portion of the finger under optical illumination. One technical challenge for optical fingerprint sensing without an imaging module is how to control the spreading of the returned light that may spatially scramble returned light from different locations on the touched portion of the finger at the optical sensor array so that the spatial information of different locations may be lost when such returned light reaches the optical sensor array. This challenge can be addressed by using optical collimators or an array of pinholes to replace the optical imaging module in the under-screen optical sensor module for detecting a fingerprint by optical sensing. A device for implementing such optical fingerprint sending can include a device screen that provides touch sensing operations and includes a display panel structure having light emitting display pixels, each pixel operable to emit light for forming a portion of a display image; a top transparent layer formed over the device screen as an interface for being touched by a user for the touch sensing operations and for transmitting the light from the display structure to display images to a user; and an optical sensor module located below the display panel structure to receive light that is emitted by at least a portion of the light emitting display pixels of the display structure and is returned from the top transparent layer to detect a fingerprint, the optical sensor module including an optical sensor array that receives the returned light and an array of optical collimators or pinholes located in a path of the returned light to the optical sensor array. The array of optical collimators are used to collect the returned light from the display panel structure and to separate light from different locations in the top transparent layer while directing the collected returned light to the optical sensor array.

The imaging by using collimators relies on using different collimators at different locations to spatially separate light from different regions of a fingerprint to different optical detectors in the optical detector array. The thickness or length of each collimator along the collimator can be designed to control the narrow field of optical view of each collimator, e.g., the light from only a small area on the illuminated finger is captured by each collimator and is projected onto a few adjacent optical detectors in the optical detector array. As an example, the thickness or length of each collimator along the collimator can be designed to be large, e.g., a few hundred microns, so that the field of optical view of each collimator may allow the collimator to deliver imaging light to a small area on the optical detector array, e.g., one optical detector or a few adjacent optical detectors in the optical detector array (e.g., an area of tens of microns on each side on the optical detector array in some cases).

The following sections explain how an array of optical collimators or pinholes can be used for under-screen optical fingerprint sensing by the examples for using optical collimators in optical fingerprint sensing in hybrid sensing pixels each having a capacitive sensor for capturing fingerprint information and an optical sensor for capturing fingerprint information.

Figure 17A:
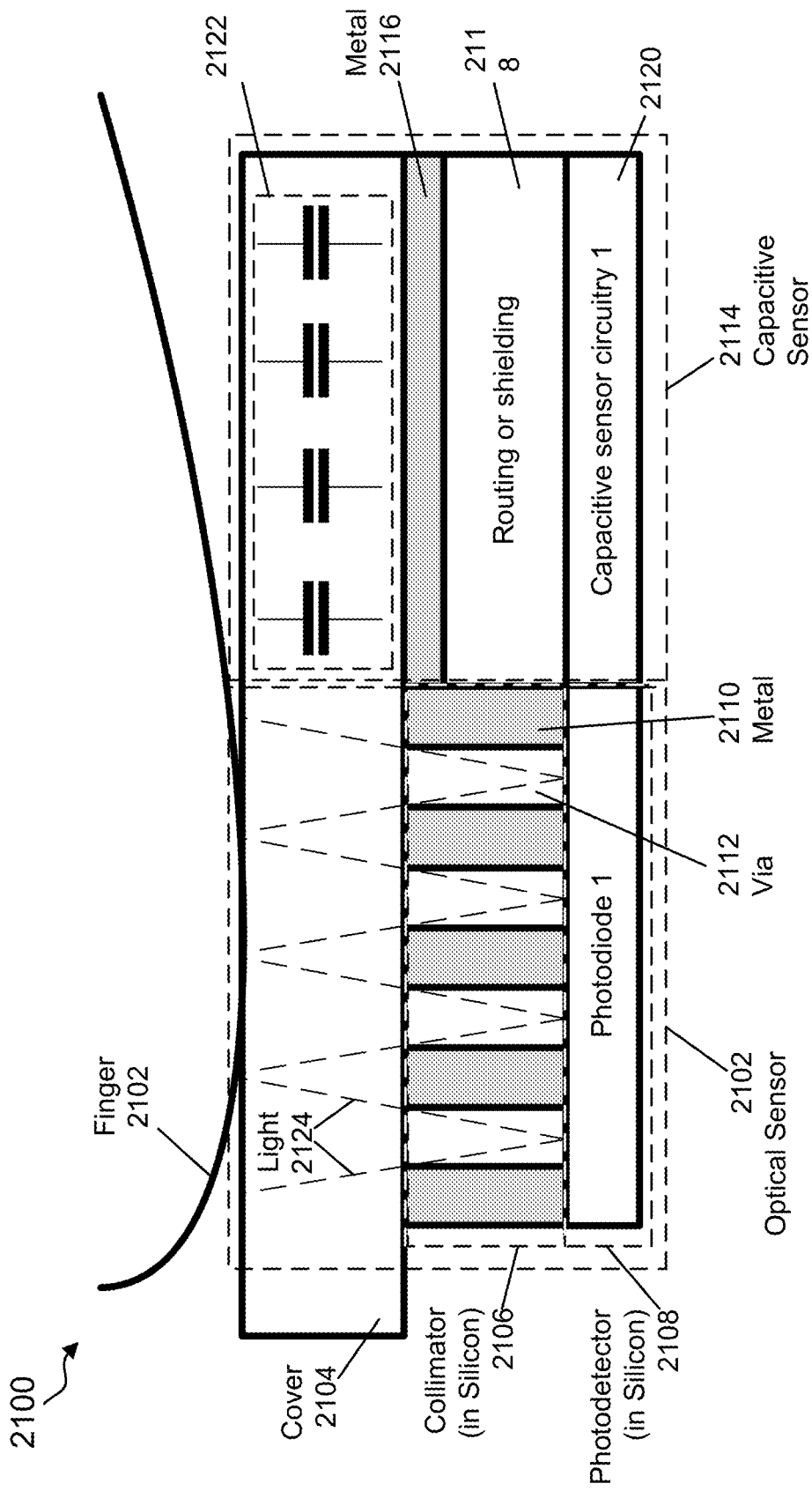
FIGS. 17A and 17B show two examples of hybrid sensing pixel designs that combine capacitive sensing and optical sensing within the same sensing pixel.
Figure 17B:
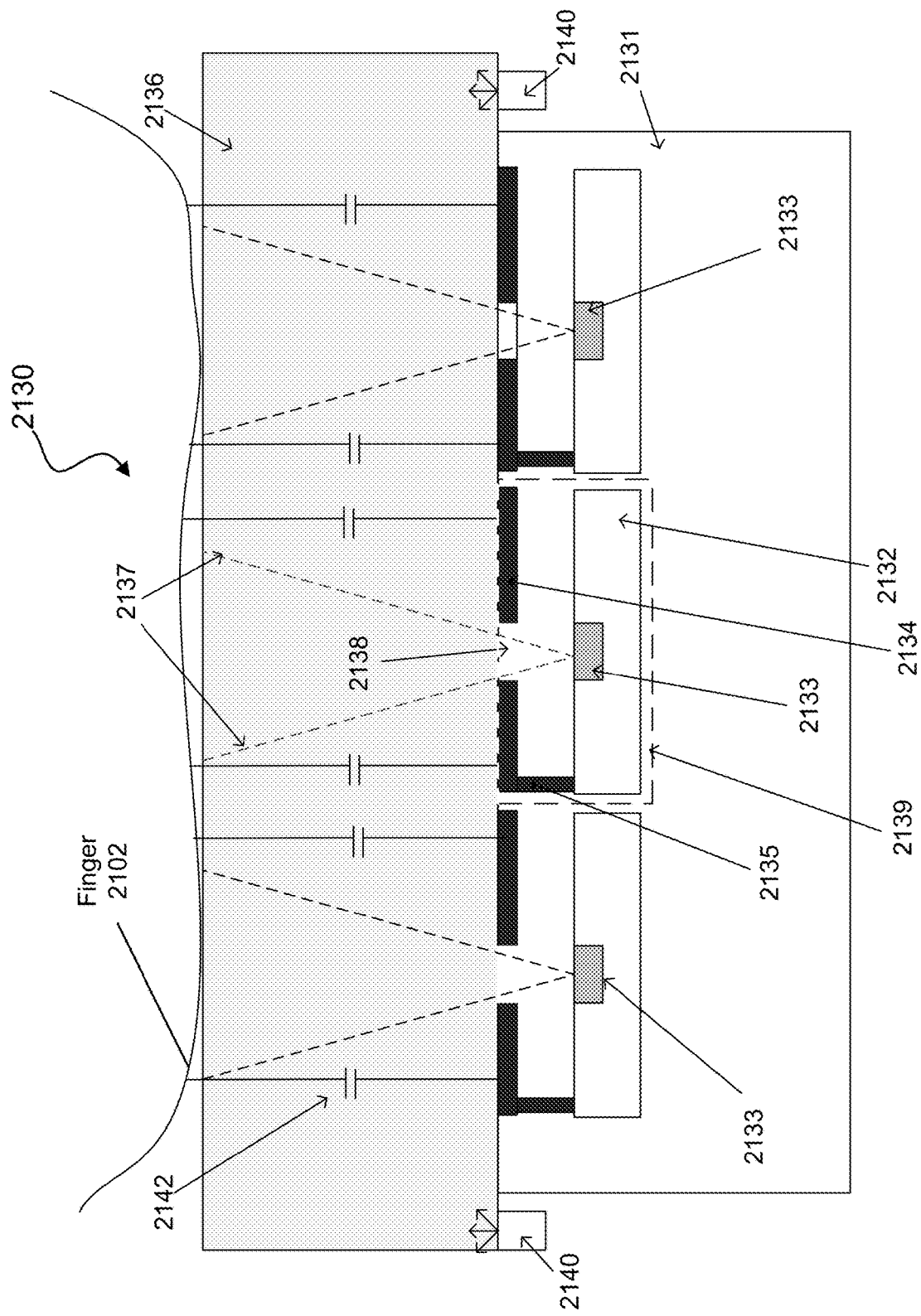

FIGS. 17A and 17B show two examples of hybrid sensing pixel designs that combine capacitive sensing and optical sensing within the same sensing pixel.

FIG. 17A shows an example of a fingerprint sensor device 2100 that incorporates a capacitive sensor in addition to an optical sensor for each sensor pixel of an array of sensor pixels in capturing fingerprint information. By combining both capacitive sensors and optical sensors, fingerprint images obtained with the optical sensors can be used to better resolve the 3D fingerprint structure obtained with the capacitive sensors. For illustrative purposes, the structure shown in FIG. 17A represents one sensor pixel in an array of sensor pixels and each sensor pixel includes an optical sensor 2102 and a capacitive sensor 2114 that are disposed next to each other within the same pixel.

The optical sensor 2102 includes a photodetector 2108 and a collimator 2106 disposed over the photodetector 2108 to narrow or focus reflected light 2124 from finger 2102 toward the photodetector 2108. One or more light sources, such as LEDs (not shown) can be disposed around the collimator 2106 to emit light, which is reflected off the finger as reflected light 2124 and is directed or focused toward the corresponding photodetector 2108 to capture a part of the fingerprint image of the finger 2102. The collimator 2106 can be implemented using an optical fiber bundle or one or more metal layer(s) with holes or openings. This use of multiple optical collimators above the optical detector array may be used as a lensless optical design for capturing the fingerprint image with a desired spatial resolution for reliable optical fingerprints sensing. FIG. 17A shows the collimator 2106 implemented using one or more metal layers 2110 with holes or openings 2112. The collimator 2106 in the layer between the top structure or layer 2104 and the photodetectors 2108 in FIG. 17A includes multiple individual optical collimators formed by optical fibers or by holes or openings in one or more layers (e.g., silicon or metal) and each of such individual optical collimators receives light ray 2124 in a direction along the longitudinal direction of each optical collimator or within a small angle range that can be captured by the top opening of each opening or hole and by the tubular structure as shown so that light rays incident in large angles from the longitudinal direction of each optical collimator are rejected by each collimator from reaching the optical photodiode on the other end of the optical collimator.

In the capacitive sensing part of each sensing pixel, the capacitive sensor 2114 includes a capacitive sensor plate 2116 that is electromagnetically coupled to a portion of a finger that is either nearby or in contact with the sensing pixel to perform the capacitive sensing. More specifically, the capacitive sensor plate 2116 and the finger 2102 interact as two plates of one or more capacitive elements 2122 when the finger 2102 is in contact with or substantially near the optional cover 2104 or a cover on a mobile device that implements the fingerprint sensor device 2100. The number of capacitive sensor plates 2116 can vary based on the design of the capacitive sensor 2114. The capacitive sensor plate 2116 can be implemented using one or more metal layers. The capacitive sensor plate 2116 is communicatively coupled to capacitive sensor circuitry 2120 so that the capacitive sensor circuitry 2120 can process the signals from the capacitive sensor plate 2116 to obtain data representing the 3D fingerprint structure. A routing or shielding material can be disposed between the capacitive sensor plate 2116 and the capacitive sensor circuitry to electrically shield the metal plate 2116. The capacitive sensor circuitry 2120 can be communicatively coupled to both the capacitive sensor plate 2116 and the photodetector 2108 to process both the signal from the capacitive sensor plate 2116 and the signal from the photodetector 2108. In FIG. 17A, the capacitive sensor and the optical sensor within each hybrid sensing pixel are adjacent to and displaced from each other without being spatially overlapped.

In implementations, the optical sensing features in the hybrid sensor design in FIG. 17A such as the optical collimator design can be used in a under-screen optical sensor module. Therefore, the optical sensing with the optical collimator feature in FIG. 17A may be implemented in a mobile device or an electronic device is capable of detecting a fingerprint by optical sensing to include a display screen structure; a top transparent layer formed over the display screen structure as an interface for being touched by a user and for transmitting the light from the display screen structure to display images to a user; and an optical sensor module located below the display screen structure to receive light that is returned from the top transparent layer to detect a fingerprint. The optical sensor module includes an optical sensor array of photodetectors that receive the returned light and an array of optical collimators to collect the returned light from the top transparent layer via the display screen structure and to separate light from different locations in the top transparent layer while directing the collected returned light through the optical collimators to the photodetectors of the optical sensor array.

FIG. 17B illustrates another example of a fingerprint sensor device 2130 that structurally integrates an optical sensor and a capacitive sensor in each hybrid sensor pixel in a spatially overlap configuration in an array of sensor pixels to reduce the footprint of each hybrid sensing pixel. The fingerprint sensor device 2130 includes a semiconductor substrate 2131, such as silicon. Over the substrate 2131, multiple sensing elements or sensing pixels 2139 are disposed. Each sensing element or sensing pixel 2139 includes active electronics circuitry area 2132 including CMOS switches, amplifier, resistors and capacitors for processing sensor signals. Each sensing pixel or sensing element 2139 includes a photodetector 2133 disposed or embedded in the active electronics circuitry area 2132. A capacitive sensor plate or a top electrode 2134 of the capacitive sensor for capacitive sensing is disposed over a photodetector 2133 and includes a hole or opening 2138 on the sensor plate 2134 to function also as a collimator of light for directing light onto the photodetector 2133. A via 2135 filled with conductive material is disposed to electrically connect the top electrode 2134 to the active circuit elements 2132. By adjusting the opening or the hole and the distance of the top electrode 2134 with the photodetector 2133, the light collecting angle 2137 of the photodetector (e.g., photodiode) 2133 can be adjusted. The fingerprint sensor device 2130 is covered by a protective cover 2136, which includes hard materials, such as sapphire, glass etc. Photodetector 2133 light collection angle 2137 can be designed to preserve the spatial resolution of the image collected by the photodiode arrays. A light source 2140, such as an LED, is placed under the cover, on the side of fingerprint sensor device 2130 to emit light, which is reflected off the finger and directed toward the photodetector 2133 to capture the fingerprint image. When a finger touches or comes substantially near the protective cover, the finger and the sensing top electrode 2134 in combination form a capacitive coupling (e.g., capacitor 2142) between the human body and sensing top electrode 2134. The fingerprint sensor device 2130 that includes both optical and capacitive sensors can acquire images of both a light reflection image of fingerprint and also a capacitive coupling image. The sensing top electrode 2134 serves dual purpose: 1) for capacitive sensing, and 2) as a collimator (by fabricating one or more holes on the sensing top electrode 2134) to direct, narrow or focus reflected light from the finger toward the photodetector 2133. Reusing the sensing top electrode 2134 eliminates the need for additional metal layer or optical fiber bundle, and thus reduces each pixel size and accordingly the overall size of the fingerprint sensor device 2130.

In FIG. 17B, the optical sensing design uses the holes or openings 2138 formed between the top layer 2136 and the bottom array of photodetectors 2133 as an optical collimators to select only light rays within certain angles 2137 to preserve the spatial resolution of the image collected by the photodetectors 2133 in the photodetector array as illustrated. Similar to the fiber or other tubular shaped optical collimators in FIG. 17A, the holes or openings 2138 formed between the top layer 2136 and the bottom array of photodetectors 2133 constitute optical collimators to collect the returned light from the top transparent layer via the display screen structure and to separate light from different locations in the top transparent layer while directing the collected returned light through the optical collimators to the photodetectors 2133.

Figure 18:
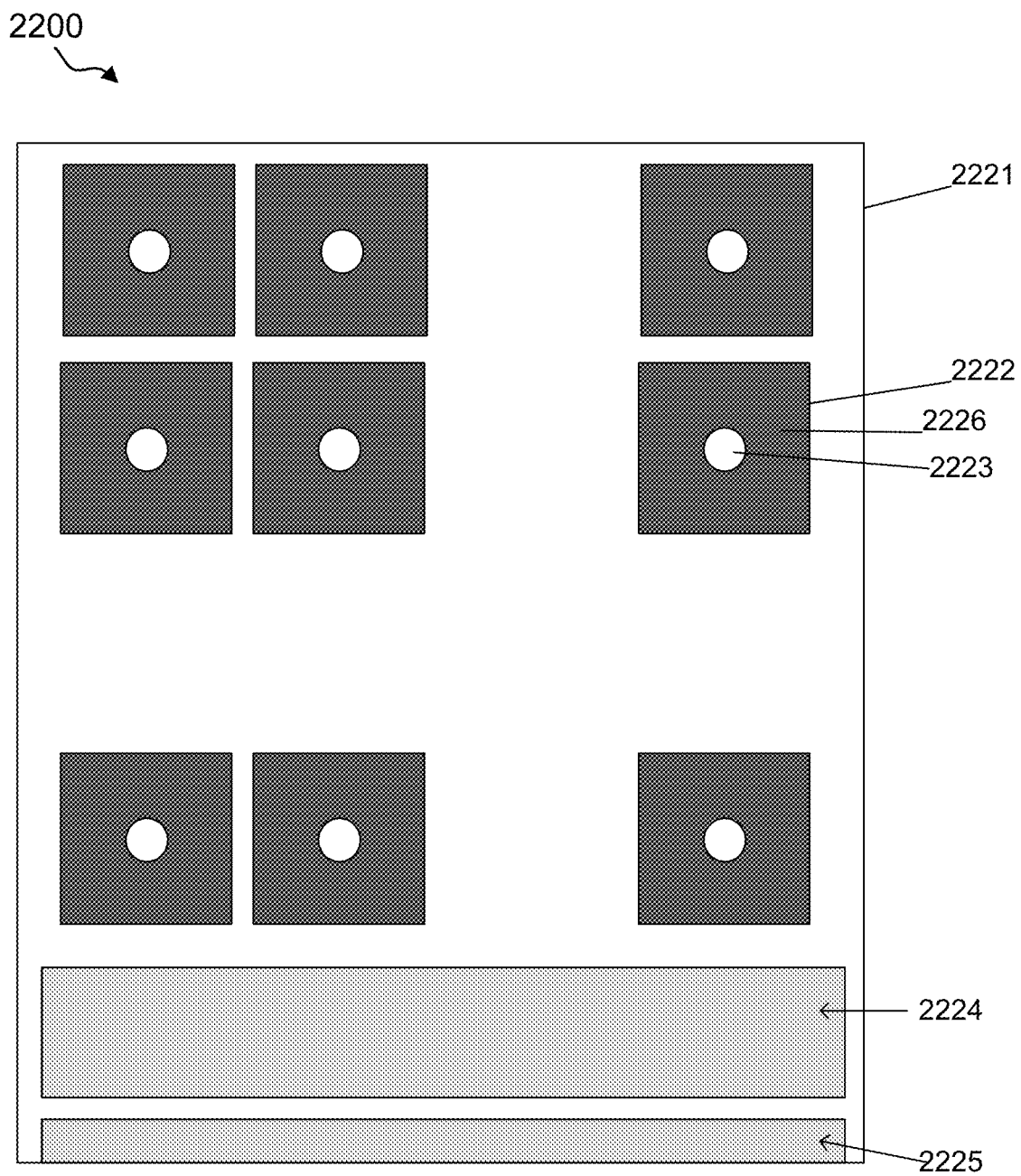
FIG. 18 is a top-down view of an exemplary hybrid fingerprint sensor device 2200 incorporating both an optical sensor and a capacitive sensor in each hybrid sensing pixel.

FIG. 18 is a top-down view of an exemplary hybrid fingerprint sensor device 2200 incorporating both an optical sensor and a capacitive sensor in each hybrid sensing pixel. The fingerprint sensor device 2200 is implemented as a CMOS silicon chip 2221 that includes an array of hybrid (incorporating both an optical sensor and a capacitive sensor) sensing elements or pixels 2222. Alternatively, the layout in FIGS. 22A-22B can also be for all optical sensing designs disclosed in this document where the openings or holes 2223 represent the optical collimators in FIG. 17A or 17B. The size or dimension of the sensing elements can be in the range of 25 μm to 250 μm, for example. The hybrid sensor device 2200 can include an array of support circuitry including amplifiers, ADCs, and buffer memory in a side region 2224. In addition, the hybrid sensor device 2200 can include an area for wire bonding or bump bonding 2225. A top layer 2226 of the hybrid sensor element 2222 can include a metal electrode for capacitive sensing. One or more openings or holes 2223 can be fabricated on each top metal electrode 23 to structurally serve as a collimator for directing light in a vertical direction to shine on a photodetector under the top electrode. Thus, the top layer 2226 structure can serve dual purposes of optical and capacitive sensing. A sensor device processor can be provided to process the pixel output signals from hybrid sensing pixels to extract the fingerprint information.

In addition to sharing the same structure for capacitive sensing and for focusing light in the vertical direction as a collimator, one instance of sensor signal detection circuitry can be shared between the optical and capacitive sensors to detect the sensor signals from both a photodetector and a capacitive sensor plate.

Figure 19A:
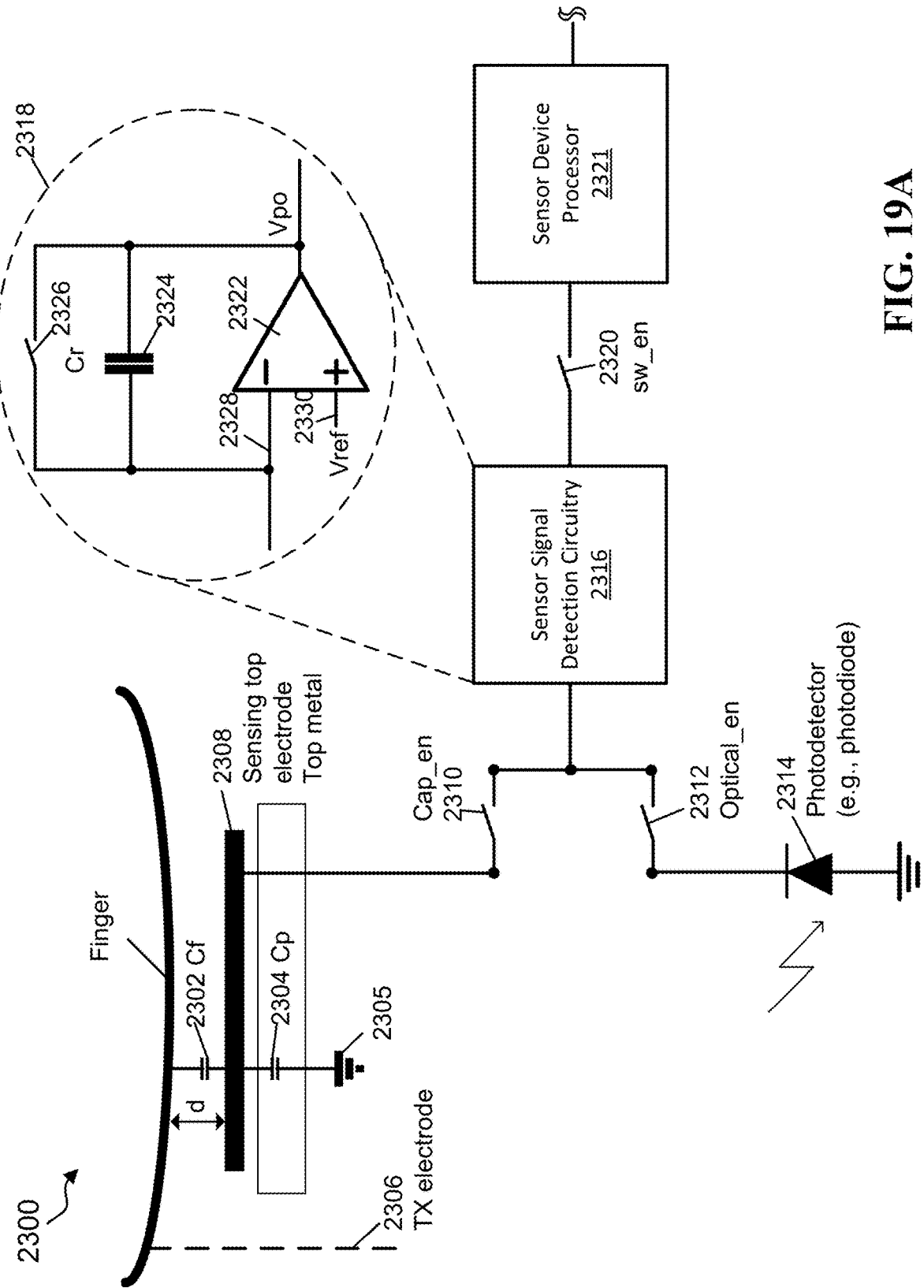
FIGS. 19A-19C illustrates a circuit diagram for another exemplary hybrid fingerprint sensing element or pixel.

FIG. 19A illustrates a circuit diagram for an exemplary hybrid fingerprint sensing element or pixel 2300 having both capacitive sensing and optical sensing functions for fingerprints. The exemplary sensor pixel 2300 includes sensor signal detection circuitry 2316 to selectively switch between detecting or acquiring sensor signals from a sensing top electrode (e.g., a top metal layer) 2308 based on capacitive sensing and a photodetector (e.g., a photodiode) 2314 based on optical sensing to acquire both a reflective optical image from the photodetector 2314 and a capacitive coupled image from the capacitive sensor electrode 2308 from a finger. In some implementations, the two images from the two sensing mechanisms in each hybrid sensing pixel can be serially processed by the sensor signal detection circuitry. In the illustrated example, switches 2310 and 2312 have first terminals that are electrically coupled to the sensing top electrode 2308 and the photodetector 2314, respectively, and second terminals that are coupled to a common input terminal of the sensor signal detection circuitry 2316 to provide corresponding optical detector signal from the photodetector 2314 and the corresponding capacitive sensing signal from the sensing top electrode 2308 to the sensor signal detection circuitry 2316. When the switch 2310 is turned off (CAP_EN=0) and the switch 2312 is turned on (Optical_en=1), the sensor signal detection circuitry 2316 acquires the optical detector signal representing the optical image of the scanned fingerprint received at the particular hybrid sensing pixel. The sensor signal detection circuitry 2316 can acquire the capacitive sensing signal representing the capacitive image of the scanned fingerprint when switch 2310 CAP_EN=1 and Optical_en=0. After both the optical and capacitive images are acquired, both images can be processed in downstream circuitry separately and in combination to identify the fingerprint characteristics.

With the two modality of imaging by the above hybrid sensing pixels, the performance of the fingerprint identification can be enhanced by making use of the two types of the images in different ways. This enhanced fingerprint identification can be achieved by the sensor device processor, such as sensor device processor 2321, for processing the pixel output signals from the hybrid sensing pixels to extract the fingerprint information. For example, the capacitive image can provide a 3D image on the depth of the ridges and valleys of the fingerprint features. Complementing the 3D capacitive image, the optical image can provide a high resolution 2D information on the fingerprint characteristics. The optical 2D image having a higher spatial resolution can be used to recover the capacitive sensing image resolution because both images information on the same ridges of the fingerprint. In some implementations where the capacitive sensing method may be more sensitive and accurate on identifying the valleys of the fingerprint than the optical sensing method, the spatial resolution of images acquired using the capacitive sensing method can degrade based on the thickness of the cover. This aspect of the capacitive sensing can be supplemented by the optical sensing. In operation, the sensor response may be fixed and the point spread function of the capacitive sensor may be fixed for all sensor positions. The higher resolution optical sensing can be used as a resolution recovery method and can be applied on the capacitive sensing image to enhance the 3D image. A partial high resolution image from optical sensing can be available to help with the recovering method. Thus, the 3D capacitive image can be enhanced to provide more information on the valleys and ridges by interpolating or recovering based on the high resolution 2D image.

The enhanced 3D image can provide an improved fingerprint recognition and matching. In another example, the optical and capacitive images can be stored together to provide two comparisons each time a fingerprint recognition or matching is performed. The use of two types of images for comparison enhances the accuracy and security of the fingerprint sensing system.

The sensor signal detection circuitry 2316 can be implemented in various ways using a number different circuitry designs. In one example, integrator sensing circuitry 2318 can be implemented to store the electric charges caused by ridges and valleys touching or being substantially near the cover of the fingerprint sensor device of the cover of the mobile device. The inclusion of the integrator circuitry 2318 enhances the signal-to-noise ratio (SNR). The integrator sensing circuitry includes an operational amplifier 2322 to amplify a sensor signal, such as a capacitance related or optical related signal (e.g., voltage signal), detected by the sensing top electrode 2308 or the photodetector 2314 of the exemplary sensor pixel 2300. The sensing top electrode 2308 that include a conductive material, such as one of a variety of metals is electrically connected to a negative or inverting terminal 2328 of the amplifier 2322 through the switch 2310. The sensing top electrode 2108 and a local surface of the finger 2302 function as opposing plates of a capacitor Cf 2302. The capacitance of the capacitor Cf 2302 varies based on a distance 'd' between the local surface of the finger and the sensing top electrode 2308, the distance between the two plates of the capacitor Cf 2302. The capacitance of capacitor Cf 2302 is inversely proportional to the distance 'd' between the two plates of the capacitor Cf 2302. The capacitance of capacitor Cf 2302 is larger when the sensing top electrode 2308 is opposite a ridge of the finger than when opposite a valley of the finger.

In addition, various parasitic or other capacitors can be formed between different conductive elements in the exemplary sensor pixel 2300. For example, a parasitic capacitor CP 2304 can form between the sensing top electrode 2308 and a device ground terminal 2305. Device ground is coupled to earth ground closely. Another capacitor Cr 2324 can form between an output conductor of the amplifier 2322 and the negative or inverting terminal 2328 of the amplifier 2322 and functions as a feedback capacitor to the amplifier 2322. Also, a switch 2326 can be coupled between the output of the amplifier 2322 and the negative or inverting terminal 2328 of the amplifier 2322 to reset the integrator circuitry 2318.

The positive terminal of the amplifier 2322 is electrically connected to an excitation signal Vref. The excitation signal Vref can be directly provided to the positive terminal of a dedicated amplifier in each sensor pixel. By providing the excitation signal Vref directly to the positive terminal of the amplifier 2322, the exemplary sensor pixel 2100 becomes an active sensor pixel. In addition, providing the excitation signal Vref directly to the positive terminal of the amplifier 2322 eliminates the need to include an excitation electrode, common to all sensor pixels, which reduces a conductive (e.g., metal) layer from the semiconductor structure of the sensor chip. In some implementations, an optional excitation electrode 2306 can be implemented to enhance the SNR based on the design of the sensor pixel. In addition, by providing the excitation signal Vref 2330 directly to the amplifier 2322, the excitation signal Vref 2322 is not applied directly to the finger to avoid potentially irritating or injuring the finger. Moreover, when the excitation electrode for applying the excitation signal directly to the finger is not used, all components of the fingerprint sensor device can be integrated into a single packaged device, and the entire fingerprint sensor device can be disposed under the protective cover glass. With the entire fingerprint sensor device disposed under the protective cover glass, the fingerprint sensor device is protected from the finger and other external elements that can potentially damage the fingerprint sensor.

In FIG. 19A, the output signal (optical and capacitive) of the sensor signal detection circuitry 2316 (e.g., Vpo of the amplifiers 2322) in the sensor pixels 2300 is electrically coupled to a switch 2320 to selectively output the output signal Vpo from the sensor pixel 2300 to a signal processing circuitry including a filter. The switch 2320 can be implemented using a transistor or other switching mechanisms and electrically coupled to a controller to control the switching of the switch 2320. By controlling the switches 2320, 2310 and 2312, the sensor pixels in an array of sensor pixels can be selectively switched between acquiring the optical signals and the capacitive signals. In one implementation, the optical or capacitive signal can be acquired for each line, row or column of sensor pixels in the array and then switched to acquire the other type of signal for the line, row or column. The switching between the optical and capacitive signal acquisition can be performed line-by-line. In another implementation, one type of signal (capacitive or optical) can be acquired for all sensor pixels or elements in the array and then switched to acquire the other type of signal for all of the sensor pixels or elements. Thus, the switching between acquisition of different signal types can occur for the entire array. Other variations of switching between acquisition of the two types of sensor signals can be implemented.

Figure 19B:
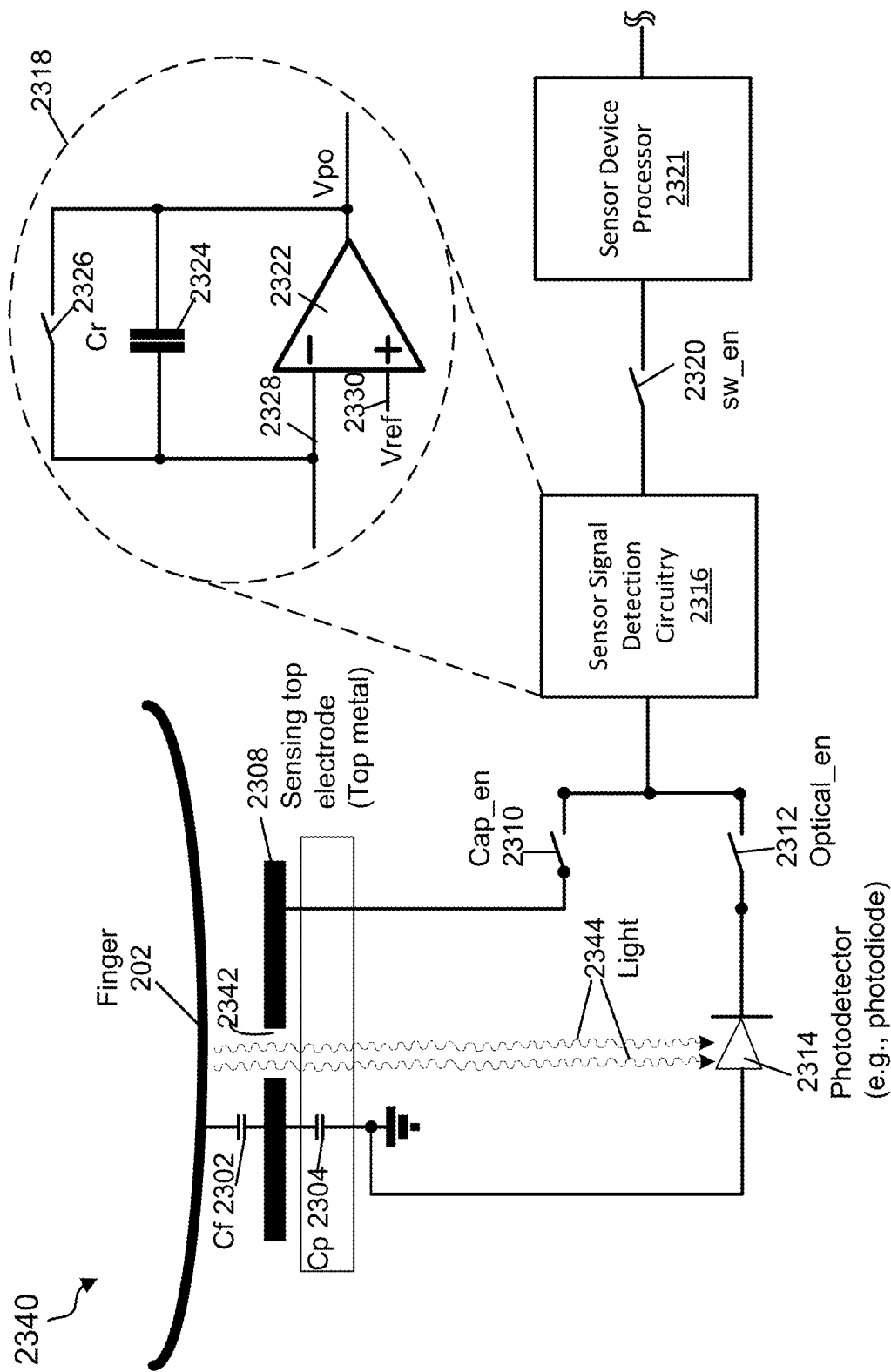

FIG. 19B illustrates a circuit diagram for another exemplary hybrid fingerprint sensing element or pixel 2340. The hybrid fingerprint sensing element or pixel 2340 is substantially the same as the hybrid fingerprint sensing element or pixel 2300 with respect to the components having the same reference number. For descriptions of the common components having the same reference number, refer to the description of FIG. 19A.

The hybrid fingerprint sensing element or pixel 2340 implements the sensing top electrode 2308 to include a hole or opening 2342 that functions as a collimator to focus or narrow the reflected light 2344 toward the photodetector 2314 (e.g., photodiode). The photodetector 2314 can be positioned or disposed below the collimator implemented using the sensing top electrode 2308 to capture the reflected light 2344 focused by the collimator 2308.

In some implementations, separate instances of sensor signal detection circuitry can be included for the optical and capacitive sensors to detect in parallel the sensor signals from both a photodetector and a capacitive sensor plate.

Figure 19C:
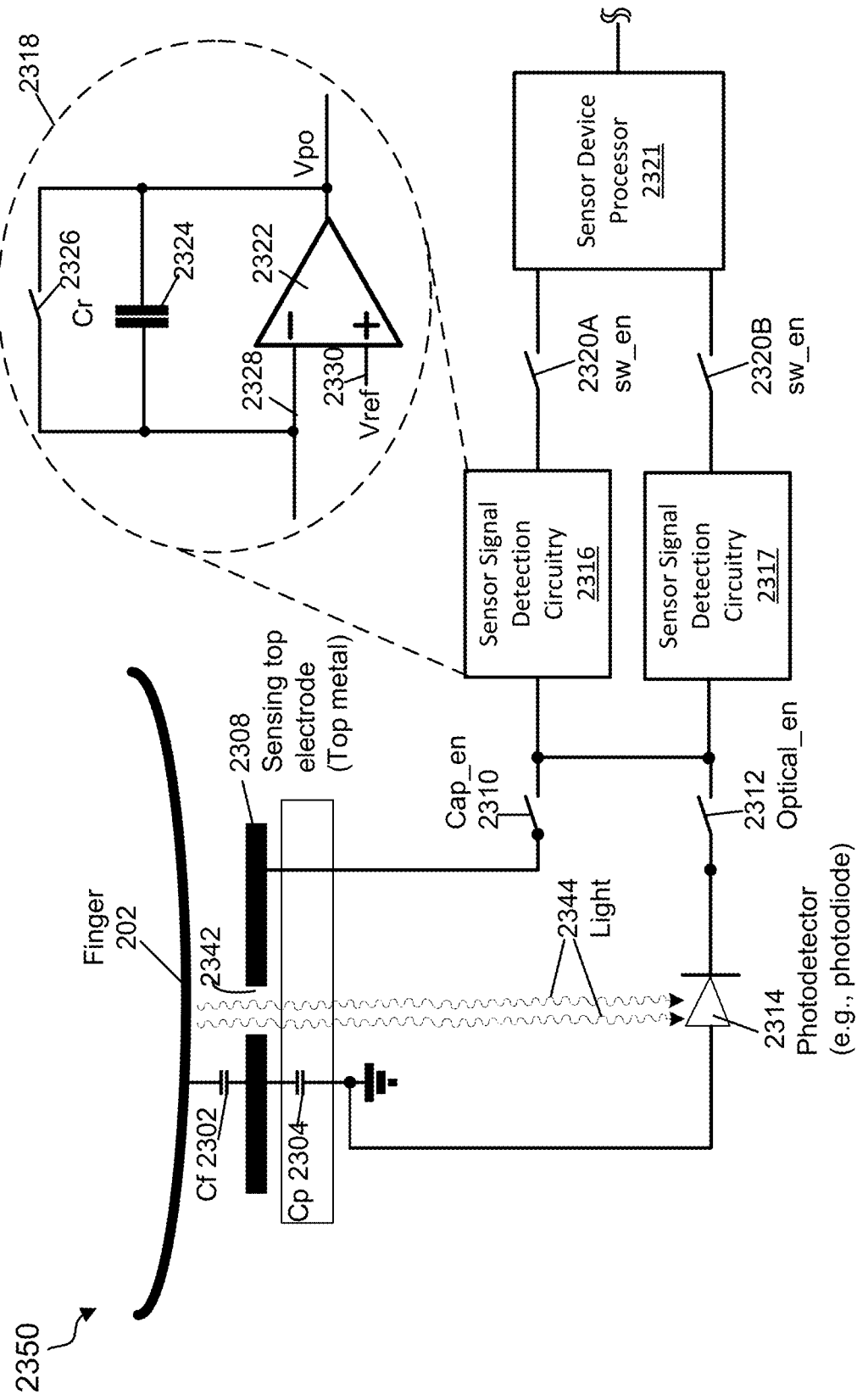

FIG. 19C illustrates a circuit diagram of an exemplary hybrid fingerprint sensing element or pixel 2350 for performing parallel detection of sensor signals from the photodetector and the capacitive sensor plate. The hybrid fingerprint sensing element or pixel 2350 is substantially the same as the hybrid fingerprint sensing element or pixel 2340 with respect to the components having the same reference number. For descriptions of the common components having the same reference number, refer to the description of FIG. 19A.

To perform sensor signal detection from both the capacitive plate and the photodetector in parallel, the hybrid fingerprint sensing element or pixel 2350 includes separate sensor signal detection circuitry 2316 and 2317 communicatively coupled to the sensing top electrode 2308 and the photodetector 2324 respectively. Sensor signal detection circuitry 2317 can be implemented to be substantially similar to sensor signal detection circuitry 2316. In some implementations, switches 2310 and 2312 can be disposed to have first terminals that are electrically coupled to the sensing top electrode 2308 and the photodetector 2314, respectively, and second terminals that are coupled to respective sensor signal detection circuitry 2316 and 2317 to provide the optical detector signal from the photodetector 2314 and the capacitive sensing signal from the sensing top electrode 2308 to the sensor signal detection circuitry 2316 and 2317 respectively. When the switches 2310 and 2312 are turned on and off together, the sensor signal detection circuitry 2316 and 2317 can perform sensor signal detection from the capacitive plate 2308 and the photodetector 2314 in parallel. When the switches 2310 and 2312 are turned on and off out of phase with each other, the sensor signal detection circuitry 2316 and 2317 can perform sensor signal detection from the capacitive plate 2308 and the photodetector 2314 in series. In addition, the sensor device processor 2321 can be communicatively coupled to the sensor signal detection circuitry 2316 and 2317 either directly or indirectly through switches 2320A and 2320B to process the detected sensor signals from the capacitive plate 2308 and the photodetector 2314 in parallel or in series.

In another aspect of the disclosed technology, the optical sensor described with respect to FIGS. 17A, 17B, 18, 19A and 19B can be used to measure human heart beat by measuring the reflected light intensity change with time caused by blood flow variations in fingers due to the heart beat and pumping actions of the heart. This information is contained in the received light that is reflected, scattered or diffused by the finger and is carried by the optical detector signal. Thus, the optical sensor can serve multiple functions including acquiring an optical image of the fingerprint and to measure human heart beat. In implementations, a sensor device processor is used to process one or more optical detector signals to extract the heart beat information. This sensor device processor may be the same sensor device processor that processes the pixel output signals from optical sensing pixels or hybrid sensing pixels to extract the fingerprint information.

FIGS. 20, 21A-21B, and 22A-22B illustrate examples of various designs for fingerprint sensing using an under-screen optical sensor module using an array of optical collimators or pinholes for directing signal light carrying fingerprint information to the optical sensor array. Such optical collimators or pinholes are placed between the display screen and the optical sensor array in the under-screen optical sensor module to couple desired returned light from the display panel while filtering out background light in the optical detection by the optical sensor array. Implementation of such optical collimators or pinholes can simplify the optical designs of the optical detection by the optical sensor array, e.g., without using complex optical imaging designs in other designs disclosed in this patent document, such as the imaging designs in FIGS. 6B, 7, 10A, and 11. In addition, implementation of such optical collimators or pinholes can simplify the optical alignment of the overall optical layout to the optical sensor array and improve reliability and performance of the optical detection by the optical sensor array. Furthermore, such optical collimators or pinholes can significantly simplify the fabrication and reduce the overall cost of the under-screen optical sensor module.

Figure 20:
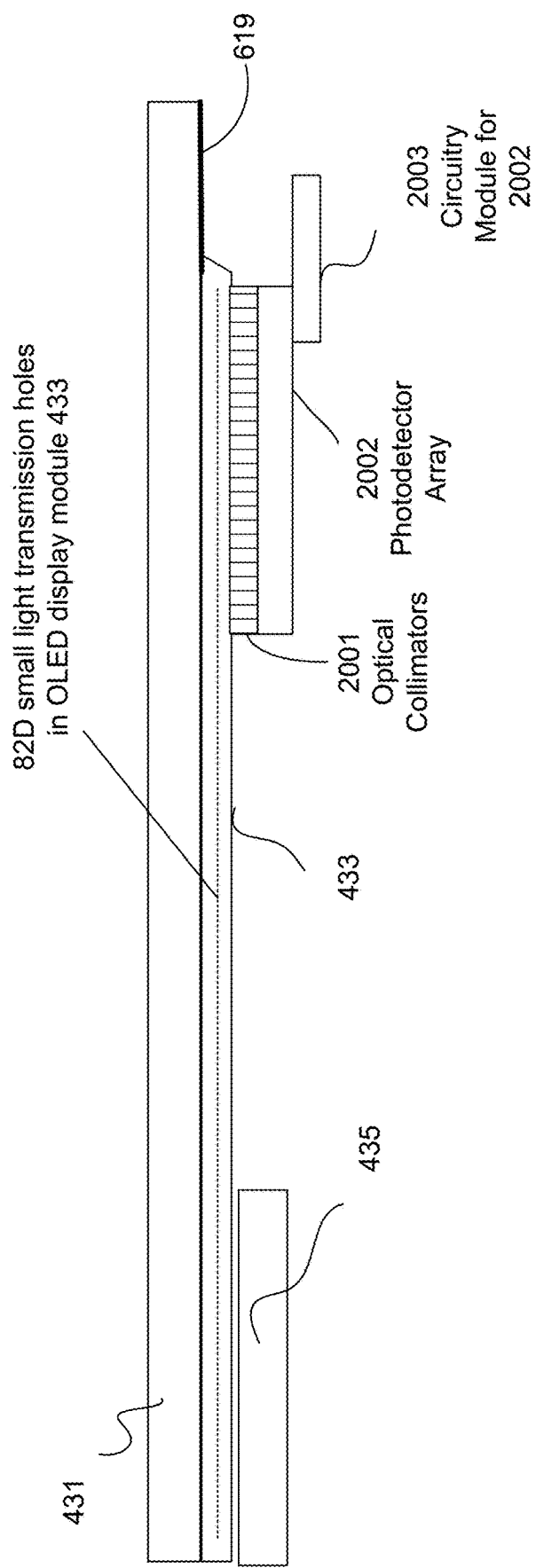
FIG. 20 shows an under-screen optical sensor module that includes an optical collimator array of optical collimators placed on top of a photodetector array for directing signal light carrying fingerprint information into different photodetectors on the photodetector array.

FIG. 20 shows an under-screen optical sensor module that includes an optical collimator array 2001 of optical collimators placed on top of a photodetector array 2002 for directing signal light carrying fingerprint information into different photodetectors on the photodetector array 2002. A circuitry module 2003 is coupled to the photodetector array 2002 to operate the photodetector array 2002 and to receive the output signals from photodetectors on the photodetector array 2002. The OLED display module 433 includes small light transmission holes 82D, e.g., holes in the TFT layer of the OLED display module, to allow the light from the top surface of the top transparent layer 431 to pass through the OLED display module 433 to reach the under-screen optical sensor module. The collimator array 2001 may use collimators in various designs, e.g., waveguide based image transmitters, an optical fiber array (with core or coreless), a micro lens array, a pinhole array and others. The collimators in the array 2001 are designed to limit the numerical aperture of the sampled image. Each pixel of the collimator array 2001 can be regarded as an optical detection needle. The photodiode array 2002 may be a CMOS sensor array, a CCD sensor array, a photodiode array or other photosensing array.

In operation, the OLED pixels illuminate the cover glass 431. The light reflected from the cover glass 431 is diffracted by the holes of the TFT structure in the OLED display module 433. The collimator array 2001 samples the useful part of the diffracted light and selects a portion of the light that fits the small numerical aperture of each collimator to transmit to the photodiode array 2002 to form the image of the sensing area.

FIGS. 21A-21B show the operation of the optical sensor module in FIG. 20. The OLED pixels in the illumination zone 613 in the OLED display module 433 shine light beam 82P to the finger in contact with the sensing zone 615 on the cover glass 431. The finger and the cover glass 431 reflect a light beam 82R. The small holes in the TFT substrate diffract the light beam 82R to form light beam 82D. Proper collimator units in the collimator array 2001 select light 82S from the light beam 82D and guide it into the proper photodetector elements of photodetector array 2002. In some OLED displays, part of the light may be directly shined towards the sensor module and may be eliminated by calibration.

FIGS. 22A-22B show an exemplary implementation of the design in FIG. 20 and FIGS. 21A-21B. The optical collimator array 2001 in this example includes an array of optical collimators 903 and an optical absorption material 905 filled between the optical collimators 903 to absorb light to reduce cross talk between different optical collimators. Each collimator 903 of the collimator array 2001 may be channels that are extended or elongated along a direction perpendicular to the display panel and lets the light be transmitted along its axis with a low loss. The collimator array 2001 is designed to reduce optical crosstalk between different optical collimators and to maintain a desired spatial resolution in the optical sensing. In some implementations, one optical collimator may correspond to only one photodetector in the photodetector array 2002. In other implementations, one optical collimator may correspond to two or more photodetectors in the photodetector array 2002. As illustrated in FIG. 22B, the axis of each collimator unit may be perpendicular to the display screen surface in some designs and may be slanted with respect to the display surface. In operation, only the light that propagates along a collimator axis carries the image information. For example, the proper incident light 82P is reflected to form light 82R. Light 82R is then diffracted by the small holes of the TFT and expanded to light 82D. The light portion 82S is transmitted into the photodiode array 2002. The light portion 82E away from the axis is absorbed by the filling material. The reflectance on the cover glass surface 431 carries the fingerprint information. Other OLED pixels emit light 901 which is at an angle with respect to the collimator unit axis and thus may be blocked. A part of the reflected light, such as 901E, transmits into a corresponding optical collimator to reach the photodetector array 2002.

The optical collimator array can be made by different techniques, including, e.g., etching holes through a flat substrate, forming a light waveguide array, forming a micro lens array matching with optical filters, using coreless optical fiber bundle, or printing collimators on a transparent sheet. The desired features for such a collimator array include: (1) sufficient transmission contrast between the light component that propagates along the axis and the component that propagates off the axis so that the collimators ensures the desired spatial resolution in the optical sensing of the fingerprint pattern at the photodetector array; (2) the permitted transmission numerical aperture be sufficiently small to realize a desired high spatial resolution for the optical sensing.

Various optical collimator array designs may be used. Each optical collimator in the optical collimator array is structured to perform spatial filtering by transmitting light in directions along or close to an axis of the optical collimator while blocking light in other directions and to have a small optical transmission numerical aperture to achieve a high spatial resolution by the array of optical collimators. The small optical transmission numerical aperture also reduces the amount of the background light that enters the optical sensor array. The collimator element aperture and the pitch (i.e., the distance between two nearby collimator elements) can be designed to achieve a desired spatial resolution for the optical fingerprint sensing.

Figure 23:
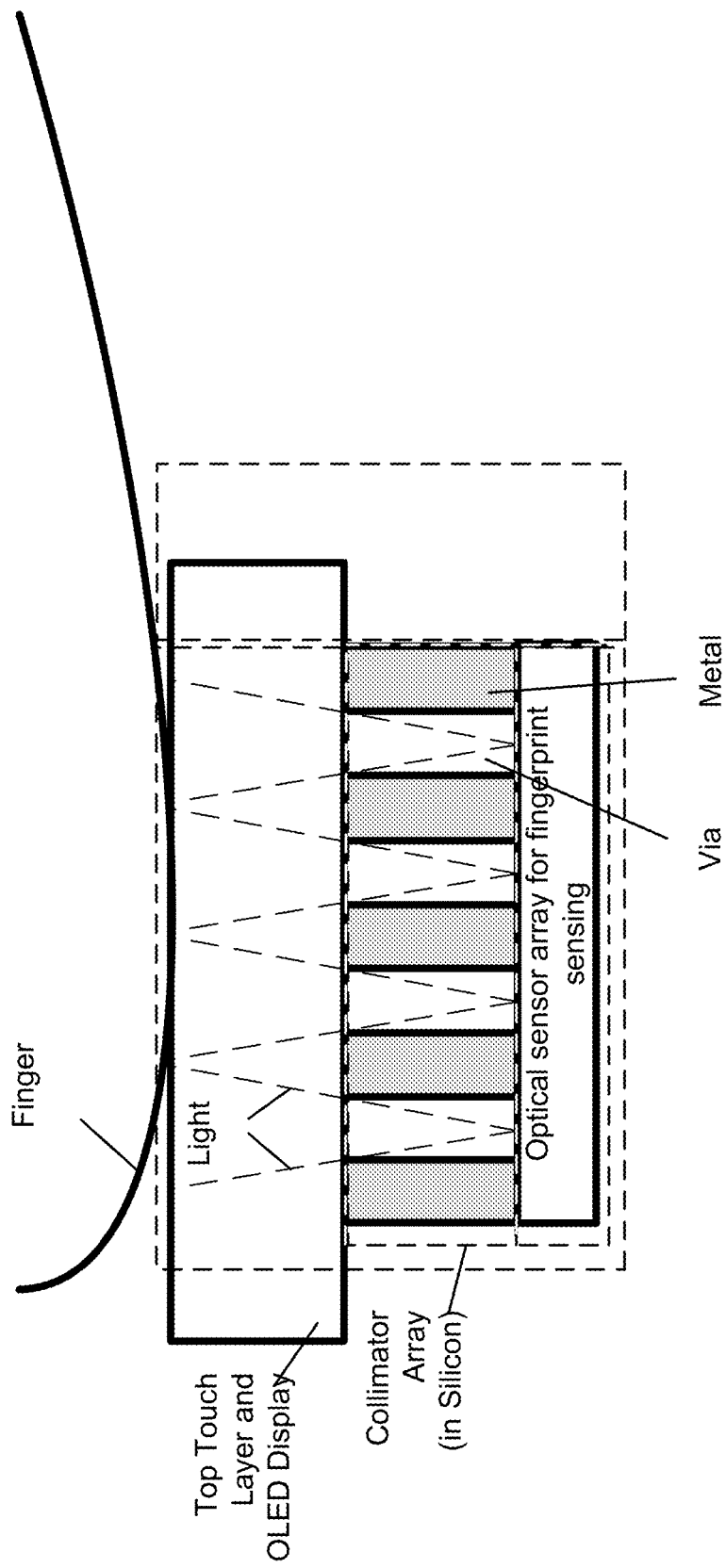
FIGS. 23 and 24 show examples of under-screen optical sensor modules with optical collimators.

FIG. 23 shows an example of a collimator design that is part of the CMOS structure by using aligned holes in two different metal layers in the CMOS structure. Each collimator in the array is an elongated channel along a direction that is perpendicular to the display panel.

Figure 24:
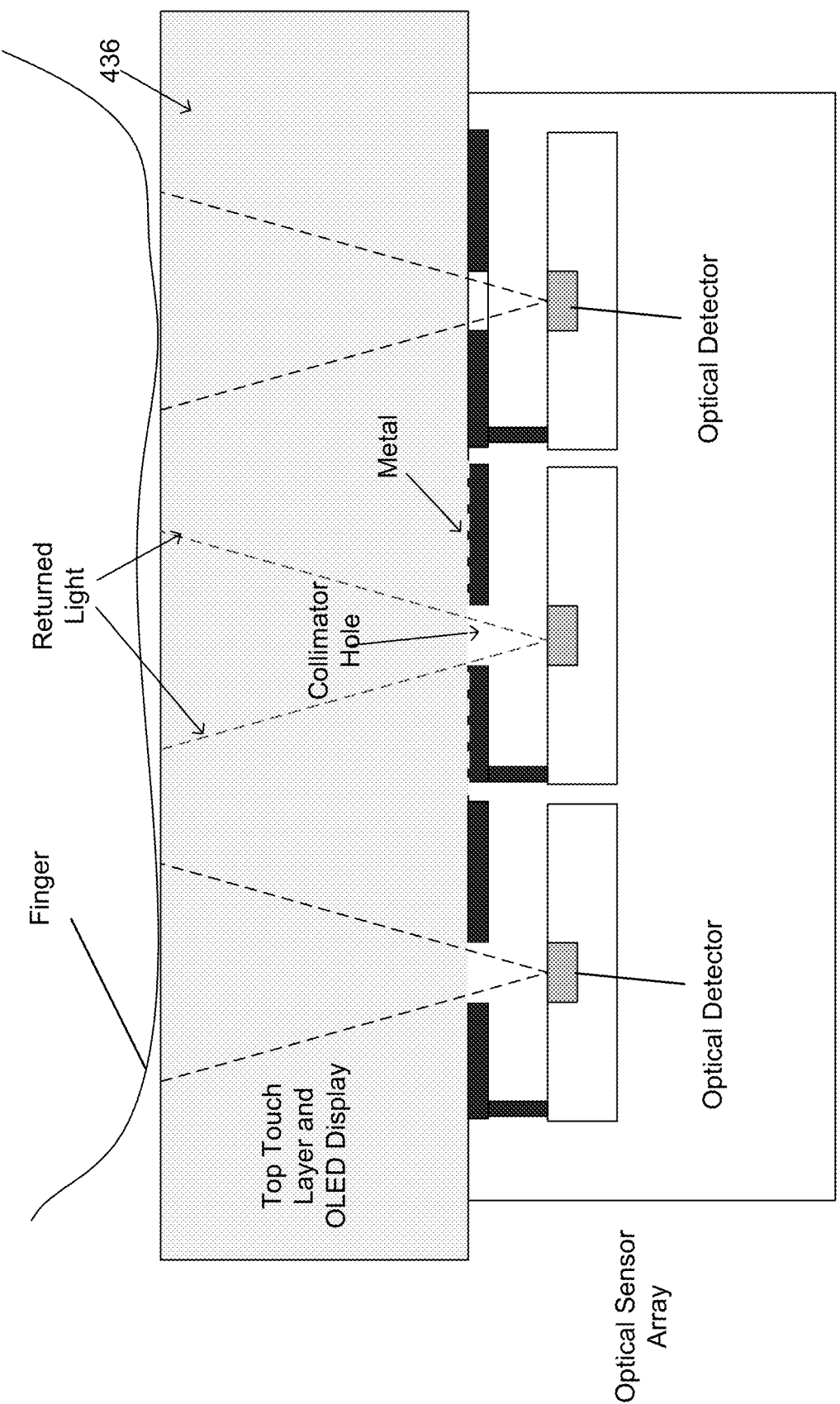

FIG. 24 shows an example of an optical fingerprint sensor module under the OLED display structure that incorporates an optical sensor array and an integrated collimator array for each optical sensor pixel in capturing fingerprint information. The optical sensor array includes an array of photodetectors and a collimator array is disposed over the photodetector array to include optically transparent vias as optical collimators and optically opaque metal structures between the vias as shown. The OLED display pixels emit light to illuminate the touched portion of a finger and the light reflected off the finger is directed through the collimator array to reach the photodetector array which captures a part of the fingerprint image of the finger. The collimator array can be implemented using one or more metal layer(s) with holes or openings integrated via the CMOS process.

Such optical collimators in the under-screen optical sensor module can be structured to provide direct point to point imaging. For example, the dimensions of the optical collimator array and individual collimators can be designed to closely match the dimensions of the photodetector array and the dimensions of individual photodetectors, respectively, to achieve one to one imaging between optical collimators and photodetectors. The entire image carried by the light received by the optical sensor module can be captured by the photodetector array at individual photodetectors simultaneously without stitching.

The spatial filtering operation of the optical collimator array can advantageously reduce the amount of the background light that enters the photodetector array in the optical sensor module. In addition, one or more optical filters may be provided in the optical sensor module to filter out the background light and to reduce the amount of the background light at the photodetector array for improved optical sensing of the returned light from the fingerprint sensing area due to the illumination by emitted light from the OLED pixels. For example, the one or more optical filters can be configured, for example, as bandpass filters to allow transmission of the light at emitted by the OLED pixels while blocking other light components such as the IR light in the sunlight. This optical filtering can be an effective in reducing the background light caused by sunlight when using the device outdoors. The one or more optical filters can be implemented as, for example, optical filter coatings formed on one or more interfaces along the optical path to the photodetector array in the optical sensor module or one or more discrete optical filters.

Figure 25:
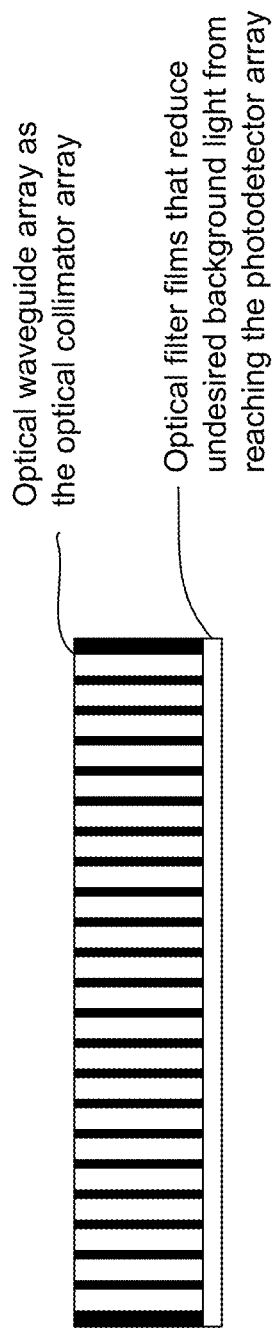
FIG. 25 shows an example an optical collimator array with optical filtering to reduce background light that reaches the photodetector array in the under-screen optical sensor module.

FIG. 25 shows an example an optical collimator array with optical filtering to reduce background light that reaches the photodetector array in the under-screen optical sensor module. This example uses an array of optical waveguides as the optical collimators and one or more optical filter films are coupled to the optical waveguide array to reduce undesired background light from reaching the photodetector array coupled to the optical waveguide array, e.g. the IR light from the sunlight while transmitting desired light in a predetermined spectral band for the probe light that is used to illuminate the finger. The optical waveguide can include a waveguide core with or without an outside waveguide cladding. The optical waveguide may also be formed by a coreless fiber bundle with different fibers where each unit collimator is a piece of fiber without a fiber core structure. When the coreless fibers are made into bundle, the filling material between the fibers may include a light absorbing material so as to increase the absorption of stray light that is not guided by the coreless fibers. The final collimator may be assembled with multiple layers of sub-collimator arrays.

The following sections provide examples of various optical collimator designs and their fabrication.

FIGS. 26A and 26B show examples of fabricating collimators by etching. In FIG. 26A, a layer of a suitable material for forming optical collimators in the collimator array is formed on or supported by a support substrate which is optically transparent. An etching mask is formed over the layer and has a pattern for etching the underlying layer to form the optical collimators. A suitable etching process is performed to form the optical collimators. The support substrate may be bound with the collimator array and may be formed from various optical transparent materials including, e.g., silicon oxide.

FIG. 26B shows an example of an optical collimator array that is assembled by stacking multiple layers of sub-collimator arrays via an inter-layer connector material which may be an adhesive, a glass, or a suitable optically transparent material. In some implementations, different layers of sub-collimator arrays may be stacked over one another without the inter-layer connector material. This stacking allows fabrication of optical collimators with desired lengths or depths along the collimator axis to achieve desired numerical apertures. The holes of the collimators geometrically limit the viewing angle. The transmitting numeral aperture is decided by the thickness of the collimator and the hole aperture. The holes may be filled with an optically transparent material in some applications and may be void in some designs.

In implementations, the support substrate may be coated with one or more optical filter films to reduce or eliminate background light such as the IR light from the sunlight while transmitting desired light in a predetermined spectral band for the probe light that is used to illuminate the finger.

FIG. 27 shows an array of optical spatial filters coupled with micro lens array where each microlens is located with respect to a corresponding through hole of an optical spatial filter so that each unit collimator includes a micro lens and a micro spatial filter, such as a micro hole. Each micro lens is structured and positioned to focus received light to the corresponding micro spatial filter without imaging the received light. The micro hole limits the effective receiving numerical aperture. The spatial filter may be printed on an optically transparent substrate, or etched on a piece of silicon wafer. The micro lens array may be etched by MEMS processing or chemical processing. The micro lens may also be made of a gradient refractive index material, e.g., cutting a piece of gradient refractive index glass fiber to a quarter pitch of length. The focal length of the micro lenses and the diameter of the spatial filter hole can be used to control the transmitting numerical aperture of each unit. Like in other designs, the collimator board may be coated with filter films to reduce or eliminate the light band not used in the sensor such as the IR light from the sunlight.

Figure 28:
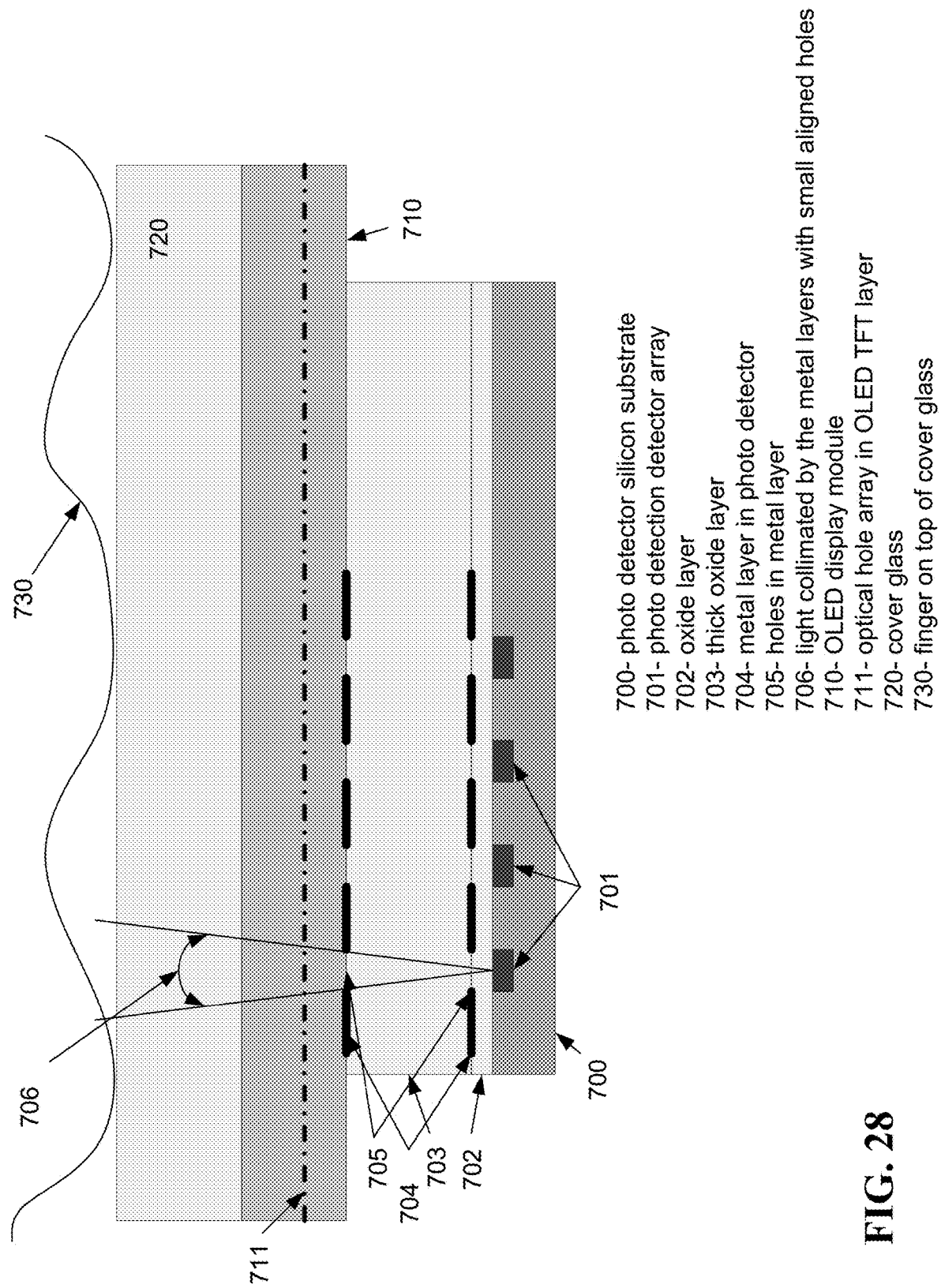
FIG. 28 shows an example of an integrated CMOS photo detection array sensor, with built-in collimation of light.

FIG. 28 shows an example of an integrated CMOS photo detection array sensor, with built-in collimation of light. The collimator is built by combing an array of aligned holes (705) in different metal layers (704) and oxide layers (702, 703) which are interleaved between metal layers to provide separation. These holes can be aligned with photo sensitive elements (701) in the optical sensor array. Optical fingerprint imager is implemented with this integrated CMOS photo detection array sensor with built-in collimation of light under the OLED display module (710) and cover glass. The fingerprint of the user's finger in touch with the sensor window area of the cover glass can be imaged by detection of the light reflected off the fingerprint valley and ridges, with the light emitting from the OLED display pixels of the window area. The light from a fingerprint ridge area would be reduced, because the light is absorbed in fingerprint tissue at the ridge area while the light from the fingerprint valley area stronger by comparison. This difference in the light levels between the ridges and valleys of a fingerprint produces a fingerprint pattern at the optical sensor array.

In the above optical sensor module designs based on collimators, the thickness or length of each collimator along the collimator can be designed to be large to deliver imaging light to a small area on the optical detector array or to be small to deliver imaging light to a large area on the optical detector array. When the thickness or length of each collimator along the collimator in a collimator array decreases to a certain point, e.g., tens of microns, the field of the optical view of each collimator may be relatively large to cover a patch of adjacent optical detectors on the optical detector array, e.g., an area of 1 mm by 1 mm. In some device designs, optical fingerprint sensing can be achieved by using an array of pinholes with each pinhole having a sufficiently large field of optical view to cover a patch of adjacent optical detectors in the optical detector array to achieve a high image resolution at the optical detector array in sensing a fingerprint. In comparison with a collimator design, a pinhole array can have a thinner dimension and a smaller number of pinholes to achieve a desired high imaging resolution without an imaging lens. Also, different from the imaging via optical collimators, imaging with the array of pinholes uses each pinhole as a pinhole camera to capture the image and the image reconstruction process based on the pinhole camera operation is different that by using the optical collimator array: each pinhole establishes a sub-image zone and the sub image zones by different pinholes in the array of pinholes are stitched together to construct the whole image. The image resolution by the optical sensor module with a pinhole array is related to the sensitive element size of the detector array and thus the sensing resolution can be adjusted or optimized by adjusting the detector dimensions.

A pinhole array can be relatively simple to fabricate based on various semiconductor patterning techniques or processes or other fabrication methods at relatively low costs. A pinhole array can also provide spatial filtering operation to advantageously reduce the amount of the background light that enters the photodetector array in the optical sensor module. Similar to designing the optical sensor modules with optical collimators, one or more optical filters may be provided in the optical sensor module with a pinhole array to filter out the background light and to reduce the amount of the background light at the photodetector array for improved optical sensing of the returned light from the fingerprint sensing area due to the illumination by emitted light from the OLED pixels. For example, the one or more optical filters can be configured, for example, as bandpass filters to allow transmission of the light at emitted by the OLED pixels while blocking other light components such as the IR light in the sunlight. This optical filtering can be an effective in reducing the background light caused by sunlight when using the device outdoors. The one or more optical filters can be implemented as, for example, optical filter coatings formed on one or more interfaces along the optical path to the photodetector array in the optical sensor module or one or more discrete optical filters.

Figure 29:
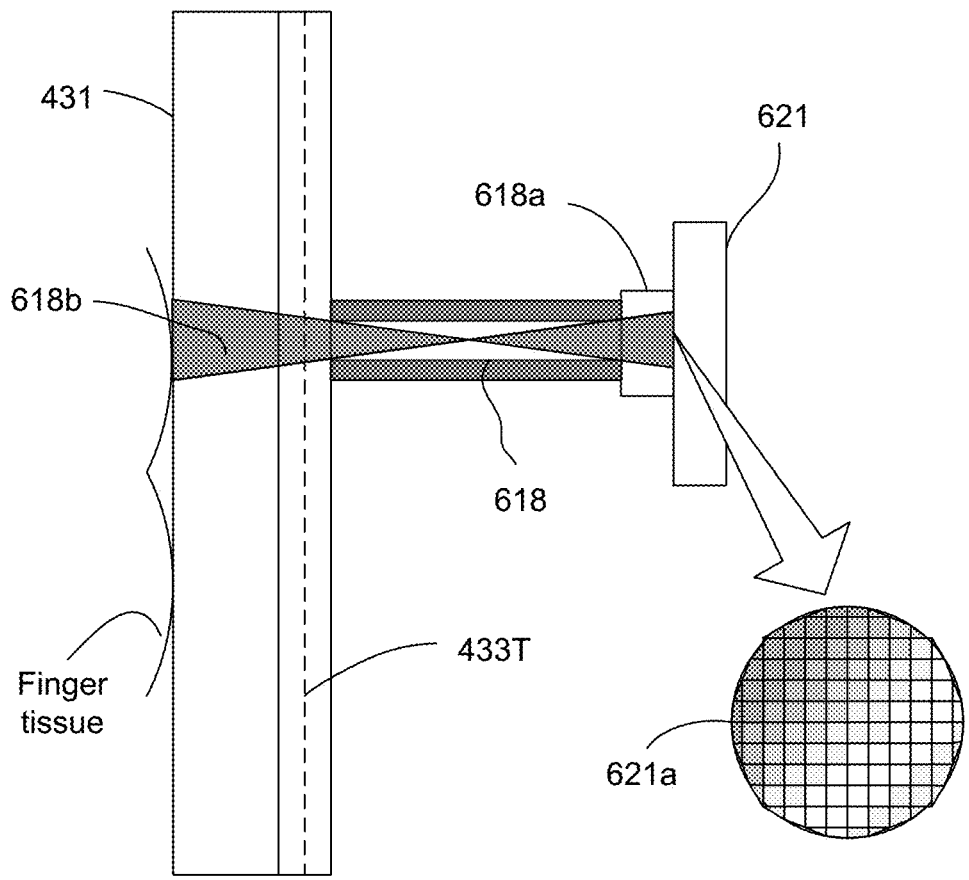
FIG. 29 shows an example of an optical sensor module based on optical collimators, the optical imaging resolution at the optical sensor array can be improved by configuring the optical collimators in a way to provide a pinhole camera effect.

In an optical sensor module based on optical collimators, the optical imaging resolution at the optical sensor array can be improved by configuring the optical collimators in a way to provide a pinhole camera effect. FIG. 29 shows an example of such a design.

In FIG. 29, a collimator unit 618 of an array of such optical collimators guides the light from the corresponding detection area unit to the photo detector array 621. The aperture of the collimator unit forms a small field of view (FOV) 618b. If the detector in the photo detector array 621 does not capture the details in each unit FOV, the imaging resolution is decided by the FOV of each collimator unit. To improve the detection resolution, the FOV of each collimator unit needs to be reduced. However, when a gap 618a is provided between each photo detector in the photo detector array 621 and the corresponding collimator 618, the small aperture of the collimator unit acts as a pinhole. This pinhole camera effect provides a higher imaging resolution in the image of each unit of FOV. When there are multiple detector elements in a unit FOV, such as shown in the insert 621a, the images details in the unit FOV can be recognized. This means that the detection resolution is improved. In implementations, such a gap can be provided in various ways, including, e.g., adding optical filter films 618a between the collimators 618 and the optical sensor array 621.

With the help of the pinhole camera effect, the fill factor of the collimator board, may be optimized. For example, to detect an area of 10 mm×10 mm in size, if each unit FOV covers an area of 1 mm×1 mm, a 10×10 collimator array can be used. If in each unit FOV the detector can get 20×20 definition image, the overall detection resolution is 200× 200, or 50 micron, or 500 psi. This method can be applied for all types of collimator approaches.

Figure 30:
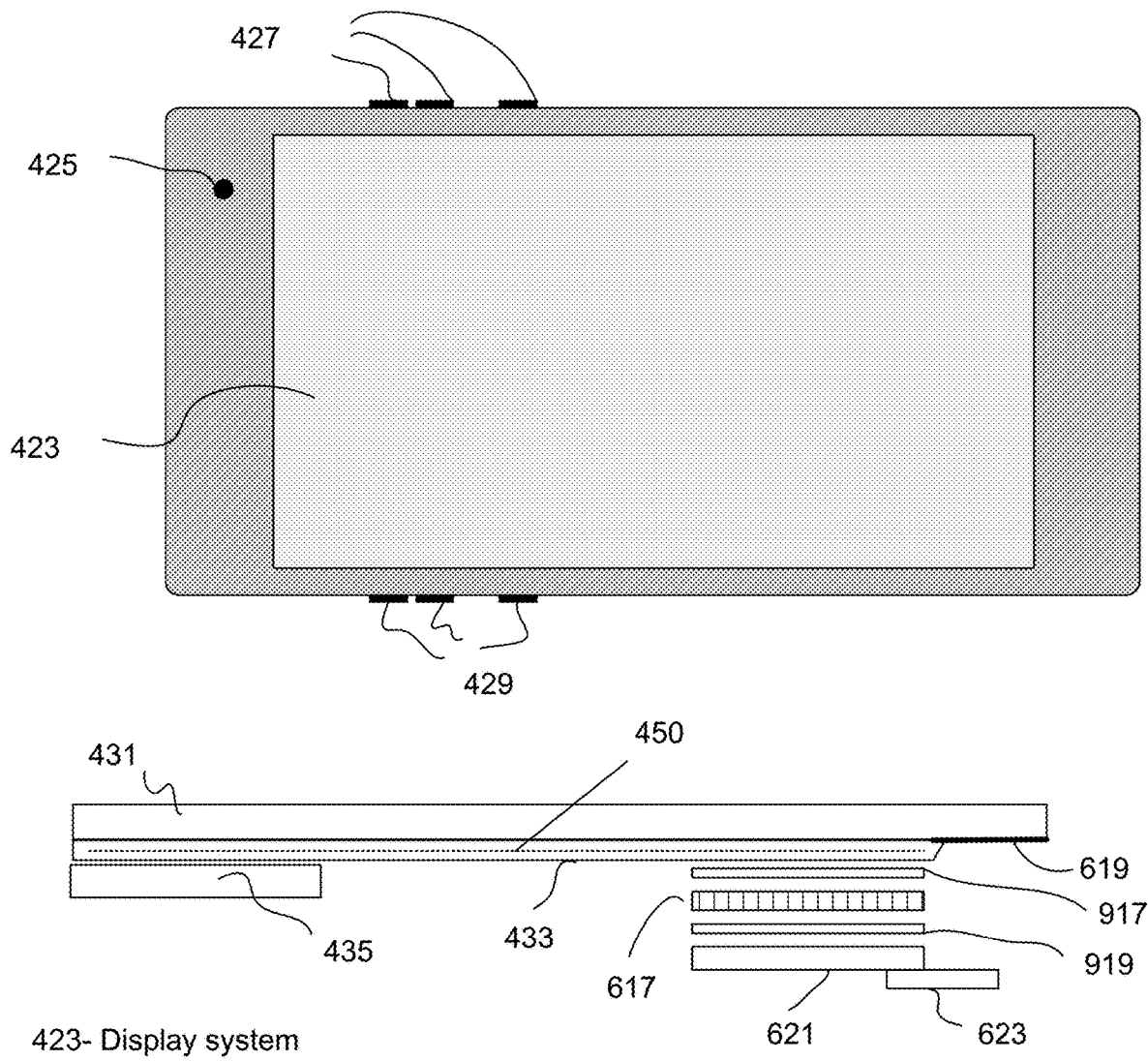
FIG. 30 shows another example for using the pinhole camera effect to improve the optical imaging resolution.

FIG. 30 shows another example for using the pinhole camera effect to improve the optical imaging resolution. The OLED display module layer 433 under the top transparent layer 431 includes, among others, OLED layers including an array of OLED pixels that emit light for displaying images and have electrodes and wiring structure optically acting as an array of holes and light scattering objects. The array of holes in the OLED layers is shown as small light transmitting holes 450 inside the OLED display module layer 433 and allows transmission of light from the top transparent layer 431 through the OLED layers to reach the optical sensor module 621 for fingerprint sensing. In this example, the optical sensor module includes several layers: a spacer 917 below the OLED display module layer 433 and above the pinhole array 617, a protection material 919 below the pinhole array 617 and above the photo detector array 621, and a circuit board 623. The object optical distance is decided by the total material thickness from sensing surface to the pinhole plane, including the optical thickness of the display module 433 thickness, the spacer 917 thickness, any filter coating thickness, any air gap thickness, and any glue material thickness. The image optical distance is decided by the total material thickness from the pinhole plane to the photo detector array, including the protection material thickness, any filter coating thickness, any air gaps thickness, any glue material thickness. The image magnification is decided by the image optical distance comparing with the object optical distance. The detection mode can be optimized by setting a proper magnification. For example, the magnification may be set to be less than 1, such as, 0.7, or 0.5 etc. In some device designs, the spacer and the pinhole array layer may be combined into a single component. In other designs, the pinhole array and the protection layer may be combined to a single component so as to pre-define the center co-ordinates of each pinhole.

Figure 31A:
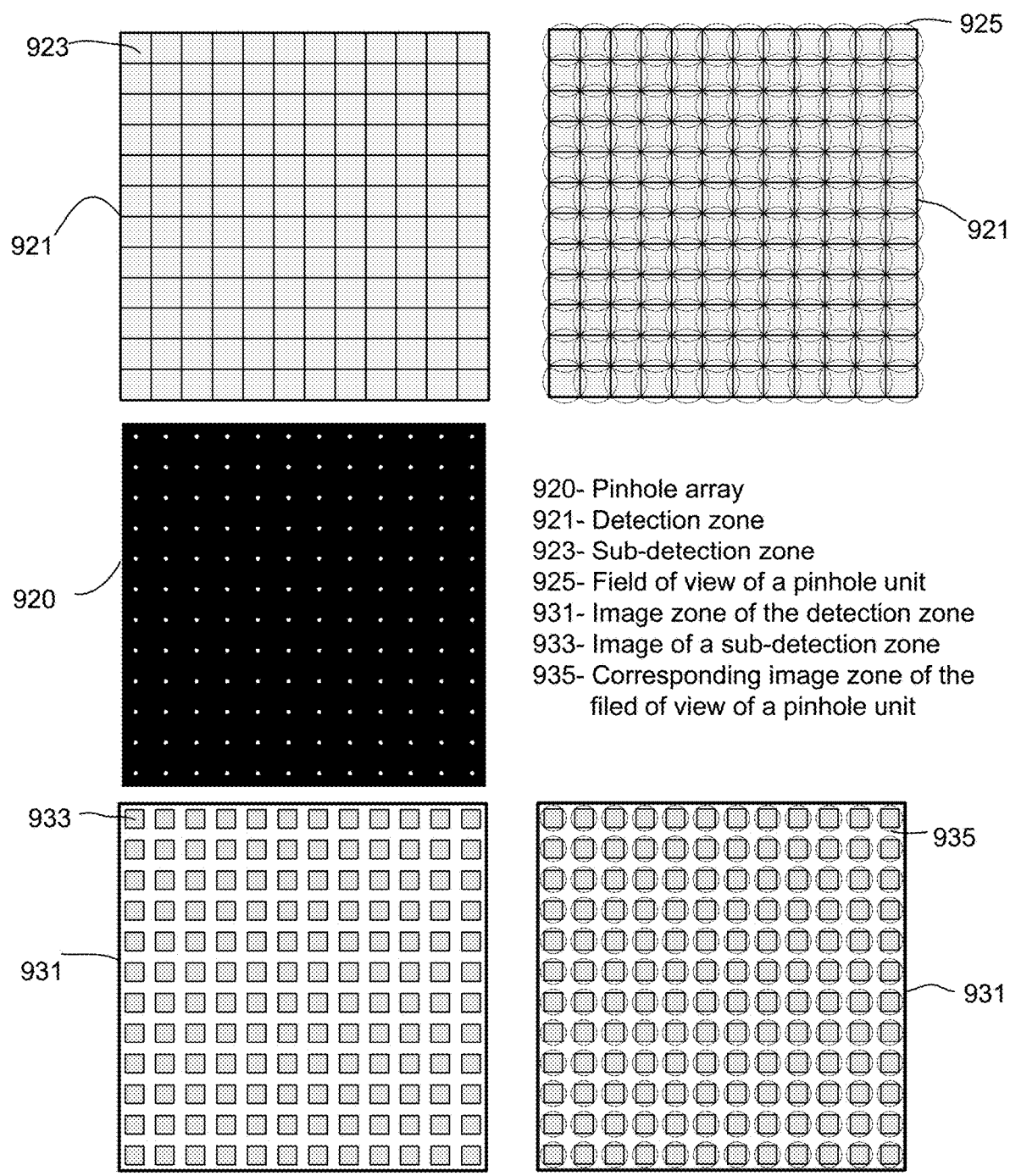
FIG. 31A shows an example of the optical imaging based on the pinhole camera effect.

FIG. 31A shows an example of the optical imaging based on the pinhole camera effect. On the object side, the whole detection zone 921 on the OLED display panel is divided into multiple sub-detection zones 923. A pinhole array 920 is provided for imaging the detection zone 921. Each pinhole unit in the pinhole array 920 is responsible for a small field of view (FOV) 925. Each small FOV 925 covers a sub-detection zone 923. As shown in FIG. 31A, each small FOV of one pinhole can overlap with small FOVs of its neighboring pinholes. On the image side, each sub-detection zone 923 in the optical sensor array captures an image 933. Also shown in FIG. 31A, each small FOV 925 of a pinhole has a corresponding image zone 935. The magnification of this system can be optimized so that the images of each sub-detection zone can be separately distinguished. In other words, the images of the small FOVs do not overlap each other. In this detection mode, the central co-ordinates of each pinhole are pre-defined and the image spot co-ordinates of each OLED display pixel can be pre-calibrated. All the display pixels in the detection zone can be lit on simultaneously because each pixel has only one corresponding image position. Because the image of the pinhole camera is inversed, the signal processing can recover the whole image based on the calibration table.

Figure 31B:
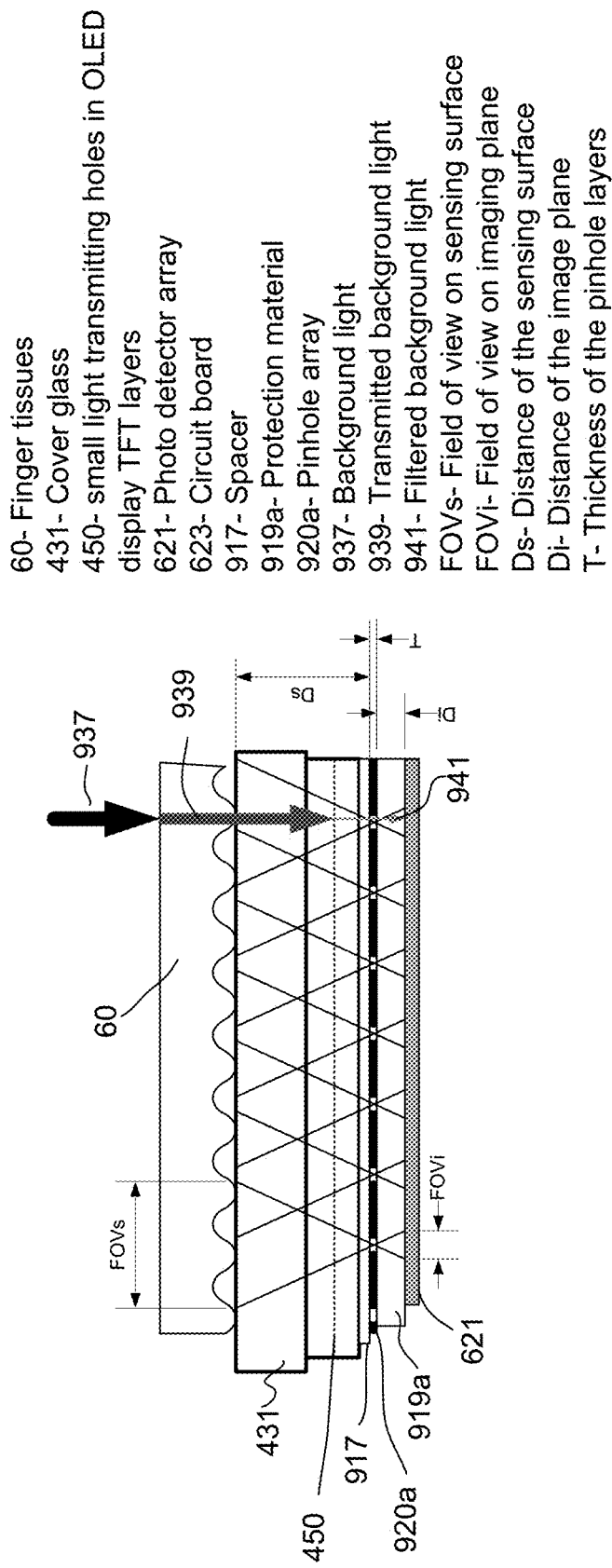
FIG. 31B shows an example of an under-screen optical sensor module by implementing an array of optical pinholes to illustrate device design factors that impact the field of the view (FOVi) produced by each pinhole at the optical detector array and thus the imaging resolution of the optical sensor module.

FIG. 32B shows an example of an under-screen optical sensor module by implementing an array of optical pinholes to illustrate device design factors that impact the field of the view (FOVi) produced by each pinhole at the optical detector array and thus the imaging resolution of the optical sensor module. The illustrated example shows the thickness values of relevant layers such as the total thickness (Ds) of the top transparent layer 431 and the OLED display module layer 433, the thickness (T) of the layers 920a for the pinhole array 920a, the thickness (Di) of the protection material 919 below the pinhole array 617 and above the photo detector array 621. As shown in FIG. 31B, the pinhole array 920a is applied to image the sensing area where finger 60 pressed upon the top sensing surface over the top transparent layer 433 and the thickness T of the pinhole layers 920a can affect the field of view (FOV) angles. Together with the distances from the sensing surface to the pinhole and from the image plane to the pinhole, the sensing area FOVs and imaging area FOVi are defined. The image magnification is given by Di/Ds. In designing the device, the values of T, Ds, and Di can be adjusted and optimized to achieve a desired FOV and image magnification.

In the example in FIG. 31B, the neighboring FOVs can be adjusted to overlap properly. Similarly, the neighboring FOVi can also be adjusted to be partially overlapped or fully separate or discrete from each other. In a design that neighboring FOVs overlap each other, some of the spots on the sensing surface can have multiple image spots. This feature can be used to enhance the optical detection of a fingerprint.

Either of the two background reduction techniques in FIGS. 12 and 13 may be applied to the operation of the optical sensor module in FIG. 31B to reduce the background noise. For example, the display scan frame can be used to generate different frames of fingerprint signals. When two sequentially obtained frames of signals are obtained with the display being lit on in one frame and being turned off in the other frame, the subtraction of the two frames of signals can be used to reduce or eliminate the ambient background light influence as shown in FIG. 12 in which the fingerprint sensing frame rate is one half of the display frame rate under this mode of operation.

In implementing the design in FIG. 31B and other designs for a under-screen optical sensor module, optical filter films for reducing the background light may be coated on the spacer 917, on the pinhole layers 920a, on the protection layer 919a, or on the display surfaces. As illustrated in FIG. 31B, when background light 937 is projected onto the finger tissues 60, short wavelength components tend to be mostly absorbed by the finger tissues, a portion of the light in the longer wavelength (such as red light or infrared light) light transmits through the finger and propagates towards the optical detector array 621. The optical filter films can be used to reject those background light components at longer wavelengths to improve the optical detection of the fingerprint.

In the above illustrated examples for optical collimators, the direction of the optical collimators for directing light from a finger on the top of the display screen into the optical sensor array for fingerprint sensing may be either perpendicular to the top touch surface of OLED display screen to collect returned probe light from the finger for fingerprint sensing, a majority of which is in a light direction perpendicular to the top touch surface. In practice, when a touched finger is dry, the image contrast in the detected images in the optical sensor array by sensing such returned probe light that is largely perpendicular to the top touch surface is lower than the same image obtained from returned probe light that is at an angle with respect to the perpendicular direction of the top touch surface. This is in part because optical sensing of angled returned light spatially filters out the strong returned light from the top touch surface that is mostly perpendicular to the top touch surface. In consideration of this aspect of the optical sensing of the returned probe light from the top touch surface, the optical collimators may be oriented so that the axis of each collimator unit may be slanted with respect to the top touch surface as shown in the example in FIG. 22B.

In fabrication, however, it is more complex and costly to fabricate slanted collimators. One way to use perpendicular optical collimators as shown in FIGS. 20 and 21B while still achieving a higher contrast in the optical sensing by selectively detecting angled returned light from the top touch surface is to provide an optical deflection or diffraction device or layer between the perpendicular optical collimators and the returned light from the top touch surface prior to entering the perpendicular optical collimators. This optical deflection or diffraction device or layer can be, in some implementations, between the OLED display panel and the perpendicular optical collimators to select only returned probe light that is at some slanted angle to enter the perpendicular optical collimators for optical detection by the optical detector array on the other end of the perpendicular optical collimators while blocking or reducing the amount of the returned probe light from the top touch surface that is perpendicular to the top touch surface from entering the optical collimators. This optical deflection or diffraction device or layer may be implemented in various forms, including, e.g., an array of prisms, an optical layer with a diffraction pattern, or other devices located between the optical collimators and the display panel to select angled probe light returned from the display panel to enter the optical collimators while reducing an amount of the returned probe light that is perpendicular to the display panel and enters the optical collimators.

FIG. 32 includes FIGS. 32A and 32B and shows an example of an optical fingerprint sensor under an OLED display panel having an optical deflection or diffraction device or layer.

As shown in FIG. 32A, each collimator 2001 in the collimator array may be an extended channel along an axis vertical or perpendicular to the display surfaces. A viewing angle adaptor optical layer 2210 is used to adjust the viewing angle of the returned probe light from the display panel and is located between the optical collimators 2001 and the display panel to select angled probe light returned from the display panel to enter the optical collimators 2001 while reducing an amount of the returned probe light that is perpendicular to the display panel and enters the optical collimators 2001.

FIG. 32B shows more detail of the viewing angle adaptor optical layer 3210 and the major probe light paths. For example, the viewing angle adaptor optical layer 3210 may be implemented as a diffraction pattern layer such as a prism structure 3210a. Only the returned probe light 82a and 82b from the finger with proper incident angles out of the display panel can be bent to transmit through the collimator 2001. In comparison, the returned probe light that is perpendicular to the display panel is directed by the viewing angle adaptor optical layer 2210 to be away from the original direction that is perpendicular to the display panel and thus becomes off-axis incident light to the optical collimator 2001. This reduces the amount of the returned probe light that is perpendicular to the display panel and that can enter the optical collimator 2001.

When the viewing angle is adjusted properly, the receiving light from different places 63a and 63b of the fingerprint valley carried the fingerprint information. For example, under same illumination, light 82a may be stronger than light 82b because of the viewing angel and the fingerprint profiles of the fingertip skin. In other words, the detection can see some level of fingerprint shade. This arrangement improves the detection when the finger is dry.

Portable devices such as mobile phones or other devices or systems based on the optical sensing disclosed in this document can be configured to provide additional operation features.

For example, the OLED display panel can be controlled to provide a local flash mode to illuminate the fingerprint sensing area 613 by operating selected OLED display pixels underneath the sensing area 613. This can be provided in an optical sensor module under the OLED display panel, e.g., FIGS. 4A and 4B based on an optical imaging design or FIGS. 21A and 21B based on optical imaging via an optical collimator array. In the event of acquiring a fingerprint image, the OLED display pixels in the window area 613 can be turned on momentarily to produce high intensity illumination for optical sensing of a fingerprint, and, at the same time, the photo detection sensor array 621 is turned on to capture the fingerprint image in sync with the turning on of the OLED pixels underneath the sensing area 613. The time to turn on these OLED pixels can be relatively short but the emission intensity can be set to be higher than the normal emission for displaying images on the OLED display panel. For this reason, this mode for optical fingerprint sensing is a flash mode that enable the photo detector sensor array 621 to detect a larger amount of light to improve the image sensing performance.

For another example, the optical sensor module can be designed to meet the total internal reflection condition at the top sensing surface of the OLED display panel to achieve a flash wakeup function where a part of the OLED pixels in the viewing zone 613 are turned on to flash while other OLED pixels are tuned off and are in a sleep mode to save power when the device is not in use. In response to the flashing of the OLED pixels in the viewing zone 613, the corresponding photo sensors in the optical sensor array 621 are operated to receive and detect light signals. When a finger touches the sensing zone 613 during this flash wakeup mode, the finger causes returned light to be totally reflected to produce strong returned probe light which is detected at the optical sensor array and the detection of the presence of light can be used to wake up the device in the sleep mode. In addition to using the part of OLED pixels in the viewing zone 613, one or more extra light sources may be provided near the optical sensor module to provide the flash mode illumination at the viewing zone 613 for the flash wakeup function. When a non-finger object touches the viewing zone 613 on the top surface above the OLED display panel, the total internal reflection condition may not occur because other materials rarely have finger skin properties. Therefore, even a non-finger object touches the sensing zone 613, the lack of the total internal reflection at the touch location may cause insufficient returned probe light to reach the optical sensor array to trigger flash wakeup operation.

The optical sensors for sensing optical fingerprints disclosed above can be used to capture high quality images of fingerprints to enable discrimination of small changes in captured fingerprints that are captured at different times. Notably, when a person presses a finger on the device, the contact with the top touch surface over the display screen may subject to changes due to changes in the pressing force. When the finger touches the sensing zone on the cover glass, changes in the touching force may cause several detectable changes at the optical sensor array: (1) fingerprint deforming, (2) a change in the contacting area, (3) fingerprint ridge widening, and (4) a change in the blood flow dynamics at the pressed area. Those changes can be optically captured and can be used to calculate the corresponding changes in the touch force. The touch force sensing adds more functions to the fingerprint sensing.

Referring to FIG. 33, the contact profile area increases with an increase in the press force, meanwhile the ridge-print expands with the increase in the press force. Conversely, the contact profile area decreases with a decrease in the press force, meanwhile the ridge-print contracts or shrinks with the decrease in the press force. FIG. 33 shows two different fingerprint patterns of the same finger under different press forces: the lightly pressed fingerprint 2301 and the heavily pressed fingerprint 3303. The returned probe light from a selected integration zone 3305 of the fingerprint on the touch surface can be captured by a portion of the optical sensors on the optical sensor array that correspond to the selected integration zone 3305 on the touch surface. The detected signals from those optical sensors are analyzed to extract useful information as further explained below.

When a finger touches the sensor surface, the finger tissues absorb the light power thus the receiving power integrated over the photo diode array is reduced. Especially in the case of total inner reflection mode that does not sense the low refractive index materials (water, sweat etc.), the sensor can be used to detect whether a finger touches the sensor or something else touches the sensor accidentally by analyzing the receiving power change trend. Based on this sensing process, the sensor can decide whether a touch is a real fingerprint touch and thus can detect whether to wake up the mobile device based on whether the touch is a real finger press. Because the detection is based on integration power detection, the light source for optical fingerprint sensing at a power saving mode.

In the detailed fingerprint map, when the press force increases, the fingerprint ridges expands, and more light is absorbed at the touch interface by the expanded fingerprint ridges. Therefore within a relatively small observing zone 3305, the integrated received light power change reflects the changes in the press force. Based on this, the press force can be detected.

Accordingly, by analyzing the integrated received probe light power change within a small zone, it is possible to monitor time-domain evolution of the fingerprint ridge pattern deformation. This information on the time-domain evolution of the fingerprint ridge pattern deformation can then be used to determine the time-domain evolution of the press force on the finger. In applications, the time-domain evolution of the press force by the finger of a person can be used to determine the dynamics of the user's interaction by the touch of the finger, including determining whether a person is pressing down on the touch surface or removing a pressed finger away from the touch surface. Those user interaction dynamics can be used to trigger certain operations of the mobile device or operations of certain apps on the mobile device. For example, the time-domain evolution of the press force by the finger of a person can be used to determine whether a touch by a person is an intended touch to operate the mobile device or an unintended touch by accident and, based on such determination, the mobile device control system can determine whether or not to wake up the mobile device in a sleep mode.

In addition, under different press forces, a finger of a living person in contact with the touch surface can exhibit different characteristics in the optical extinction ratio obtained at two different probe light wavelengths as explained with respect FIGS. 14A and 14B. Referring back to FIG. 33, the lightly pressed fingerprint 3301 may not significantly restrict the flow of the blood into the pressed portion of the finger and thus produces an optical extinction ratio obtained at two different probe light wavelengths that indicates a living person tissue. When the person presses the finger hard to produce the heavily pressed fingerprint 3303, the blood flow to the pressed finger portion may be severely reduced and, accordingly, the corresponding optical extinction ratio obtained at two different probe light wavelengths would be different from that of the lightly pressed fingerprint 3301. Therefore, the optical extinction ratios obtained at two different probe light wavelengths vary under different press forces and different blood flow conditions. Such variation is different from the optical extinction ratios obtained at two different probe light wavelengths from pressing with different forces of a fake fingerprint pattern of a man-made material.

Therefore, the optical extinction ratios obtained at two different probe light wavelengths can also be used to determine whether a touch is by a user's finger or something else. This determination can also be used to determine whether to wake up the mobile device in a sleep mode.

For yet another example, the disclosed optical sensor technology can be used to monitor the natural motions that a live person's finger tends to behave due to the person's natural movement or motion (either intended or unintended) or pulsing when the blood flows through the person's body in connection with the heartbeat. The wake-up operation or user authentication can be based on the combination of the both the optical sensing of the fingerprint pattern and the positive determination of the presence of a live person to enhance the access control. For yet another example, the optical sensor module may include a sensing function for measuring a glucose level or a degree of oxygen saturation based on optical sensing in the returned light from a finger or palm. As yet another example, as a person touches the display screen, a change in the touching force can be reflected in one or more ways, including fingerprint pattern deforming, a change in the contacting area between the finger and the screen surface, fingerprint ridge widening, or a blood flow dynamics change. Those and other changes can be measured by optical sensing based on the disclosed optical sensor technology and can be used to calculate the touch force. This touch force sensing can be used to add more functions to the optical sensor module beyond the fingerprint sensing.

The above optical sensor module designs and features are directed to collecting optical signal to the optical detectors in a under-screen optical sensor module and providing desired optical imaging quality (e.g., the detected image resolution) via an optical imaging by implementing at least one imaging lens or an array of collimators or pinholes. As mentioned above, background reduction techniques may be provided in a under-screen optical sensor module by performing certain controls and signal processing such as the two examples shown in FIGS. 12 and 13. In addition, one or more additional optical design features may be added to the above disclosed optical sensor module designs to reduce the background light based on background light filtering or adding extra illumination light sources. The different background light reduction techniques based on operation control/signal processing, optical filtering and adding extra illumination light sources can be combined in various ways in implementations.

The optical filtering technique for reducing the background light can be implemented in various optical sensor module designs disclosed in this document. While the general goal of inserting optical filters in the optical path of the optical sensor module is to reject the environment light wavelengths, such as near IR and partial of the red light and other undesired wavelengths, the specific implementation of such optical filters can vary based on the specific needs of each application. Such optical filters can be formed by forming optical filter coatings on selected surfaces of the optical parts in the optical path leading to the optical detector array 621, including, e.g., the display bottom surface, surfaces of other optical components such as optical prisms, the upper sensor surface of the optical detector array 621, etc. For example, human fingers absorb most of the energy of the wavelengths under a certain wavelength (e.g., around ~580 nm), if the optical filters are designed to reject the light in the wavelengths from this wavelength around ~580 nm to infrared, the undesired environment light influence can be greatly reduced.

FIG. 34 shows an example of the optical transmission spectral profiles of a typical human thumb and litter finger at several different optical wavelengths from around 525 nm to around 940 nm. For short wavelengths, such as wavelengths less than 610 nm, less than 0.5% of the environmental light may pass through the finger. Red light and near IR light have higher transmission. The transmission of the environmental light through a finger goes to a wide range of directions due to scattering by the finger tissues and thus can mix with the signal light to be detected by the under-screen optical sensor module. When operated under the sunlight, the undesired environmental light from the sunlight must be handled carefully due to the high optical power of the sunlight to reduce or minimize the adverse impact to the optical fingerprint sensor performance.

FIG. 35 illustrates influences of the background light in a under-screen optical sensor module 600*a*. The undesired environmental light that can adversely affect the optical fingerprint sensing may pass through different paths to reach the optical fingerprint sensor 600*a*. In some cases, the environmental light paths can be divided into different situations based on their optical paths: some light like 937 passes through the finger to enter the optical fingerprint sensor 600*a*, and some light like 937*a* does not pass through the finger but enters the optical fingerprint sensor 600*a* from one or more sides around the finger.

In the illustrated under-screen optical sensor module 600*a* for fingerprint sensing, a sensor package 600*b* is formed outside the under-screen optical sensor module 600*a* and may be formed of an optical opaque or absorptive material as a background blocker, at least for some of incident background light such as part large angled light in the background light like 937*a* that does not pass through the finger but enters the optical fingerprint sensor 600*a* from one or more sides around the finger.

With respect to the environmental light 937 that propagates through the finger 60*a*, the finger 60*a* absorbs some of the incident light so that part of the light 939 transmits through the finger 60*a* to reach the cover glass 431, and subsequently transmits through the cover glass 431 to reach the OLED TFT layers. The small holes 450 in the OLED TFT layers block most of such background light but a small portion of light 941 of such background light 939 passes through the small holes 450 to enter into the optical fingerprint sensor package 600*a*/600*b*. As discussed in FIG. 5D, such light can carry an optical transmissive pattern representing the fingerprint pattern of the finger based on interacting with the internal structures of the finger associated with the external fingerprint pattern on the external skin surface of the finger and thus may be used in some implementations for optical fingerprint sensing.

Some of the environmental light 937*a* propagates directly to the cover glass 431 without transmitting through the finger. Such transmitted light is refracted into the cover glass 431 and becomes light 939*a*. The OLED TFT layers small holes 450 allow a small part of light 941*a* to pass through to reach the optical fingerprint sensor package 600*a*/600*b*. This component of environmental light tends to include light components with large incident angles. The detection light paths can be designed so that this part of environmental light does not mix with the signal light.

The optical fingerprint sensor package can be designed to cause the optical sensor module 600*a* to receive only light from the detection light path window while blocking undesired environmental light at large incident angles. For example, in some implementations, the OLED light source of an OLED display can be used as the probe light source for illuminating the finger for optical fingerprint sensing. Under this design, only the top side of the optical sensor module 600*a* that is engaged to (e.g., being glued) the bottom of the OLED display module is open to receive light, such as the optical window 600*c* on the top of the optical fingerprint sensor package shown in FIG. 35 and the sensor bottom and side walls are not optically transparent within the detection light wavelength band so that the environmental light that can enter the optical fingerprint sensor is reduced. Therefore, for the environmental light that enters into the optical sensor module without first transmitting through the finger, the packaging of the optical sensor module can be designed to provide absorption or blockage of such light with light blocking side walls or properly designed optical receiving aperture so that such light, when reaching to the receiving optics material or the package material, is absorbed or blocked.

The undesired environmental light can include different wavelength components and thus such different environmental light components should be handled differently to reduce their impacts to the optical fingerprint sensing in implementing the disclosed technology.

For example, the undesired environmental light may include light components that transmit through the finger in the red (e.g., longer than 580 nm) and longer wavelengths and light components that do not transmit through the finger in the shorter wavelengths than the red wavelengths (e.g., less than 580 nm). Due to this wavelength-dependent absorption of the finger, the transmitted environmental light through the finger usually includes some near infrared (IR) and partial of the red light component. Therefore, the optical filtering can be included in the optical fingerprint sensor package to filter out the undesired environmental light that would otherwise enter the optical detector array.

An example design is to use one or more IR blocking filter coatings, e.g., an IR-cut filter coating, to reduce the IR or near IR light in the transmitted light from the finger. However, various IR-cut filters used for imaging devices normally only restrict wavelengths greater than 710 nm. When a device is exposed to direct or indirect sunlight, this filtering performance may not be good enough for reducing IR background light in optical fingerprint sensing. Suitable IR filtering coatings should extend the short end cut-off wavelength to shorter wavelengths below 710 nm, for example, 610 nm, in some applications.

Due to the spectral responses of various IR cut coatings, a single IR cut filter with the an extended working band to shorter wavelengths may not provide the desired IR blocking performance. In some filter designs for the under-screen optical sensor module, two or more optical filters may be used in combination to achieve the desired IR blocking performance in the sensor light paths. This use of two or more filters is in part because one significant technical issue is the strong background light from the natural day light from the sun. In the examples of disclosed optical sensors under the OLED display panel, an optical filtering mechanism can be built into the under-screen optical sensor stack to block or reduce the strong background light from the natural day light from the sun that enters the optical sensor array 600a. Accordingly, one or more optical filter layers may be integrated into the under-screen optical sensor stack above the optical sensor array to block the undesired background day light from the sun while allowing the illumination light for the optical fingerprint sensing to pass through to reach the optical sensor array.

For example, the illumination light may be in the visible range from the OLED emission for the display, e.g., from 400 nm to 650 nm, in some implementations and the one or more optical filters between the OLED panel and the optical sensor array can be optically transmissive to light between 400 nm and 650 nm while blocking light with optical wavelengths longer than 650 nm, including the strong IR light in the day light. In practice, some commercial optical filters have transmission bands that may not be desirable for this particular application for under screen optical sensors disclosed in this document. For example, some commercial multi-layer bandpass filters may block light above 600 nm but would have transmission peaks in the spectral range above 600 nm, e.g., optical transmission bands between 630 nm and 900 nm. Strong background light in the day light within such optical transmission bands can pass through to reach the optical sensor array and adversely affect the optical detection for optical fingerprint sensing. Those undesired optical transmission bands in such optical filters can be eliminated or reduced by combining two or more different optical filters together with different spectral ranges so that undesired optical transmission bands in one filter can be in the optical blocking spectral range in another optical filter in a way that the combination of two or more such filters can collectively eliminate or reduce the undesired optical transmission bands between 630 nm to 900 nm. Specifically, for example, two optical filters can be combined by using one filter to reject light from 610 nm through 1100 nm while transmitting visible light below 610 nm in wavelength and another filter to reject light in a shifted spectral range from 700 nm through 1100 nm while transmitting visible light under 700 nm in wavelength. This combination of two or more optical filters can be used to produce desired rejection of the background light at optical wavelengths longer than the upper transmission wavelength. Such optical filters may be coated over the spacer 917, collimator 617, and/or protection material 919 shown various examples, including FIG. 31B.

In some implementations, when using two or more optical filters as disclosed above, an optical absorbing material can be filled between the two filters to exhibit proper absorption for the rejected light band so that the bouncing light between the two optical filters can be absorbed. For example, one filter may be coated on spacer 917, and the other filter be coated on protection material 919, while the collimator 617 can be made optically absorbing to absorb the rejected light band by the two filters. As a specific example, a piece of blue glass that has high absorption from 610 nm to 1100 nm can be used as base of the filters. In this case the two filters are coated on up and down surfaces of the blue glass, and this component can be used as the spacer or the protection material.

In addition to using proper optical filtering for cutting background light in the red and IR ranges in an under-screen optical sensor module, the background light that should be reduced by the optical filtering may include light in the shorter wavelength spectral ranges including the UV wavelengths. In some implementations, the environmental light in the UV band should be reduced or eliminated because this band of light generate noises. This elimination can be realized by UV-cut off coating or by material absorption. Finger tissues, silicon, and black oil ink and others tend to absorb the UV light strongly. The material absorption of UV light can be used to reduce the UV light influence to the optical fingerprint sensing.

FIG. 36 shows an example of a design algorithm for designing the optical filtering in a under-screen optical sensor module in light of the above discussions for reducing background light. Hence in addition to designing proper optical filters in the optical path to the optical sensor module, additional design features for reducing the background light can be added to the design of the receiving optics for the optical detector array in the optical sensor module. Those optical filtering considerations and the further background light reduction via operation control and signal processing in operating such an optical sensor module can be combined to achieve the desired optical sensing performance.

In an under-screen optical sensor module having an optical collimator array or an optical pinhole array before the optical detector array, the optical collimator array or optical pinhole array is part of the receiving optics and can be designed with a small optical numerical aperture to reduce the background light that enters the optical detector array. FIG. 37 shows two examples in FIGS. 37A and 37B.

Referring to FIG. 37A, the collimator pinhole 951 can be designed to be optically transparent within the probe light band, the collimator wall materials 953 can be selected to absorb the light 955 that reaches the wall. If the collimator material is silicon, a blackened, light absorbing coating can be formed on each wall.

Referring to FIG. 37B, the pinhole array of pinholes 959 as part of the receiving optics can be constructed to have an effective numeral aperture to block the environmental light with large incident angles. A light blocking layer with an array of aperture restriction holes 961 may be formed below the array of the pinholes 959 so that the light 967 out of the effective numeral aperture can be blocked by the opaque section of the light blocking layer with the aperture restriction holes 961. The materials 963 and 965 that form the imaging camera pinholes 959 and the aperture restriction holes 961 can an optically opaque material or optically absorbing material such as a black oil ink, or an optical reflection material such as a metal film.

In some implementations, one or more optical filters may be used as the substrate for supporting the pinhole camera type optics so that multiple functional parts can be combined or integrated into one piece of hardware. This integration or combination of different background light reduction mechanism can reduce the device cost and may also reduce the device thickness.

A under-screen optical sensor module may also be operated with a sensor initialization process to reduce undesired influences of the background light. Like the techniques shown in FIGS. 12 and 13, this sensor initialization process is operational in nature. FIG. 38 illustrates an example of this sensor initialization process that measures a baseline background level at the optical sensor array each time a fingerprint is obtained. Before preforming the actual fingerprint sensing, in a dark room environment without any environmental light influence, the illumination light or the optical probe light for the optical sensing (the OLED display) is turned on, a finger simulator device is placed on the cover glass to record the image data. The finger simulator device is designed to simulate the finger skin reflection behavior but does not have any fingerprint pattern. This image data obtained from the finger simulator device is saved into memory as the base 1 data for the background light reduction processing in real sensing operations. This process can be a device calibration process done in factory before shipping the device.

In real time fingerprint sensing, the environmental influence is present. In operation, the illumination light or the optical probe light (e.g., the OLED screen) is first turned off to record the image data as base 2, which is made under a condition with the environmental light. This base 2 represents the total influence of all the environmental light residues. The sum of base 1 and base 2 gives the real-time base. Next, the illumination light or optical probe light is turned on to perform fingerprint sensing to capture a real-time signal which is a mixture of the real fingerprint signal from the fingerprint and the real-time base. A differential between the signal mixture and the real-time base can be performed as part of the signal processing to reduce the signal contribution by the environmental light so that the image quality of the fingerprint image can be obtained. The above example in FIG. 38 illustrates a method for operating an electronic device capable of detecting a fingerprint by optical sensing by operating an optical sensor module located below a touch display panel, that provides touch sensing operations for the device, to produce probe light to the illuminate a top transparent layer of the touch display panel to operate an optical sensor array inside the optical sensor module to obtain a first image from returned probe light from the top transparent layer. This method includes operating the optical sensor array inside the optical sensor module, while turning off the probe light, to obtain a second image under illumination with only environmental light without illuminating the top transparent layer of the touch display panel with any probe light; and processing the first image and the second image to remove an effect from the environmental light in an imaging operation of the device.

Based on the above, the undesired effect of the background light to the performance the under-screen optical sensor module can be mitigated in different techniques, including implementing optical filtering in the optical path to the optical sensor array to reduce the background light, designing the receiving optics for the optical sensor array to reduce the background light, or controlling the operations of the optical sensor module and signal processing to further reduce the effect of the background light to the optical sensing performance. Those different techniques may be used individually or in combination to meet the desired device performance.

In the disclosed optical sensing technology, in addition to using the OLED-emitted light from the OLED display module, one or more extra light sources can be used to illuminate the finger to be detected to improve the optical fingerprint sensing, e.g., by improving the signal to noise ratio in the detection. This inclusion of one or more extra illumination light sources to increase the optical signal level of the optical sensing signal carrying the fingerprint or other useful information beyond the signal level caused by the returned OLED display light for improving the optical sensing sensitivity can be used alone or in a combination with above disclosed techniques for reducing the amount of background light that enters the optical sensor array in an under-screen optical sensor module.

In this regard, an electronic device capable of detecting a fingerprint by optical sensing can be designed to include a device screen that provides touch sensing operations and includes a display panel structure having light emitting display pixels where each pixel is operable to emit light for forming a portion of a display image, a top transparent layer formed over the device screen as an interface for being touched by a user for the touch sensing operations and for transmitting the light from the display structure to display images to a user, and one or more extra illumination light sources located to provide additional illumination light to the top transparent layer formed over the device screen as the interface for being touched by a user. Such a device can further include an optical sensor module located below the display panel structure to receive light that is emitted by at least a portion of the light emitting display pixels of the display structure and by the one or more extra illumination light sources and is returned from the top transparent layer to detect a fingerprint, the optical sensor module including an optical sensor array that detects an image in the received light in the optical sensor module. In implementations, such as in various OLED screens, the display panel structure includes openings or holes between the light emitting display pixels of the display panel structure to allow the returned light to pass through the display panel structure to reach the optical sensor module, and the optical sensor module includes an array of optical collimators or an array of pinholes to collect the returned light from the display panel structure and to separate light from different locations in the top transparent layer while directing the collected returned light to the optical sensor array.

The first example for using extra illumination lighting is shown FIG. 9 which includes one or more extra light sources 614 that are attached to or glued into the same position or region of the viewing zone 613 to provide additional illumination to the sensing zone 615, thus increasing the light intensity in optical sensing operations. The extra light sources 614 may be of an expanded type, or be a collimated type so that all the points within the effective sensing zone 615 is illuminated. The extra light sources 614 may be a single element light source or an array of light sources. Furthermore, the OLED pixels in the viewing zone or the fingerprint illumination zone 613 in the OLED display module 433 may be operated a higher brightness level during the optical fingerprint sensing operation above the brightness level used for displaying images in the OLED display to boost the illumination level for the optical sensing operation.

FIGS. 39 and 40 show optical behaviors of various optical signals in an example of a under-screen optical sensor module having extra illumination light sources to supplement the optical fingerprint sensing illumination provided by the OLED display light.

The example in FIGS. 39 and 40 includes extra light sources 971 that are assembled in or adjacent the optical sensor module and are located generally under the designated fingerprint sensing area provided by the top transparent layer 431. Specifically in this example, two or more extra light sources 971 are placed outside the optical sensor module 600a and are outside the packaging walls 600b. Each extra light source 971 may be one light source or include multiple sources, for example, LED light sources. The extra light sources 971 may be operable to emit light at one single wavelength or at multiple wavelengths (for example, green LED, red LED, near IR LED). The extra light sources 971 may be modulated to produce modulated illumination light or be operated to turn on their emission at different phases. At the output port of each extra light source 971, a proper coupling material 972 is provided between each extra light source 971 and the OLED display module. The coupling material 972 may include a suitable optically transparent material to allow the probe light 973 from the extra light source 971 to be coupled into the display towards the finger on the cover 431 surface. In some implementations, it may be desirable to avoid large output angles of the probe light 973 in the display and the coupling material 972 may be configured to limit the probe light's numeral aperture. The coupling material 972 may be a low index material such as an air gap and may be structured to have a desired output aperture that limits the output angle of the probe light 973 in the display.

The small holes 450 in the TFT layers of the OLED display module scatter the probe light beam 973 into various directions. As shown in FIG. 39, some scattered light 977 propagates towards the optical sensor module 660a at large angles and is less likely to enter the optical sensor module due to the absorption or blocking by the small aperture of the receiving optics of the optical sensor module 660a. Some scattered light 977a propagates towards other directions that are away from the aperture of the optical sensor module 660a and thus does not affect the optical sensing. Notably, a portion of the probe light 973 from each extra light source 971 passes through the TFT layers as the probe light 975 towards the top surface of the top transparent layer 431. This probe light 975 can interact with the finger over the top cover 431 in two ways for optical fingerprint sensing. First, a portion of the probe light 875 may be reflected back as explained in FIGS. 5A and 5B to the optical sensor module 600a as an optical reflective pattern representing the external fingerprint pattern formed by the ridges and valleys. Second, another portion of the probe light 875 can be coupled into the finger 60a by optical transmission as explained in FIGS. 5A and 5B with reference to the scattered light 191 towards the under-screen optical sensor module to carry an optical transmissive pattern associated with the fingerprint pattern and the internal tissue structures as explained in FIGS. 5C and 5D. The tissues in the finger 60a scatter the probe light 975 to produce scattered probe light 979 in various directions, including back scattered probe light 981 with the optical transmissive pattern for optical fingerprint sensing. The back scattered probe light 981 propagates back through the top transparent layer 431 to enter the TFT layers towards the optical sensor module 600a. The TFT layers refract or scatter the back scattered probe light 981, a portion of which becomes the probe light component 983 that can be detected by the photo-detector array in the optical sensor module 600a.

As explained with respect to FIGS. 5C and 5D, the back scattered probe light 981 from the probe light 979 propagates through the finger skin, the fingerprint ridge area and valley area manifest light signals with a spatial varying brightness pattern in an optical transmissive pattern due to interactions with the internal finger tissues associated with the external ridges and valleys of the finger and this brightness contrast forms part of the fingerprint pattern and is caused by the finger tissue absorption, refraction, and reflection, by finger skin structure shading, and by reflectance difference at the finger skin-display cover glass interface. Because of the complicated mechanism of the fingerprint contrast, the fingerprint can be detected even if the finger is dry, wet, or dirty.

FIG. 40 further shows that background light present at the device can generally include two different portions the environmental or background light 937 incident to the finger 60a and environmental or background light 937c incident to the top transparent layer 431 without entering the finger 60a. Since the environmental or background light 937 propagates into finger 60a, the finger tissues scatter the received background light 937 as scattered background light 937b in different directions and mixes with the probe light 979. Some of the scattered light 939 in the scattered background light 937b propagates back towards the optical sensor module 600a through the finger 60a. A portion of the environmental light 937c that does not go through the finger 60a, if is permitted to enter the optical sensor module 600a, it could adversely impact the optical sensing operation of the optical sensor module 600a. Therefore, it is desirable to reduce or eliminate the amount of the environmental light from entering the optical sensor module 600a by optical filtering, by the design of the receiving optics or by controlling the operation and signal processing of the optical sensor module as discussed above with reference to FIGS. 36-38.

As exampled with respect to FIG. 5D, the scattered light 939 in the scattered background light 937b propagates towards the optical sensor module 600a through the finger 60a and thus carrying an optical transmissive pattern due to interactions with the finger including internal tissues associated with the external ridges and valleys of the finger. In some implementations, this light 939 from the environmental or background light may be detected for optical fingerprint sensing based on its optical transmissive pattern.

FIG. 41 shows an example of a design algorithm for designing the optical filtering in a under-screen optical sensor module with extra light sources for optical sensing. The considerations for the design in FIG. 41 are to reduce or eliminate the environmental light at the optical sensor module, including environmental light that transmits through the finger and that does not transmit through the finger. This is similar to the design shown in FIG. 36. Because the absorption of the finger, the transmitted environmental light can include some near IR and partial of the red light component. Therefore, the optical filter coatings should be designed to handle the remained environmental light. An example design is to use RED/IR band pass filtering since the red and near IR light can travel into relatively long distances in finger tissues. Considering that the sunlight is strong, the band pass filter can be designed based on the probe light source wavelength band. As discussed above in connection with FIG. 36, the UV band should also be eliminated because this band of light generate noises. This elimination can be realized by UV-cut off coating or by material absorption. Finger tissue, silicon, and black oil ink etc. absorbs UV light strongly. In some designs, the material absorption may be used to eliminate the UV light influence. For the environmental light that does not transmit through the finger, the extinction may be achieved by designing the receiving optics absorption. This part of light features large incident angles that can be blocked by the properly designed receiving numeral aperture.

The techniques for reducing the background light in FIGS. 37 and 38 can also be applied to the optical sensor module with extra light sources for optical sensing in FIGS. 39 and 40 for reduction of the environmental light.

When extra light sources are provided for optical sensing, the illumination power for optical sensing is no longer limited by the optical power from the OLED display light. Such extra light sources can be designed to provide sufficient illumination for optical sensing to improve the optical detection signal to noise ration to offset the environmental light influence. In implantations, the extra light sources can be modulated without affecting the display function and lifetime. In addition, the extra light sources can be flashed with high output power for a short time during the fingerprint sensing so as to obtain optimized detection. In addition, the use of extra light sources can provide flexibility in the determination of whether a detected finger is a live finger so that fake fingerprint detection can be avoided. For example, green LEDs and near IR LEDs may be used as extra light sources to also assist the live finger detection as explained with reference to FIGS. 14A and 14B where finger tissues absorb the green light strongly so that the finger image manifests a desired large brightness gradient and the near IR light illuminates all through the finger so that the finger image brightness appears more uniform.

Specific Examples for Placing Extra Illumination Light Sources for Obtaining Optical Transmissive Patterns FIGS. 42 through 45 show examples of under-OLED optical sensor module designs for placing extra illumination light sources to obtain optical transmissive pattern by directing the illumination light to transmit through a finger under the detection.

FIG. 42A shows an example for placing 4 extra illumination light sources in two orthogonal directions on opposite sides of the fingerprint sensing area based on the design in FIG. 5D. This example is one implementation of an electronic device capable of detecting a fingerprint by optical sensing that includes a display panel that includes light emitting display pixels operable to emit light for displaying images; a top transparent layer formed over the display panel as an interface for user touch operations and for transmitting the light from the display panel to display images, the top transparent layer including a designated fingerprint sensing area for a user to place a finger for fingerprint sensing; and an optical sensor module located below the display panel and underneath the designated fingerprint sensing area on the top transparent layer to receive light that is emitted by at least a portion of the light emitting display pixels and is returned from the top transparent layer to detect a fingerprint. The optical sensor module includes an optical sensor array of optical detectors to convert the returned light from the display panel that carries a fingerprint pattern of the user into detector signals representing the fingerprint pattern. This device further includes extra illumination light sources located outside the optical sensor module at different locations to produce different illumination probe beams to illuminate the designated fingerprint sensing area on the top transparent layer in different illumination directions. Each extra illumination light source can be structured to produce probe light in an optical spectral range with respect to which tissues of a human finger exhibit optical transmission to allow probe light in each illumination probe beam to enter a user finger over the designated fingerprint sensing area on the top transparent layer to produce scattered probe light by scattering of tissues inside the finger that propagates towards and passes the top transparent layer to carry both (1) fingerprint pattern information and (2) different fingerprint topographical information associated with the different illumination directions, respectively, caused by transmission through internal tissues of ridges and valleys of the finger. A probe illumination control circuit is coupled to control the extra illumination light sources to sequentially turn on and off in generating the different illumination probe beams at different times, one beam at a time, so that the optical sensor module located below the display panel is operable to sequentially detect the scattered probe light from the different illumination probe beams to capture both (1) the fingerprint pattern information and (2) the different fingerprint topographical information associated with the different illumination directions, respectively. The examples of under-OLED optical sensor module designs for placing extra illumination light sources to obtain optical transmissive patterns by directing the illumination light to transmit through a finger under the detection may also be used with other display panel designs, including, for example, LCD display panels. Specific implementations of the extra illumination light sources for obtaining optical transmissive patterns may vary from one design to another. FIG. 42 B shows an operational flow for operating various devices with a display panel that may be implemented in various configurations such as OLED, LCD or others. The method or operation in FIG. 42B includes operating an electronic device to detect a fingerprint by optical sensing and the electronic device includes a display panel that displays images, a top transparent layer formed over the display panel as an interface for user touch operations and for transmitting the light from the display panel to display images, and an optical sensor array of optical detectors located under the display panel where the display panel.

FIG. 42B shows that a first illumination probe beam is directed to illuminate a designated fingerprint sensing area over the top transparent layer in a first illumination direction and to enter a user finger over the designated fingerprint sensing area to produce first scattered probe light by scattering of tissues inside the finger that propagates towards and passes the top transparent layer by transmission through internal tissues of ridges and valleys of the finger to carry both (1) a first 2-dimensional transmissive pattern representing a fingerprint pattern formed by bridges and valleys of the finger, and (2) a first fingerprint topographical pattern that is associated with the illumination of internal tissues of ridges and valleys of the finger in the first illumination direction and is embedded within the first 2-dimensional transmissive pattern. While under the illumination by the first illumination probe beam, the optical sensor array is operated to detect transmitted part of the first scattered probe light that passes through the top transparent layer and the display panel to reach the optical sensor array so as to capture both (1) the first 2-dimensional transmissive pattern, and (2) the first fingerprint topographical pattern.

Next, a second illumination probe beam, while turning off the first illumination light source, is directed to illuminate the designated fingerprint sensing area over the top transparent layer in a second, different illumination direction and to enter the user finger to produce second scattered probe light by scattering of tissues inside the finger that propagates towards and passes the top transparent layer by transmission through internal tissues of ridges and valleys of the finger to carry both (1) a second 2-dimensional transmissive pattern representing the fingerprint pattern, and (2) a second fingerprint topographical pattern that is associated with the illumination of the internal tissues of ridges and valleys of the finger in the second illumination direction and that is embedded within the second 2-dimensional transmissive pattern. The second topographical pattern is different from the first topographical pattern due to different beam directions of the first and second illumination probe beams. See FIG. 5C and FIG. 5D. While under the illumination by the second illumination probe beam, the optical sensor array is operated to detect transmitted part of the second scattered probe light that passes through the top transparent layer and the display panel to reach the optical sensor array so as to capture both (1) the second 2-dimensional transmissive pattern, and (2) the second fingerprint topographical pattern.

Subsequently, a detected fingerprint pattern is constructed from the first and second transmissive patterns and the first and second fingerprint topographical patterns are processed to determine whether the detected fingerprint pattern is from a natural finger.

Turning now FIGS. 43, 44 and 45, extra illumination light sources may be placed at various locations outside the optical sensor module to direct the illumination beams into a finger in different directions to provide different shadowing in the captured optical transmissive patterns explained in FIG. 5D.

In FIG. 43, at least one extra illumination light source 971a is placed above the display panel and the top transparent layer 431 and is away from the designed fingerprint sensing area to direct the illumination beam 937 to the finger in the designated fingerprint sensing area above the top transparent layer 431 to enter the finger and to cause scattering inside the finger which contributes to the part of the signal 981 with an optical transmissive pattern for the optical fingerprint sensing. Two or more such light sources 971a may be so placed. FIG. 43 further shows that extra illumination light sources 971 are also placed under the designated fingerprint sensing area as explained in FIGS. 39 and 40.

In FIG. 44, at least one extra illumination light source 971b is placed below the top transparent layer 431 and is away from the designed fingerprint sensing area to direct the illumination beam 937 to one side of the finger in the designated fingerprint sensing area above the top transparent layer 431 to enter the finger and to cause scattering inside the finger which contributes to the part of the signal 981 with an optical transmissive pattern for the optical fingerprint sensing. In this example, the one extra illumination light source 971b is placed side by side with the display panel below the top transparent layer 431. Two or more such light sources 971a may be so placed. FIG. 44 further shows that extra illumination light sources 971 are also placed under the designated fingerprint sensing area as explained in FIGS. 39 and 40.

In FIG. 45, at least one extra illumination light source 971b is placed below the display panel and is away from the designed fingerprint sensing area to direct the illumination beam 937 to one side of the finger in the designated fingerprint sensing area above the top transparent layer 431 to enter the finger and to cause scattering inside the finger which contributes to the part of the signal 981 with an optical transmissive pattern for the optical fingerprint sensing. In this example, the one extra illumination light source 971b is placed side by side with the display panel below the top transparent layer 431. Two or more such light sources 971a may be so placed. FIG. 45 further shows that extra illumination light sources 971 are also placed under the designated fingerprint sensing area as explained in FIGS. 39 and 40.

When extra illumination light sources are provided for optical sensing, the illumination power for optical sensing is no longer limited by the optical power from the OLED display light. Such extra illumination light sources can be designed to provide sufficient illumination for optical sensing to improve the optical detection signal to noise ration to offset the environmental light influence. In implantations, the extra illumination light sources can be modulated without affecting the display function and lifetime. In addition, the extra illumination light sources can be flashed with high output power for a short time during the fingerprint sensing so as to obtain optimized detection. Furthermore, the use of extra illumination light sources can provide flexibility in the determination of whether a detected finger is a live finger so that fake fingerprint detection can be avoided. For example, green LEDs and near IR LEDs may be used as extra light sources to also assist the live finger detection where finger tissues absorb the green light strongly so that the finger image manifests a desired large brightness gradient and the near IR light illuminates all through the finger so that the finger image brightness appears more uniform. For another example, extra illumination light sources can be used to provide optical fingerprint sensing based on optical transmissive patterns by optical transmission of the probe illumination light through the internal tissues associated with the external finger ridges and valleys as explained in FIGS. 5A through 5D.

Examples of Optical Imaging in Under-Screen Optical Sensor Module Based on a Pinhole-Lens Assembly The optical imaging optics of the optical sensor module under the display panel structure can be implemented in various ways as shown by some of the examples above, including using a lens with a folded optical path to form an imaging system for the under-screen optical sensor module and using an array of optical collimators for imaging without an imaging lens. Notably, an imagine module having at least one imaging lens designed to achieve the optical imaging of the illuminated touched portion of a finger onto the optical sensor array in the under-screen optical sensor module. The lensing effect of the imaging module is in part for controlling the spatial spreading of the returned light that may spatially scramble returned light from different locations on the touched portion of the finger at the optical sensor array so that the spatial information on the returned light corresponding to the fingerprint pattern on a finger can be preserved by the imaging lens with a desired spatial imaging resolution when the imaging lens directs the returned light to reach the optical sensor array. The spatial imaging resolution of an imaging module having a single imaging lens or an assembly of two or more imaging lenses is proportional to the numerical aperture of the imaging module. Accordingly, a high-resolution imaging lens requires a large numerical aperture and thus a lens with a large diameter. This aspect of a lens-based imaging module inevitably requires a bulking lens system to produce a high-resolution imaging system. In addition, a given imaging lens has a limited field of view which increases as the focal length decreases and decreases as the focal length increases.

In many fingerprint sensing applications such as optical fingerprint sensors implemented under a display screen in a mobile device, it is desirable to have a compact imaging system with a high spatial imaging resolution and a large field of view. In view of the trade-offs in various imaging features of a lens-based imaging system discussed above, a compact optical imaging system for optical fingerprint sensing is provided below by combining a lens-based imaging system to achieve a high spatial imaging resolution via the lens and a reduced size in the captured image at the optical detector array to reduce the size the optical detector array via the same lens. The pinhole is placed in front of the lens to produce a field of view in optical imaging by effectuating a pinhole camera while without requiring a large diameter lens. A conventional pinhole camera can include a small aperture for optical imaging and can produce a large field of view while suffering a limited image brightness due to the small aperture and a low spatial imaging resolution. A combination of an imaging lens and a pinhole camera, when properly designed, can benefit from the high spatial imaging resolution of the imaging lens and the large field of view of the pinhole camera.

FIG. 46 shows one example of an optical sensor module 620 placed under an OLED display screen where a pinhole and a lens used to form the optical imaging system for the optical sensor module 620. In this example, the optical sensing module 620 is a compact module by using a micro lens 621e with a small diameter that can be about the same size of the pinhole so slightly larger than the pinhole. The micro lens 621e is engaged to a pinhole structure 621g that is optically opaque and may be a layer of a blackened or metal material formed on a surface of a pinhole substrate 621f of an optically transparent material with an opening as the pinhole 643. The micro lens 621e is placed on the lower side of the pinhole substrate 621f. In operation, the optical layers above the pinhole 643 in the pinhole structure 621g are structured to produce a large optical field of view in collecting the returned light from the OLED display panel and to transmit the collected light towards the optical sensor array 623e. The optical detectors in the optical sensor array 623e respond to the received optical pattern to produce detector signals and a detector circuitry module 623f is coupled to the optical sensor array 623e to receive and process the detectors signals. detector circuitry module 623f may include, in some implementations, a flexible printed circuit (PFC). The micro lens 621e receives the transmitted light from the pinhole and to focus the received light onto the optical sensor array 623e for optical imaging at an enhanced spatial imaging resolution at the optical sensor array 623e when compared to a lower spatial imaging resolution of the pinhole in projecting light onto the optical sensor array 623e without the micro lens 621e. In this design, the low resolution of the pinhole is compensated by using the micro lens 621e and the limited field of view of the micro lens 621e is compensated by the large field of view of the pinhole 643.

In the illustrated example of using the pinhole-lens assembly for optical imaging in FIG. 46, the object plane of the pinhole-lens assembly is near the top effective sensing zone 615 on the top surface of the transparent layer 431 such as a cover glass for the touch sensing OLED display panel and the imaging plane of the pinhole-lens assembly is the receiving surface of the optical detectors of the optical sensor array 623e. In addition to the pinhole substrate 621f, an optically transparent spacer 618e with a refractive index lower than that of the pinhole substrate 621f is provided between the pinhole substrate 621f and the OLED display panel. This use of a lower index material above the pinhole substrate 621f is part of the optical design to achieve a large field of view for receiving light from the OLED display panel. In some implementations, the lower-index spacer 618e may be an air gap. This design provides an optical interface of two different optical materials between lower-index spacer 618e and the higher-index pinhole substrate 621f and the optical refraction at this interface converts a large field of view (FOV) (e.g., around 140 degree in some cases) of incident light from the OLED display panel in the lower-index spacer 618e into a smaller FOV in the higher-index pinhole substrate 621f. Accordingly, the output light rays produced by the pinhole-lens assembly have a relatively small FOV.

This design of reducing the FOV is advantageous in several aspects. First, the optical input FOV in the lower-index spacer 618e of the optical sensor module 620 is a large FOV. Second, the actual FOV handled at by the pinhole-lens assembly located below the higher-index pinhole substrate 621f is a reduced FOV with respect to the optical input FOV so that light rays with large incident angles are limited by this reduced FOV. This is beneficial because image distortions caused by light rays at large incident angles at the pinhole-lens assembly are reduced by this reduced FOV. In addition, this reduced FOV at the pinhole-lens assembly reduces the undesired pinhole shading effect that would distort the brightness distribution of the image at the optical sensor array.

Different from a convention pinhole camera with uses a pinhole with a diameter around 40 microns in some pinhole camera designs, the pinhole 643 is designed to have a diameter much larger than the typical size of a pinhole in a pinhole camera, e.g., greater than 100 microns, or 200 microns (e.g., 250 microns) in some designs. In this combination of the lens and the pinhole, the use of the high-index material for the pinhole substrate 612f just above the pinhole 643 and the use of the lower-index layer 618e above the pinhole substrate 612f allows the pinhole 643 to have a diameter much larger than the typical size of a pinhole in a pinhole camera while still achieving a large FOV. For example, in some implementations, the diameter of the pinhole 643 may be about the same as or similar to the radius of curvature of the curve surface of the lens 621e when structured as a half ball lens with a flat surface facing the pinhole 643 and a partial spherical surface that directs the light from the pinhole 643 towards the photodetector array 621e.

Additional design features can also be implemented to improve the overall optical performance and the compactness of the optical imaging system based on the pinhole-lens assembly. For example, as illustrated in FIG. 25, additional optical layers can be placed between the lens-pinhole assembly and the photodiode array 623e. In this example, an optically transparent spacer 621h and a protection material 623g are provided in the light path from the pinhole-lens assembly to the optical sensor array 623e. In some implementations, the spacer 621*h* may be a low-index layer such as an air gap, and the protection material 623*g* may be a layer covering the top of the optical detectors of the optical sensor array 623*e* and having a refractive index higher than that of the spacer 621*h*. The layers 621*h* and 623*g* can be structured to reduce or eliminate the imaging distortion at the optical sensor array 623*e*. When light is refracted at media interfaces, the nonlinearity in the directions of refracted rays exists and creates image distortions at the optical sensor array 623*e*. Such distortions become more pronounced when the incident angles are large. To reduce such distortions, the optical thickness ratio of spacer 621*h* and 623*g* can be selected in light of the optical structure of the pinhole-lens assembly and the optical objective field of the pinhole-lens assembly (e.g., the optical layers from the top sensing surface of the top glass layer 431 to the pinhole substrate 621*f*).

Optical distortions occur at each interface of different optical materials along the optical path of light from the top of the OLED display panel to the optical sensor array 623*e*. One design technique for reducing such optical distortions is to provide optically matching structures on lower side of the pinhole-lens assembly (i.e., the optical layers on the imaging side of the pinhole-lens assembly) to corresponding to optical structures on the upper side of the pinhole-lens assembly (i.e., the optical layers on the object side of the pinhole-lens assembly) so that an optical distortion incurred at one interface along the optical path from the OLED panel to the pinhole-lens assembly in the object side of the pinhole-lens assembly is countered or offset by optical refraction at a matching interface along the optical path from the pinhole-lens assembly to the optical sensor array 623*e* in the imaging side of the pinhole-lens assembly. The optical matching layers in the imaging side of the pinhole-lens assembly are designed by taking into account of the optical power of the lens in the pinhole-lens assembly.

FIG. 47 illustrates an optical imaging system with the pinhole-lens assembly having a series of layers (633, 635, 637, 639, 641 etc.) above the pinhole 643 and corresponding material layers 645, 647, 649 etc. below the pinhole 643. In a pinhole imaging system with the pinhole 643 along without the lens 621*e*, optical distortions are present when the media are not matched between the object and the image fields. Such optical distortions may be in form of a barrel distortion when the FOV is large. For example, as illustrated in FIG. 47, an object 651 with a grid pattern as shown is placed over the top sensing surface instead of a finger 447 to test the distortions. The barrel distortion caused by the un-matched optical layers between the object and the image fields of the pinhole 643 may be represented by the distorted pattern 653. Such distortions are undesirable because they directly impact the accuracy of the fingerprint pattern captured by the optical sensor array 623*e*. It is noted that the level of such distortions is usually higher in the central part of the imaging field at the optical sensor array 623*e* than the peripheral part, as illustrated by the distorted image 653.

To mitigate such distortions, material layers 645, 647, 649 etc. below the pinhole in the imaging field can be structured in terms of their refractive indices and thickness values to reverse the distortions introduced by the material layers in the object side. This is achieved by matching the refraction behavior at large incident angles so as to correct the image to be linearly formed on the detector surface. For example, in a pinhole imaging system with an imaging magnification at ⅕, if there are a glass layer of 2 mm thick and an air gap layer of 1 mm thick above the pinhole 643, a glass layer of 0.4 mm thick and an air gap of 0.25 mm thick can be provided below the pinhole 643 and above the optical sensor array 623*e* to reduce the optical distortions at the optical sensor array 623*e*. This technique can be applied to provide matching layers below the pinhole 643 for complex material layers above the pinhole 643.

The pinhole-lens assembly for optical imaging in the example in FIG. 46 can achieve a higher spatial imaging resolution to capture fine features in the captured images beyond the spatial imaging resolution of the system with the pinhole 643 alone without the lens 621*e*. This higher spatial imaging resolution is a result of having the lens 621*e*. FIG. 48 illustrates the imaging operation of the pinhole alone and the imaging operation of the pinhole-lens assembly.

Referring to FIG. 48A in FIG. 48 showing a pinhole imaging system without the lens, the pinhole 643 diffracts the incident light beam 661 to produce a diffracted the output light beam 673 that is divergent due to the diffraction by the pinhole 643. This divergent light beam 673 forms an image light spot 679 at the imaging plane 667 that reflects the resolution of this imaging system.

FIG. 48B in FIG. 48 shows a micro lens 621*e* is added under the pinhole 643 and the curvature of the micro lens 621*e* modifies the wave-front of the light beam diffracted by the pinhole 643 to produce a light spot 681 at the imaging plane 667 which is smaller than the light spot 679 produced by the pinhole 643 alone without the lens 621*e*.

The pinhole-lens assembly can be implemented to provide a compact optical sensor module 620 in the example in FIG. 25. Due to the refraction at the media interfaces, the light propagation angle can be controlled by using different optical materials. For example, as shown in FIG. 28, if the refractive index n1 in the media above the pinhole substrate 621*f* is lower than the refractive index n2 of the pinhole substrate 621*f*, a light beam 683 with a large incident angle is bent to a beam 685 with a smaller angle after entering the pinhole substrate 621*f*. Therefore, an extremely large field of view can be realized for receiving input light at the object side of the pinhole-lens assembly by using a higher index material for the pinhole substrate 621*f*. In some implementations, a large FOV (e.g., close to or above 140 degrees) may be achieved by using a high-index material for the pinhole substrate 621*f* to create a sufficiently large difference between the refractive indices the pinhole substrate 621*f* and the layer above the pinhole substrate 621*f*.

The above design for achieving a large diffraction bending of light rays at the top surface of the pinhole substrate 621*f* can be used to reduce the thickness of the optical sensor module by incorporating some low refractive index gaps (such as air gaps) in the light path. In addition, the image uniformity of the image from the pinhole-lens assembly can be improved because the tilting angles of light rays entering the lens underneath the pinhole substrate are reduced with a smaller FOV due to the large refraction on the top of the pinhole substrate 621*e*.

In the pinhole-lens assembly, the micro lens is placed underneath the pinhole 643 and thus the optical aperture of the micro lens is small due to the small opening of the pinhole 643. As such, the micro lens exhibits lower aberrations because light rays from the pinhole 643 collected by the micro lens generally are close to the axis of the curved surfaces of the micro lens.

In implementing this pinhole-lens assembly, the center of the pinhole 643 is placed at or close to the center of the micro lens surface. In the example in FIG. 49, a half ball lens is shown as an example and is engaged onto (e.g., being glued) a pinhole board to achieve this configuration. The flat surface of the half ball lens 621*e* faces up to engage to the pinhole 643 and the center of the flat surface of the half ball lens 621*e* is at or near the center of the pinhole 643. Under this design, any incident light, at both small or large incident angles to the flat surface of the half ball lens 621*e* via the pinhole 643, would have its light ray direction to coincide with a radial direction of the half ball lens 621*e* which is the optical axis of the lens in that direction. This configuration reduces optical aberrations. For light beams 663 and 683 with different incident angles at the top of the pinhole substrate 621*f*, their light paths are modified after entering the pinhole substrate 621*f* to be close to the respective optical axes 689 and 691 of the half ball lens surface. Therefore, under this specific design, the image light spots 681 and 693 exhibit low optical aberrations.

The pinhole-lens assembly is subject to an aperture shading effect which causes the final image at the imaging plane (the optical sensor array 623*e*) to appear brighter in the center and darker in the peripheral area with a gradual change in brightness along the radial direction from the center towards the peripheral area. This effect degrades the image captured at the optical sensor array 623*e* and can be reduced by using a corrective optical filtering that modifies the spatial brightness distribution. For example, an optical filter with a spatial gradient transmission profile can be inserted in the optical path of the light received by the optical sensor module, e.g., a location between the OLED display panel and the optical sensor array. This gradient transmission filter is structured to exhibit a high optical attenuation at or near a center of the pinhole and a decreasing optical attenuation from the center of the pinhole radially outward to counter a spatial variation of an optical intensity distribution of light caused by the pinhole.

FIG. 50 shows an example of an optical attenuation profile for such a gradient transmission filter with a radial gradient attenuation that decreases from the center towards the edge.

In implementations, the gradient transmission filter may include one or more coatings may be made on a surface of the light path to correct the image brightness non-uniformity, e.g., the display bottom surface, the module parts surface, or top surface of the optical sensor array. In addition to countering the spatial un-uniformity by the aperture shading effect, the filter may be further configured to correct other types of brightness non-uniformity and may also include features that can reduce other optical distortions and optical aberrations.

As discussed above, undesired background or environmental light may adversely affect the optical sensing operation and can be reduced by various techniques. Techniques for reducing the effect of the environment light can also be used to improve the performance of such an under-screen optical sensor module based on the pinhole-lens assembly.

For example, the use of a light shielding package outside the optical sensor module can be also applied to an under-screen optical sensor module based on the pinhole-lens assembly. FIG. 51 shows an example in which the sensor module 620 is integrated into a package 620*a* to block the environmental light from entering the optical sensor array. A window is formed in the protection layer of the display. The module 620 and 620*a* is installed under the protection layer. A spacer material 631 may be applied to modify the view of the display and provide protection of the display. If the spacer 618*e* is an air gap, the sensor module does not contact the display directly so that the display is not affected during the usage.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. An electronic device capable of detecting a fingerprint by optical sensing, comprising:

a display panel that displays images;

a top transparent layer formed over the display panel as an interface for user touch operations and for transmitting the light from the display panel to display images, the top transparent layer including a designated fingerprint sensing area for a user to place a finger for fingerprint sensing;

an optical sensor module located below the display panel and underneath the designated fingerprint sensing area on the top transparent layer to receive light from the top transparent layer to detect a fingerprint, wherein the optical sensor module includes an optical sensor array of optical detectors to convert the received light that carries a fingerprint pattern of the user into detector signals representing the fingerprint pattern;

extra illumination light sources, separated from the display panel and located outside the optical sensor module at different locations to produce different illumination probe beams to illuminate the designated fingerprint sensing area on the top transparent layer in different illumination directions, each extra illumination light source structured to produce probe light in an optical spectral range with respect to which tissues of a human finger exhibit optical transmission to allow probe light in each illumination probe beam to enter a user finger over the designated fingerprint sensing area on the top transparent layer to produce scattered probe light by scattering of tissues inside the finger that propagates towards and passes the top transparent layer by transmission through internal tissues of ridges and valleys of the finger to carry both (1) 2-dimensional fingerprint pattern information of a 2-dimensional fingerprint pattern of ridges and valleys of the finger present in the designated fingerprint sensing area and (2) different fingerprint topographical information associated with illumination direction-dependent spatial shadowing patterns due to illumination of internal tissues of the ridges and valleys of the finger at the different illumination directions, respectively, caused by transmission of probe light of each of the different illumination probe beams through a skin of the finger such that scattering of the probe light under the skin of the finger by the internal tissues renders the different fingerprint topographical information associated with illumination direction-dependent spatial shadowing patterns to contain 3-dimensional information of the internal tissues of the ridges and valleys of the finger that is not captured by the 2-dimensional fingerprint pattern information of the 2-dimensional fingerprint pattern of the ridges and valleys of the finger; and a probe illumination control circuit coupled to control the extra illumination light sources to sequentially turn on and off in generating the different illumination probe beams at different times, one beam at one of the different illumination direction at a time, so that the optical sensor module located below the display panel is operable to sequentially detect the scattered probe light from the different illumination probe beams to capture both (1) the 2-dimensional fingerprint pattern information, (2) the different fingerprint topographical information associated with illumination direction-dependent spatial shadowing patterns due to illumination at the different illumination directions, respectively, and (3) to process different fingerprint topographical information to extract a spatial shift between different topographical patterns due to a difference in the different illumination directions and to determine whether the detected fingerprint pattern is from a natural finger based on the extracted spatial shift between the different topographical patterns.

2. The device as in claim 1, wherein:
extra illumination light sources emit probe light between 590 nm and 950 nm in which a human finger exhibits optical transmission.

3. The device as in claim 1, wherein:
the extra illumination light sources are located below the top transparent layer and above the optical sensor module to direct the different illumination probe beams to pass through the top transparent layer to illuminate a finger above the designated fingerprint sensing area.

4. The device as in claim 1, wherein:
the extra illumination light sources are located above the top transparent layer to direct the different illumination probe beams to pass through space above the top transparent layer to illuminate a finger above the designated fingerprint sensing area.

5. The device as in claim 1, wherein:
each extra illumination light source further emits second probe light at a second different wavelength; and
the device includes a controller that processes optical detector signals from the optical sensor module from sensing the probe light and the second probe light to determine whether a detected fingerprint is from a finger of a live person.

6. The device as in claim 1, wherein:
the extra illumination light sources include a first illumination light source and a second illumination light source that are placed in opposite directions with respect the designated fingerprint sensing area on the top transparent layer to cause the illumination probe beams from the first and second illumination light sources to be directed to the designated fingerprint sensing area in opposite directions.

7. The device as in claim 1, comprising:
additional extra illumination light sources located below the display panel at a position that is underneath the designated fingerprint sensing area on the top transparent layer to produce additional illumination probe light beams to illuminate the designated fingerprint sensing area to cause optical reflection at a user finger in contact with the designated fingerprint sensing area towards the optical sensor module for fingerprint sensing.

8. The device as in claim 1, wherein:
the optical sensor module includes:
a pinhole layer located between the display panel and the optical sensor array and structured to include a pinhole that is structured to produce a large optical field of view in collecting the light and to transmit the collected light towards the optical sensor array, and
a lens located between the pinhole layer and the optical sensor array to receive the transmitted light from the pinhole and to focus the received light onto the optical sensor array for optical imaging at an enhanced spatial imaging resolution at the optical sensor array.

9. The device as in claim 1, wherein:
the optical sensor module includes an array of optical collimators located between the display panel and the optical sensor array to collect light and to direct the collected light to the optical sensor array.

10. The device as in claim 9, wherein the optical sensor module further includes:
an optical diffraction pattern between the optical collimators and the display panel by diffracting the returned probe light into angled probe light to enter the optical collimators while reducing an amount of the returned probe light that is perpendicular to the display panel and enters the optical collimators.

11. The device as in claim 9, wherein:
the optical collimators are elongated channels in a direction perpendicular to the display panel and the optical layer between the optical collimators and the display is structured to direct the angled probe light to be substantially perpendicular to the display panel to enter the optical collimators while directing a portion of the probe light that is perpendicular to the display panel to be away from the direction of the optical collimators.

12. The device as in claim 1, wherein:
the optical sensor module includes a lens that collects light onto the optical sensor array.

13. The device as in claim 1, wherein:
each of the extra illumination light sources is structured to emit second probe light at a second probe wavelength different from a wavelength of the probe light; and
the optical sensor module is structured to measure returned probe light at different wavelengths to determine whether the fingerprint pattern is from a finger of a live person.

14. The device as in claim 1, further comprising:
one or more optical filters placed below a top surface of the top transparent layer to filter light entering the optical sensor array of the optical sensor module to block or reduce an amount of environmental light from entering the optical sensor array.

15. The device as in claim 14, wherein:
the one or more optical filters are designed to filter out infrared light or UV light.

16. The device as in claim 1, wherein:
the optical sensor module includes sidewalls formed on sides of the optical sensor array to block environmental light from entering the optical sensor array at large incident angles.

17. A method for operating an electronic device to detect a fingerprint by optical sensing, wherein the electronic device includes a display panel that displays images, a top transparent layer formed over the display panel as an interface for user touch operations and for transmitting the light from the display panel to display images, and an optical sensor array of optical detectors located under the display panel, the method comprising:
directing a first illumination probe beam from a first illumination light source outside the display panel to illuminate a designated fingerprint sensing area over the top transparent layer in a first illumination direction and to enter a user finger over the designated fingerprint sensing area to produce first scattered probe light by scattering of tissues inside the finger that propagates towards and passes the top transparent layer by transmission through internal tissues of ridges and valleys of the finger to carry both (1) a first 2-dimensional transmissive pattern representing a first fingerprint pattern formed by bridges and valleys of the finger, and (2) a first fingerprint topographical pattern that is associated with the illumination of internal tissues of ridges and valleys of the finger in the first illumination direction and is embedded within the first 2-dimensional transmissive pattern;
operating the optical sensor array to detect transmitted part of the first scattered probe light that passes through the top transparent layer and the display panel to reach the optical sensor array so as to capture both (1) the first 2-dimensional transmissive pattern, and (2) the first fingerprint topographical pattern;
directing a second illumination probe beam from a second illumination light source outside the display panel located separated from the from the first illumination light source, while turning off the first illumination light source, to illuminate the designated fingerprint sensing area over the top transparent layer in a second, different illumination direction and to enter the user finger to produce second scattered probe light by scattering of tissues inside the finger that propagates towards and passes the top transparent layer by transmission through internal tissues of ridges and valleys of the finger to carry both (1) a second 2-dimensional transmissive pattern representing a second fingerprint pattern formed by bridges and valleys of the finger, and (2) a second fingerprint topographical pattern that is associated with the illumination of the internal tissues of ridges and valleys of the finger in the second illumination direction and that is embedded within the second 2-dimensional transmissive pattern, wherein the second topographical pattern is different from the first topographical pattern due to different beam directions of the first and second illumination probe beams; operating the optical sensor array to detect transmitted part of the second scattered probe light that passes through the top transparent layer and the display panel to reach the optical sensor array so as to capture both (1) the second 2-dimensional transmissive pattern, and (2) the second fingerprint topographical pattern; and
processing the first and second fingerprint topographical patterns to extract a spatial shift between the first and second topographical patterns due to a difference in the first and second illumination directions and to determine whether the detected fingerprint pattern is from a natural finger based on the extracted spatial shift between the first and second topographical patterns,
wherein the first and second illumination light sources outside the display panel are controlled and operated independent of a display operation of the display panel.

18. The method as in claim 17, wherein:
the first and second fingerprint topographical patterns include different optical intensity variation patterns caused by internal tissues of ridges and valleys of the finger due to different illumination beam directions.

19. The method as in claim 17, comprising:
directing illumination light, separate from the first and second illumination probe beams, to pass through the top transparent layer to illuminate the finger in contact with the top transparent layer in the designated fingerprint sensing area;
using the optical sensor array to detect the illumination light that is reflected by the finger towards the optical sensor array and to capture an optical reflective pattern representing the fingerprint pattern of ridges and pattern of the finger; and
using both the captured optical reflective pattern and the first and second transmissive patterns to construct the detected fingerprint.

20. The method as in claim 19, wherein:
the display panel is an organic light emitting diode display (OLED) panel that includes display pixels and each display pixel includes different OLED pixels operable to emit light of different colors to generate colored light for each display pixel; and
the device further includes extra illumination light sources placed at the different locations are and are operated separately from the OLED panel to produce the illumination light for generating the optical reflective pattern representing the fingerprint pattern and the first and second illumination probe beams for generating the first and second transmissive patterns representing the fingerprint pattern.

21. The method as in claim 20, wherein:
one or more first extra illumination light sources responsible for producing the illumination light for generating the optical reflective pattern are located under the OLED panel; and
second extra illumination light sources responsible for producing the first and second illumination probe beams for generating the first and second transmissive patterns are located above OLED panel.

22. The method as in claim 21, comprising:
operating the first and second extra illumination light sources to emit light at a higher brightness level than a brightness level for light emission by the OLED pixels to increase a detection sensitivity of the optical sensor array.

23. The method as in claim 22, comprising:
operating the first and second extra illumination light sources in a flash mode to turn on and off each extra illumination light source in a short period for optical sensing by the optical sensor array to reduce power consumption associated with optical sensing by the optical sensor array.

24. The method as in claim 21, wherein optical sensing is performed by:
selectively turning on OLED pixels of the OLED panel underneath the designated fingerprint sensing area without turning on other OLED pixels of the OLED panel while simultaneously turning on the first extra illumination light sources to produce the optical reflective pattern for optical sensing by the optical sensor array;

further turning on the second extra illumination light sources to produce the optical transmissive pattern for optical sensing by the optical sensor array; and constructing the detected fingerprint pattern based on both (1) the optical reflective pattern captured by the optical sensor array from illumination by the selectively turned-on OLED pixels underneath the designated fingerprint sensing area and by the first extra illumination light sources, and (2) the optical transmissive pattern captured by the optical sensor array from illumination by the second extra illumination light sources.

25. The method as in claim 24, further comprising:

in addition to obtaining the optical transmissive pattern captured by the optical sensor array from illumination by the second extra illumination light sources, using incident light from the environmental light in a spectral range from 590 nm to 950 nm in which a human finger exhibits optical transmission to provide additional illumination for obtaining the optical transmissive pattern captured by the optical sensor array to enhance the detection sensitivity of the optical sensing in obtaining the detected fingerprint pattern.

26. The method as in claim 17, comprising:

using extra illumination light separate from light for displaying images at the display panel to illuminate a finger to produce scattered light from internal tissues of the finger to the optical sensor array to detect a glucose level in the finger.

27. The method as in claim 17, comprising:

operating the optical sensor array to obtain measurements of received light at two or more different wavelengths; and comparing an extinction ratio of the received light at the optical sensor array at the two or more different wavelengths to determine whether the received light is from living tissues of a live person.

28. The method as in claim 17, comprising:

operating the optical sensor array to capture different fingerprint patterns at different times to monitor a time-domain evolution of the fingerprint ridge pattern deformation that indicates a time-domain evolution of a press force by a finger in contact with the top transparent layer.

* * * * *